US010604552B2

(12) United States Patent
Leonard et al.

(10) Patent No.: US 10,604,552 B2
(45) Date of Patent: Mar. 31, 2020

(54) GENERATION OF NOVEL METABOLITE-RESPONSIVE TRANSCRIPTION REGULATOR BIOSENSORS

(71) Applicant: NORTHWESTERN UNIVERSITY, Evanstion, IL (US)

(72) Inventors: Joshua N. Leonard, Wilmette, IL (US); Andrew K. D. Younger, Evanston, IL (US); Keith E. J. Tyo, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/342,777

(22) PCT Filed: Oct. 17, 2017

(86) PCT No.: PCT/US2017/056933
§ 371 (c)(1),
(2) Date: Apr. 17, 2019

(87) PCT Pub. No.: WO2018/075486
PCT Pub. Date: Apr. 26, 2018

(65) Prior Publication Data
US 2019/0345209 A1    Nov. 14, 2019

Related U.S. Application Data

(60) Provisional application No. 62/409,127, filed on Oct. 17, 2016.

(51) Int. Cl.
*C07K 14/47* (2006.01)
*C12N 15/10* (2006.01)
(Continued)

(52) U.S. Cl.
CPC ...... *C07K 14/4702* (2013.01); *C12N 15/1055* (2013.01); *C12Q 1/6897* (2013.01);
(Continued)

(58) Field of Classification Search
CPC ............ C07K 14/4702; C07K 2319/70; C07K 2319/81; C12N 15/1055; C12Q 1/6897; G01N 33/566
See application file for complete search history.

(56) References Cited

U.S. PATENT DOCUMENTS

2016/0202256 A1    7/2016   Church et al.

OTHER PUBLICATIONS

International Search Report and Written Opinion Received in PCT/US2017/056933 dated Feb. 14, 2018 (7 pages).
(Continued)

*Primary Examiner* — Jeremy C Flinders
(74) *Attorney, Agent, or Firm* — Foley & Lardner LLP

(57) ABSTRACT

Disclosed are systems, components, and methods for sensing a ligand in a cell or a reaction mixture. The disclosed systems, components, and methods may include and/or utilize a fusion protein comprising a ligand-binding protein and a DNA-binding protein. The fusion protein binds the ligand of the ligand-binding protein and modulates expression of a reporter gene operably linked to a promoter that is engineered to include specific binding sites for the DNA-binding protein. The difference in expression of the reporter gene in the presence of the ligand versus expression of the reporter gene in the absence of the ligand can be correlated to the concentration of the ligand in a reaction mixture.

23 Claims, 49 Drawing Sheets

Specification includes a Sequence Listing.

(51) Int. Cl.
*C12Q 1/6897* (2018.01)
*G01N 33/566* (2006.01)

(52) U.S. Cl.
CPC ....... *G01N 33/566* (2013.01); *C07K 2319/70* (2013.01); *C07K 2319/81* (2013.01)

(56) References Cited

OTHER PUBLICATIONS

Nadler D. C. et al., "Rapid construction of metabolite biosensors using domain insertion profiling," Nature Communications, Jul. 14, 2016 (11 pages).

Feng J. et al, "A general strategy to construct small molecule biosensors in eukaryotes," eLife, Dec. 29, 2015 (23 pages).

Jeong J. et al., "Monitoring of conformational change in maltose binding protein using split green fluorescent protein," Biochemical and Biophysical Research Communications, 2006, vol. 339, pp. 647-651 (5 pages).

Wehr M. C. et al., "Split protein biosensor assays in molecular pharmacological studies," Drug Discovery Today, Mar. 2016, vol. 21, No. 3, pp. 415-429 (15 pages).

A

| Shorthand | Description of feature |
|---|---|
| BS in core | Number of binding sites in the core |
| pairs in core | Number of pairs in the core |
| BS upstream | Number of binding sites upstream of -35 region |
| pairs upstream | Number of pairs upstream of -35 region |
| BS downstream | Number of binding sites downstream of -10 box |
| pairs downstream | Number of pairs downstream of -10 box |
| length | Length of the promoter in base pairs |
| spacer -10 | Base pairs downstream of the -10 box, before the first binding site |
| spacer -35 | Base pairs upstream of the -35 region, before the first binding site |
| spacer inside -10 | Base pairs upstream of the -10 box, before the first binding site |
| spacer inside -35 | Base pairs downstream of the -35 region, before the first binding site |
| core middle space | Non-binding site base pairs in the core |
| ave down space | Average number of base pairs between binding sites downstream |
| ave up space | Average number of base pairs between binding sites up stream |
| down length | Base pairs downstream of the -10 box |
| up length | Base pairs upstream of the -35 region |
| lopsidedness | Absolute value of (binding sites upstream) - (binding sites downstream) |

Figure 3

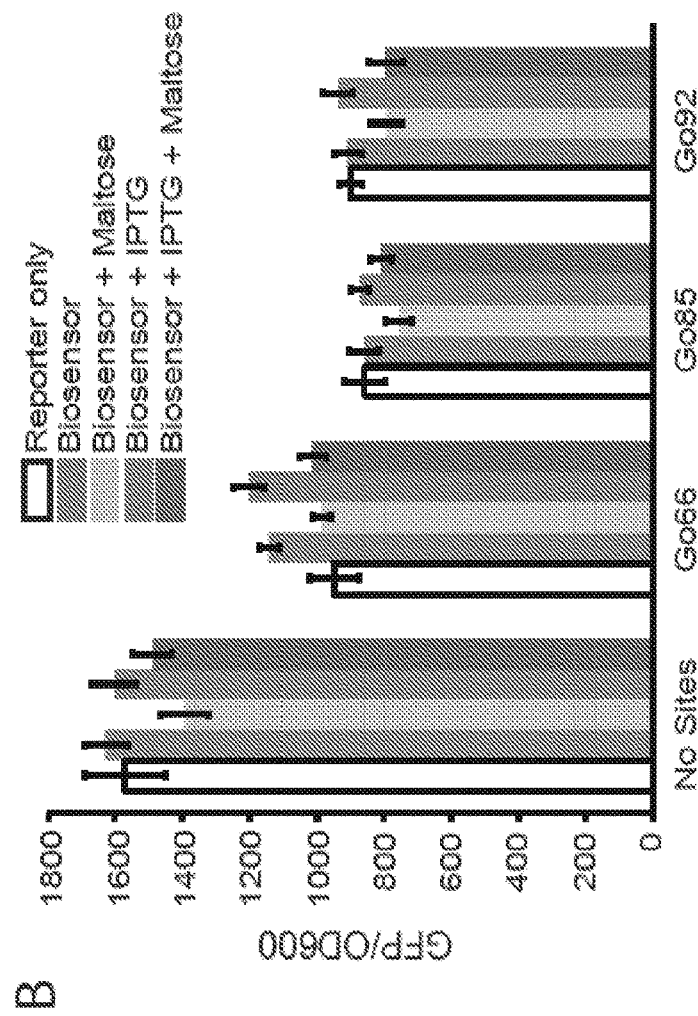
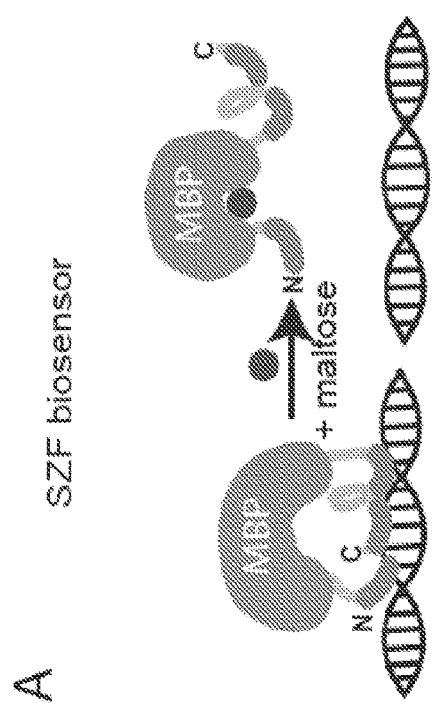
Figure 4

A

C

| Promoter feature | Sequence and coloring |
|---|---|
| -10 Box | TATAAT |
| -35 Box | TTGACA |
| BCR-ABL1 binding site | gcaggaagcc |
| BCR-ABL1 1st finger | gca |
| BCR-ABL1 2nd finger | gaa |
| BCR-ABL1 3rd finger | gcc |
| Spacer sequence | nnnnn |

| pGoXX | Promoter Sequence 5'-3' | pGoXX | Promoter sequence 5'-3' | pGoXX | Promoter sequence 5'-3' | pGoXX | Promoter sequence 5'-3' |
|---|---|---|---|---|---|---|---|
| No Sites | | Go20 | See SEQ ID NO:18 | Go45 | See SEQ ID NO:35 | Go68 | See SEQ ID NO:52 |
| Go03 | See SEQ ID NO:2 | Go21 | See SEQ ID NO:19 | Go46 | See SEQ ID NO:36 | Go69 | See SEQ ID NO:53 |
| Go04 | See SEQ ID NO:3 | Go22 | See SEQ ID NO:20 | Go49 | See SEQ ID NO:37 | Go70 | See SEQ ID NO:54 |
| Go05 | See SEQ ID NO:4 | Go23 | See SEQ ID NO:21 | Go50 | See SEQ ID NO:38 | Go71 | See SEQ ID NO:55 |
| Go06 | See SEQ ID NO:5 | Go24 | See SEQ ID NO:22 | Go51 | See SEQ ID NO:39 | Go72 | See SEQ ID NO:56 |
| Go07 | See SEQ ID NO:6 | Go25 | See SEQ ID NO:23 | Go56 | See SEQ ID NO:40 | Go73 | See SEQ ID NO:57 |
| Go08 | See SEQ ID NO:7 | Go26 | See SEQ ID NO:24 | Go57 | See SEQ ID NO:41 | Go74 | See SEQ ID NO:58 |
| Go10 | See SEQ ID NO:8 | Go29 | See SEQ ID NO:25 | Go58 | See SEQ ID NO:42 | Go75 | See SEQ ID NO:59 |
| Go11 | See SEQ ID NO:9 | Go30 | See SEQ ID NO:26 | Go59 | See SEQ ID NO:43 | Go76 | See SEQ ID NO:60 |
| Go12 | See SEQ ID NO:10 | Go31 | See SEQ ID NO:27 | Go60 | See SEQ ID NO:44 | Go77 | See SEQ ID NO:61 |
| Go13 | See SEQ ID NO:11 | Go32 | See SEQ ID NO:28 | Go61 | See SEQ ID NO:45 | Go78 | See SEQ ID NO:62 |
| Go14 | See SEQ ID NO:12 | Go33 | See SEQ ID NO:29 | Go62 | See SEQ ID NO:46 | Go79 | See SEQ ID NO:63 |
| Go15 | See SEQ ID NO:13 | Go35 | See SEQ ID NO:30 | Go63 | See SEQ ID NO:47 | Go85 | See SEQ ID NO:64 |
| Go16 | See SEQ ID NO:14 | Go36 | See SEQ ID NO:31 | Go64 | See SEQ ID NO:48 | Go88 | See SEQ ID NO:65 |
| Go17 | See SEQ ID NO:15 | Go39 | See SEQ ID NO:32 | Go65 | See SEQ ID NO:49 | Go90 | See SEQ ID NO:66 |
| Go18 | See SEQ ID NO:16 | Go40 | See SEQ ID NO:33 | Go66 | See SEQ ID NO:50 | Go91 | See SEQ ID NO:67 |
| Go19 | See SEQ ID NO:17 | Go41 | See SEQ ID NO:34 | Go67 | See SEQ ID NO:51 | Go92 | See SEQ ID NO:68 |

| Feature Number | Shorthand | Description |
|---|---|---|
| 1 | BS in core | Number of binding sites in the core |
| 2 | pairs in core | Number of pairs in the core |
| 3 | BS upstream | Number of binding sites upstream of the -35 region |
| 4 | pairs upstream | Number of pairs upstream of the -35 region |
| 5 | BS downstream | Number of binding sites downstream of the -10 box |
| 6 | pairs downstream | Number of pairs downstream of the -10 box |
| 7 | length | Length of the promoter in base pairs |
| 8 | spacer -10 | Base pairs downstream of the -10 box, before the first binding site |
| 9 | spacer -35 | Base pairs upstream of the -35 region, before the first binding site |
| 10 | spacer inside -10 | Base pairs upstream of the -10 box, before the first binding site |
| 11 | spacer inside -35 | Bse pairs downstream of the -35 region, before the first binding site |
| 12 | core middle space | Non-binding site base pairs in the core |
| 13 | ave down space | Average number of base pairs between binding sites downstream |
| 14 | ave up space | Average number of base pairs between binding sites upstream |
| 15 | down length | Base pairs downstream of the -10 box |
| 16 | up length | base pairs upstream of the -35 box |
| 17 | lopsidedness | Absolute value of (binding sites upstream) - (binding sites downstream) |

Figure 10

| Biosensor | SP | SP-Zif | SP-mC | mC-SP |
|---|---|---|---|---|
| Fold repression | 4.1 ± 0.1 | 2.4 ± 0.4 | 3.5 ± 0.1 | 6.0 ± 0.4 |
| Fold alleviation | 3.0 ± 0.1 | 1.8 ± 0.3 | 2.0 ± 0.1 | 3.8 ± 0.3 |

Figure 14

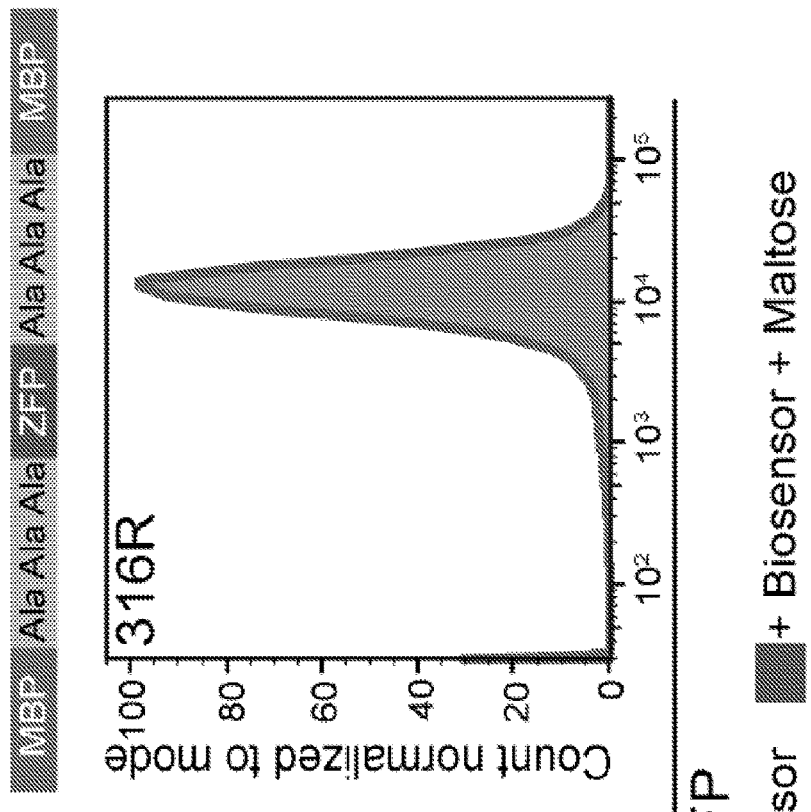
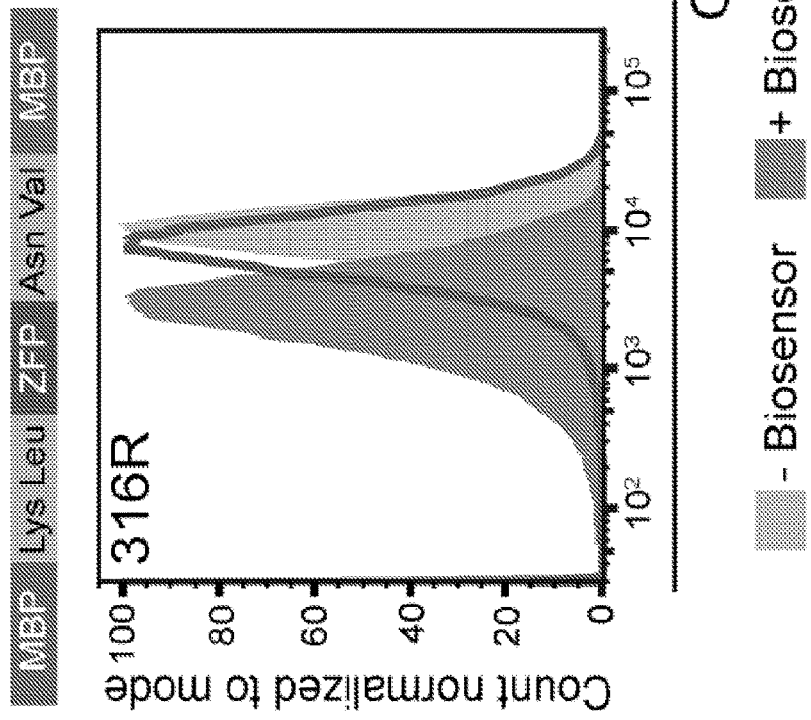
Figure 19

SEQUENCE LISTING

```
<160> NUMBER OF SEQ ID NOS: 86

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Artificial constitutive promoter for E.coli

<400> SEQUENCE: 1
ttgacagata gctcactact atgtataatg atagcaagac tcc                        43

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 2
ttgacagcag aagccgcaga agcctataat gatagcgcag aagccgcaga agcc            54

<210> SEQ ID NO 3
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 3
ttgacagata gctcagtcat aggtataatg atagcgcaga agccgcagaa gccactagag      60
cagaagccgc agaagcc                                                    77

<210> SEQ ID NO 4
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 4
ttgacagata gctcagtcat aggtataatg atagcgcaga agccgcagaa gccactagag      60
cagaagccgc agaagccact agagcagaag ccgcagaagc c                         101

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 5
ttgacagcag aagccgcaga agcctataat gatagcgcag aagccgcaga agccactaga     60
gcagaagccg cagaagcc                                                  78

<210> SEQ ID NO 6
<211> LENGTH: 102
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 6
ttgacagcag aagccgcaga agcctataat gatagcgcag aagccgcaga agccactaga      60
gcagaagccg cagaagccag gtgagcagaa gccgcagaag cc                        102

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 7
gcagaagccg cagaagcctt gacagatagc tcagtcatag gtataatgat agc            53

<210> SEQ ID NO 8
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 8
gcagaagccg cagaagccag gtgagcagaa gccgcagaag ccactagagc agaagccgca     60
gaagccttga cagatagctc agtcataggt ataatgatag c                        101

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 9
gcagaagccg cagaagcctt gacagcagaa gccgcagaag cctataatga tagc           54

<210> SEQ ID NO 10
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 10
```

```
gcagaagccg cagaagccac tagagcagaa gccgcagaag ccttgacagc agaagccgca    60
gaagcctata at                                                        72
```

<210> SEQ ID NO 11
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 11

```
gcagaagccg cagaagccag gtgagcagaa gccgcagaag ccactagagc agaagccgca    60
gaagccttga cagcagaagc cgcagaagcc tataatgata gc                      102
```

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 12

```
ttgacagcag aagccgcaga agcctataat                                     30
```

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 13

```
ttgacagata gctcagcaga agcctataat gatagc                              36
```

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 14

```
ttgacagcag aagccagtca taggtataat gatagc                              36
```

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Artificial constitutive promoter for E. coli
      including BCR-ABL1 binding sites

<400> SEQUENCE: 15
ttgacagata gcagaagcct aggtataatg atagc                                35

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 16
ttgacagata gcagaagcct aggtataatg cagaagccga tagc                      44

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 17
ttgacagata gctcagtcat aggtataatg atagcgcaga agccgcagaa gcc            53

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcagaagcct tgacagatag cagaagccta ggtataatga tagc                      44

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 19
gcagaagcct tcgtagcgtt gacagcagaa gccagtcata ggtataatga tagc           54

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites
```

<400> SEQUENCE: 20
ttgacagata gctcagcaga agcctataat gatagcgcag aagcc            45

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 21
gcagaagccg cagaagcctt gacagcagaa gccgcagaag cctataatga tagcgcagaa    60
gccgcagaag ccactagagc agaagccgca gaagccaggt gagcagaagc cgcagaagcc   120

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 22
gcagaagccg cagaagccag gtgagcagaa gccgcagaag ccttgacagc agaagccgca    60
gaagcctata atgatagcgc agaagccgca gaagccacta gagcagaagc cgcagaagcc   120

<210> SEQ ID NO 23
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 23
gcagaagccg cagaagcctt gacagcagaa gccgcagaag cctataatga tagcgcagaa    60
gccgcagaag ccgcagaagc cgcagaagcc                                     90

<210> SEQ ID NO 24
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 24
gcagaagccg cagaagcctt gacagcagaa gccgcagaag cctataatga tagcgcagaa    60
gccgcagaag ccgcagaagc cgcagaagcc gcagaagccg cagaagcc                108

<210> SEQ ID NO 25

```
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 25
ttgacagcag aagccgcaga agcctataat gatagcgcag aagccgcaga agccactaga      60
gcagaagccg cagaagccag gtgagcagaa gccgcagaag ccactagagc agaagccgca     120
gaagcc                                                                126

<210> SEQ ID NO 26
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 26
ttgacagcag aagccgcaga agcctataat gatagcgcag aagccgcaga agccactaga      60
gcagaagccg cagaagccag gtgagcagaa gccgcagaag ccactagagc agaagccgca     120
gaagccacta gagcagaagc cgcagaagcc                                      150

<210> SEQ ID NO 27
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 27
gcagaagccg cagaagcctt gttgacagca gaagccgcag aagcctataa tgatagcagc      60
gcagaagccg cagaagccgg tgcagaagcc gcagaagccc tgcagaagc cgcagaagcc     120

<210> SEQ ID NO 28
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 28
gcagaagccg gagcagaagc cttgttgaca gcagaagccg cagaagccta taatgatagc      60
agcgcagaag ccgctgcaga agccggtgca gaagccaatg cagaagcccc tgcagaagcc     120
gtagcagaag cc                                                         132

<210> SEQ ID NO 29
<211> LENGTH: 132
```

<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Artificial constitutive promoter for E. coli
    including BCR-ABL1 binding sites

<400> SEQUENCE: 29
gcagaagccg cagaagcctt tgggttgaca gcagaagccg cagaagccta taatgatagc    60
agggacgcag aagccgcaga agccgaacgt gcagaagccg cagaagcccc taatgcagaa   120
gccgcagaag cc                                                       132

<210> SEQ ID NO 30
<211> LENGTH: 144
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Artificial constitutive promoter for E. coli
    including BCR-ABL1 binding sites

<400> SEQUENCE: 30
gcagaagccg cagaagcctt gacagcagaa gccgcagaag cctataatga tagcgcagaa    60
gccgcagaag ccactagagc agaagccgca gaagccaggt gagcagaagc cgcagaagcc   120
actagagcag aagccgcaga agcc                                          144

<210> SEQ ID NO 31
<211> LENGTH: 138
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Artificial constitutive promoter for E. coli
    including BCR-ABL1 binding sites

<400> SEQUENCE: 31
ttgacagcag aagccgcaga agcctataat gatagcgcag aagccaatgc agaagccact    60
agagcagaag cctaagcaga agccaggtga gcagaagccg gagcagaagc cactagagca   120
gaagcctatg cagaagcc                                                 138

<210> SEQ ID NO 32
<211> LENGTH: 108
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Artificial constitutive promoter for E. coli
    including BCR-ABL1 binding sites

<400> SEQUENCE: 32
gcagaagccg cagaagccgc agaagccgca gaagccttga cagcagaagc cgcagaagcc    60
tataatgata gcgcagaagc cgcagaagcc gcagaagccg cagaagcc                108

<210> SEQ ID NO 33
<211> LENGTH: 126
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Artificial constitutive promoter for E. coli
including BCR-ABL1 binding sites

<400> SEQUENCE: 33
gcagaagccg cagaagccgc agaagccgca gaagccgcag aagccgcaga agccttgaca       60
gcagaagccg cagaagccta taatgatagc gcagaagccg cagaagccgc agaagccgca      120
gaagcc                                                                126

<210> SEQ ID NO 34
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Artificial constitutive promoter for E. coli
including BCR-ABL1 binding sites

<400> SEQUENCE: 34
gcagaagccg cagaagccgt tgcagaagcc gcagaagcca tagcagaagc cgcagaagcc       60
ttgacagcag aagccgcaga agcctataat gatagcgcag aagccgcaga agcctaagca      120
gaagccgcag aagcc                                                      135

<210> SEQ ID NO 35
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Artificial constitutive promoter for E. coli
including BCR-ABL1 binding sites

<400> SEQUENCE: 35
ttgacagcag aagccgcaga agcctataat gcagaagccg cagaagccac tagagcagaa       60
gccgcagaag ccaggtgagc agaagccgca gaagccacta gagcagaagc cgcagaagcc      120

<210> SEQ ID NO 36
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Artificial constitutive promoter for E. coli
including BCR-ABL1 binding sites

<400> SEQUENCE: 36
gcagaagccg cagaagcctt gacagcagaa gccgcagaag cctataatgc agaagccgca       60
gaagccgcag aagccgcaga agccgcagaa gccgcagaag cc                         102

<210> SEQ ID NO 37
<211> LENGTH: 109
<212> TYPE: DNA
<213> ORGANISM: Artificial Sequence
<220> FEATURE:
<223> OTHER INFORMATION: Description of Artificial Sequence: Synthetic

```
    polynucleotide
<220> FEATURE:
<223> OTHER INFORMATION: Artificial constitutive promoter for E. coli
      including BCR-ABL1 binding sites

<400> SEQUENCE: 37
gcagaagccg cagaagcctt gacagcagaa gccagcagaa gcctataatg atagcgcaga      60
agccgcagaa gccgcagaag ccgcagaagc cgcagaagcc gcagaagcc               109

<210> SEQ ID NO 38
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 38
gcagaagcca gcagaagcct tgacagcaga agccagcaga agcctataat gatagcgcag      60
aagccagcag aagccgcaga agccagcaga agccgcagaa gccagcagaa gcc           113

<210> SEQ ID NO 39
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 39
gcagaagcca gcagaagcct tgacagcaga agccagcaga agcctataat gcagaagcca      60
gcagaagccg cagaagccag cagaagccgc agaagccagc agaagcc                  107

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 40
ttgacagcag cagcagcagc agcatataat gatagcgaag ccgaagccga agcc              54

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 41
ttgacagcag cagcagcagc agcatataat gaagccgaag ccgaagcc                    48
```

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 42
ttgacagaag ccgaagccga agcctataat gatagcgcag cagcagcagc agca    54

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 43
ttgacagaag ccgaagccga agcctataat gcagcagcag cagcagca    48

<210> SEQ ID NO 44
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 44
ttgacagcag aagccgcaga agcctataat gatagcgccg aagcagccga agca    54

<210> SEQ ID NO 45
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttgacagccg aagcagccga agcatataat gatagcgcag aagccgcaga agcc    54

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 46
ttgacagccg aagcagccga agcatataat gccgaagcag ccgaagca    48

<210> SEQ ID NO 47

```
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 47
ttgacagcag aagccgcaga agcctataat gatagcgaag cagccgcaga agcc          54

<210> SEQ ID NO 48
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 48
ttgacagaag cagccgcaga agcctataat gatagcgaag cagccgcaga agcc          54

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 49
ttgacagaag cagccgcaga agcctataat gatagcgcag aagccgcaga agcc          54

<210> SEQ ID NO 50
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 50
gcagaagccg cagaagcctt gacagcagaa gccgcagaag cctataatgc agaagccgca    60
gaagcc                                                                66

<210> SEQ ID NO 51
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Artificial constitutive promoter for E. coli
      including BCR-ABL1 binding sites

<400> SEQUENCE: 51
gcagaagccg cagaagcctt gacagcagaa gccgcagaag cctataatga tagcgcagaa    60
```
gccgcagaag ccgcagaagc cgcagaagcc gcagaagccg cagaagccgc agaagccgca    120
gaagcc                                                              126

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 52
ttgacagcag aagccgcaga agcctataat gatagagaag ccgcagaagc c             51

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 53
ttgacagcag aagccgcaga agcctataat gatagcagaa gccgcagaag cc            52

<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 54
ttgacagcag aagccgcaga agcctataat gatgcagaag ccgcagaagc c             51

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 55
ttgacagcag aagccgcaga agcctataat gagcagaagc cgcagaagcc               50

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli including BCR-ABL1 binding sites

<400> SEQUENCE: 56
ttgacagcag aagccgcaga agcctataat ggcagaagcc gcagaagcc    49

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 57
ttgacagcag aagccgcaga agcctataat gcagaagccg cagaagcc    48

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 58
ttgacagcag aagcagaagc agaatataat gatagc    36

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 59
ttgacagcag ccgcagccgc agcctataat gatagc    36

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 60
ttgacagaag cagaagcaga agcatataat gatagc    36

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Artificial constitutive promoter for E. coli
      including BCR-ABL1 binding sites

<400> SEQUENCE: 61
ttgacagaag ccgaagccga agcctataat gatagc                                    36

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 62
ttgacagccg cagccgcagc cgcatataat gatagc                                    36

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 63
ttgacagccg aagccgaagc cgaatataat gatagc                                    36

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 64
gcagaagcct tgacagcaga agccgcagaa gcctataatg cagaagcc                       48

<210> SEQ ID NO 65
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 65
gcagaagcct tgacagcaga agccagcaga agcctataat gcagaagcc                      49

<210> SEQ ID NO 66
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Artificial constitutive promoter for E. coli
      including BCR-ABL1 binding sites

<400> SEQUENCE: 66
gcagaagcct tgacagatag ctcagcagaa gcctataatg cagaagcc                48

<210> SEQ ID NO 67
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 67
gcagaagcct tgacagcaga agccgatagc tcatataatg cagaagcc                48

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Artificial constitutive promoter for E. coli
      including BCR-ABL1 binding sites

<400> SEQUENCE: 68
gcagaagcct tgacagatag gcagaagccc tcatataatg cagaagcc                48

<210> SEQ ID NO 69
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Transposons and scar options

<400> SEQUENCE: 69
agatctgcgg ccgcgcacga aaacgcgaa agcgtttcac gataaatgcg aaaa           54

<210> SEQ ID NO 70
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse complement of MuA transposase
      recognition sequence 2 and 1

<400> SEQUENCE: 70
ttttcgcatt tatcgtgaaa cgctttcgcg ttttcgtgc gcggccgcag atct            54

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: MuA transposase recognition sequence 1 and 2

<400> SEQUENCE: 71
gcacgaaaaa cgcgaaagcg tttcacgata aatgcgaaaa                                40

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse complements of recognition sequences 1
      and 2

<400> SEQUENCE: 72
ttttcgcatt tatcgtgaaa cgctttcgcg tttttcgtgc                                40

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 73
nnnnnnnntg cggccgcatg                                                      20

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (11)..(18)
<223> OTHER INFORMATION: a, c, t, g, unknown or other

<400> SEQUENCE: 74
ngcggccgca nnnnnnnn                                                        18

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 75
```
nnnnnnnntg cggccgcnat g                                          21

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(17)
<223> OTHER INFORMATION: a, c, t, g, unknown or other

<400> SEQUENCE: 76
gcggccgcan nnnnnnn                                               17

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (18)..(19)
<223> OTHER INFORMATION: a, c, t, g, unknown or other

<400> SEQUENCE: 77
nnnnnnnntg cggccgcnna tg                                         22

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (12)..(19)
<223> OTHER INFORMATION: a, c, t, g, unknown or other

<400> SEQUENCE: 78
nngcggccgc annnnnnnn                                             19

<210> SEQ ID NO 79
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acactgacga catggttcta cacaacgatt catacatagc taaaaggtac c          51

<210> SEQ ID NO 80
<211> LENGTH: 42
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 80
acactgacga catggttcta caggcaagct gattgcttac cc                    42

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acactgacga catggttcta caacaggcga aagggatcc                        40

<210> SEQ ID NO 82
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acactgacga catggttcta catctagggc tagctctagc cat                   43

<210> SEQ ID NO 83
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tacggtagca gagacttggt ctctagggct agctctagcc at                    42

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tacggtagca gagacttggt ctgccagctc tttgttcgga c                     41

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tacggtagca gagacttggt ctgggtgttc aataattggg catgc                 45

<210> SEQ ID NO 86
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 86
tacggtagca gagacttggt ctacaggcga gaagggatcc                           40
```

GENERATION OF NOVEL METABOLITE-RESPONSIVE TRANSCRIPTION REGULATOR BIOSENSORS

CROSS-REFERENCE TO RELATED PATENT APPLICATIONS

This application claims the benefit of priority under 35 U.S.C. § 119(e) to U.S. Provisional Patent Application No. 62/409,127, filed on Oct. 17, 2016, the content of which is incorporated by reference in its entirety.

STATEMENT REGARDING FEDERALLY SPONSORED RESEARCH OR DEVELOPMENT

This invention was made with government support under MCB1341414 awarded by the National Science Foundation, FP-91761101-0 awarded by the Environmental Protection Agency (EPA), and MH103910 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jul. 12, 2019, is named 121384-0133_SL.txt and is 31,170 bytes in size.

BACKGROUND

The field of the invention relates to biosensors comprising recombinant proteins and reporter systems. In particular, the field of the invention relates to biosensors comprising recombinant proteins that bind to a ligand, such as a cellular metabolite, and then modulate transcription of a reporter based on binding to the ligand.

Efforts to engineer microbial factories have benefitted from mining biological diversity and high throughput synthesis of novel enzymatic ensembles, yet screening and optimizing metabolic pathways remain rate-limiting steps. Metabolite-responsive biosensors may help to address these persistent challenges by enabling the monitoring of metabolite levels in individual cells and the implementation of metabolite-responsive feedback control. We are currently limited to naturally-evolved biosensors, which are insufficient for monitoring many metabolites of interest. Thus, a method for engineering novel biosensors would be powerful, yet we lack a generalizable approach that enables the construction of a wide range of biosensors. As a step towards this goal, we developed a bottom-up strategy for converting metabolite-binding proteins into metabolite-responsive transcriptional regulators. By pairing a modular protein design approach with a library of synthetic promoters and applying robust statistical analyses, we identified quantitative design principles for engineering biosensor-regulated promoters and for achieving design-driven improvements of biosensor performance. We demonstrated the feasibility of this strategy by fusing a programmable DNA binding motif (zinc finger module) with a model ligand binding protein (maltose binding protein), to generate a novel biosensor conferring maltose-regulated gene expression. This technology enables the design of novel biosensors for diverse synthetic biology applications.

SUMMARY

Disclosed are systems, components, and methods for sensing a ligand in a cell or a reaction mixture. The disclosed systems, components, and methods may include and/or utilize a fusion protein comprising a ligand-binding protein and a DNA-binding protein that otherwise may be referred to as a "biosensor." The fusion protein, or biosensor, binds the ligand of the ligand-binding protein and modulates expression of a reporter gene operably linked to a promoter that is engineered to include specific binding sites for the DNA-binding protein. The difference in expression of the reporter gene in the presence of the ligand versus expression of the reporter gene in the absence of the ligand can be correlated to the concentration of the ligand in the system. Also disclosed are recombinant methods for preparing and selecting fusion proteins that function as biosensors in the disclosed systems and methods.

BRIEF DESCRIPTION OF THE FIGURES

FIG. 7. Engineered promoter library details. Each BCR-ABL1-based promoter used in this study is listed and annotated as per the key at top. All Zif268 promoters (not listed) are identical in every way to their BCR-ABL1 counterparts except that the Zif268 binding site (GCGTGGGCG) replaces each instance of the BCR-ABL1 binding site.

FIG. 14. Fold induction and alleviation calculated using metrics previously applied to natural biosensors. Using the fold induction methods described by Rogers et al. (2015), fold repression was calculated by dividing the (maximum, uninduced background subtracted $GFP/OD_{600}$) by the (induced, background subtracted $GFP/OD_{600}$, repressed fluorescence). Fold alleviation was similarly calculated by dividing the (maximum, background subtracted $GFP/OD_{600}$, maltose-induced fluorescence), by the (induced, background subtracted $GFP/OD_{600}$, repressed fluorescence). $GFP/OD_{600}$ values were calculated 10 hours after induction. Each range indicated is one standard deviation, in which error was propagated according to the division rule.

FIG. 20B discloses SEQ ID NOS 73-78, respectively, in order of appearance.

DETAILED DESCRIPTION

Figure 1:
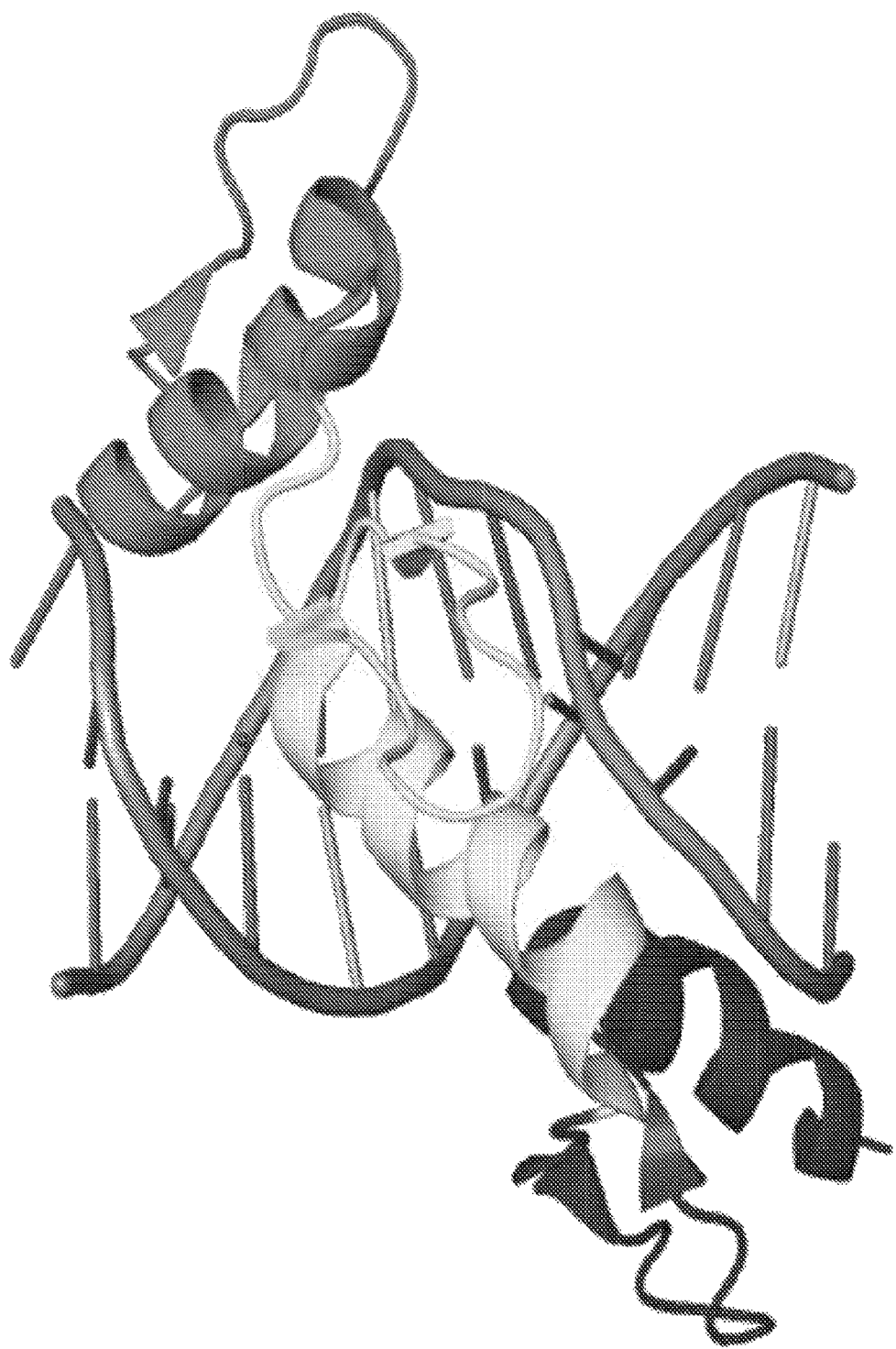
FIG. 1. Developing novel zinc finger protein-regulated constitutive promoters. (A) Crystal structure of a $Cys_2$-$His_2$ class of zinc finger binding to its cognate 9 bp DNA sequence (PDB #4R2A) (B) Repression of the constitutive promoter library by BCR-ABL1 (normalized to No Sites control, which lacks BCR-ABL1 binding sites) (C) Relative expression of the top 5 most repressible promoters was evaluated during both exponential growth (as in panel B) and after reaching stationary phase. (D and E) Select promoter constructs were evaluated by flow cytometry to assess variation in expression and repression across the population; one plot representative of three biological replicates is shown for each condition. A concentration of 1% arabinose was used to induce the expression of the BCR-ABL1 zinc finger. Relative expression is defined as the ratio of GFP/OD600 (for any given promoter) of the induced case relative to that of the uninduced case, divided by this same ratio for the No Sites promoter (a full description and rationale can be found in the Materials and Methods section). Relative expression values calculated from these data are explicitly compared to comparable microplate assay-based metrics in FIG. 9. Microplate data were collected over 7 sequential time points, spanning ~1.5 h of mid-exponential phase growth, and averaged. All data represent mean values calculated from three independent experiments, and error bars represent one standard deviation.
Figure 1:
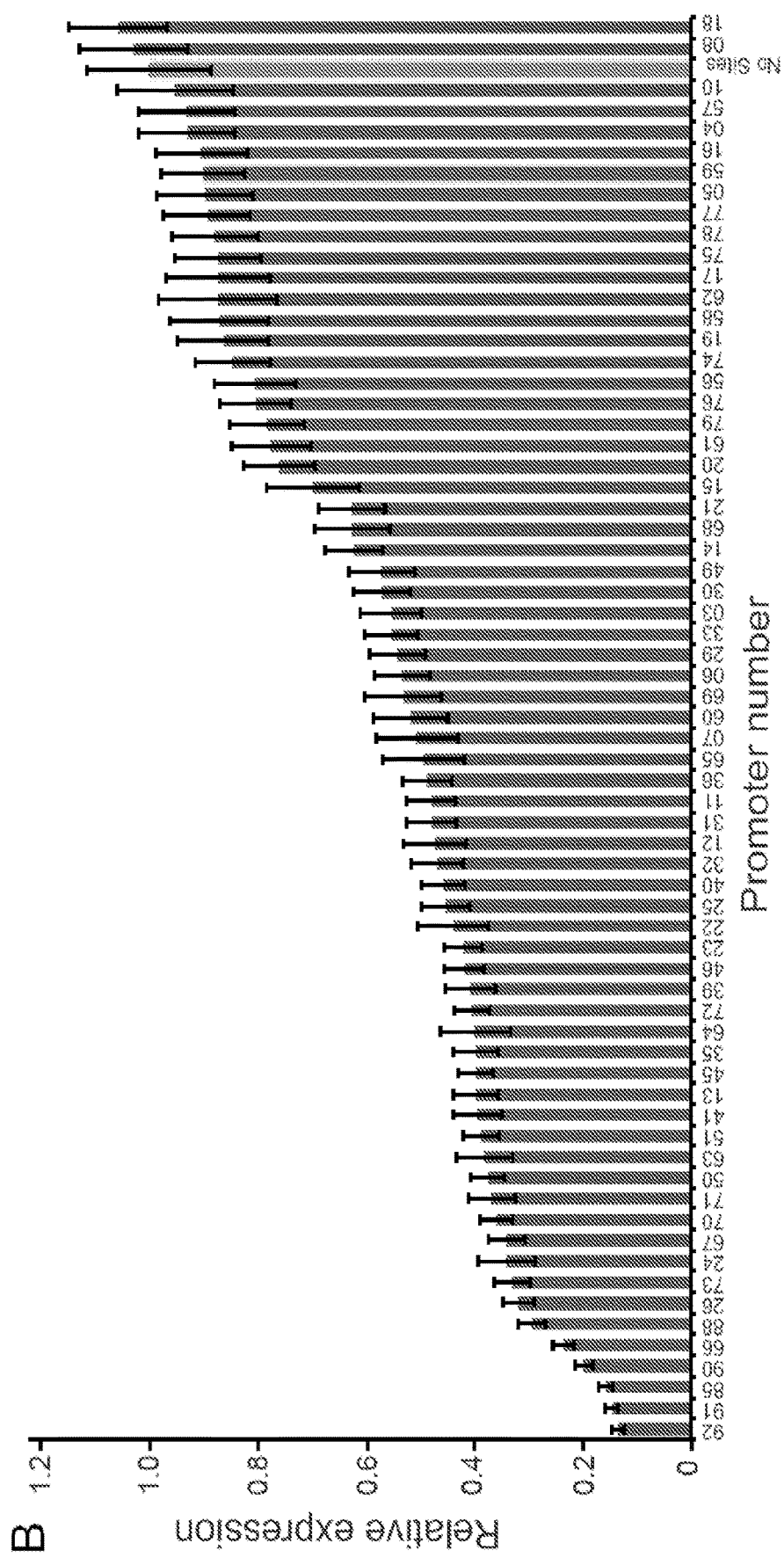
Figure 1:
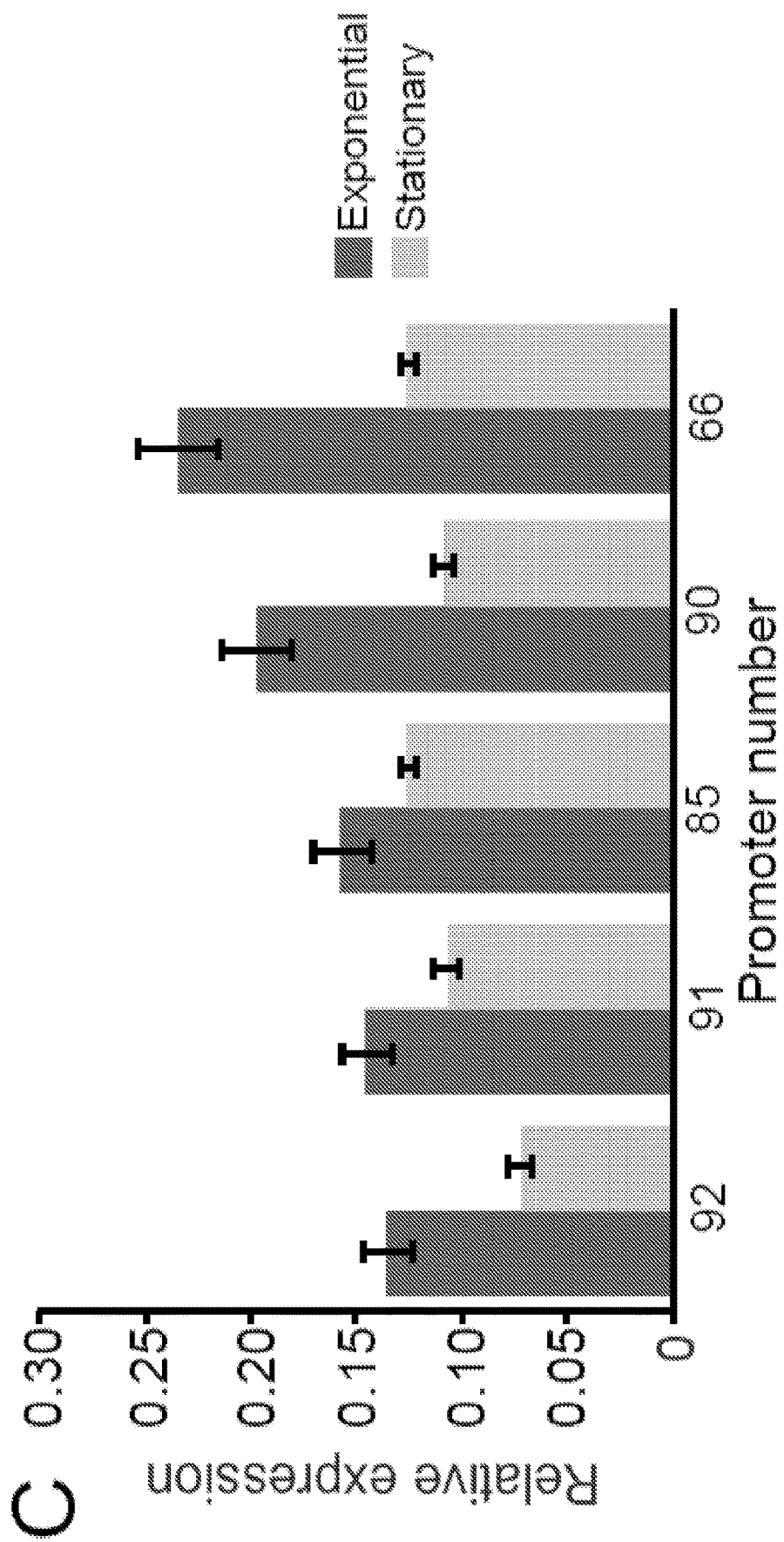
Figure 1:
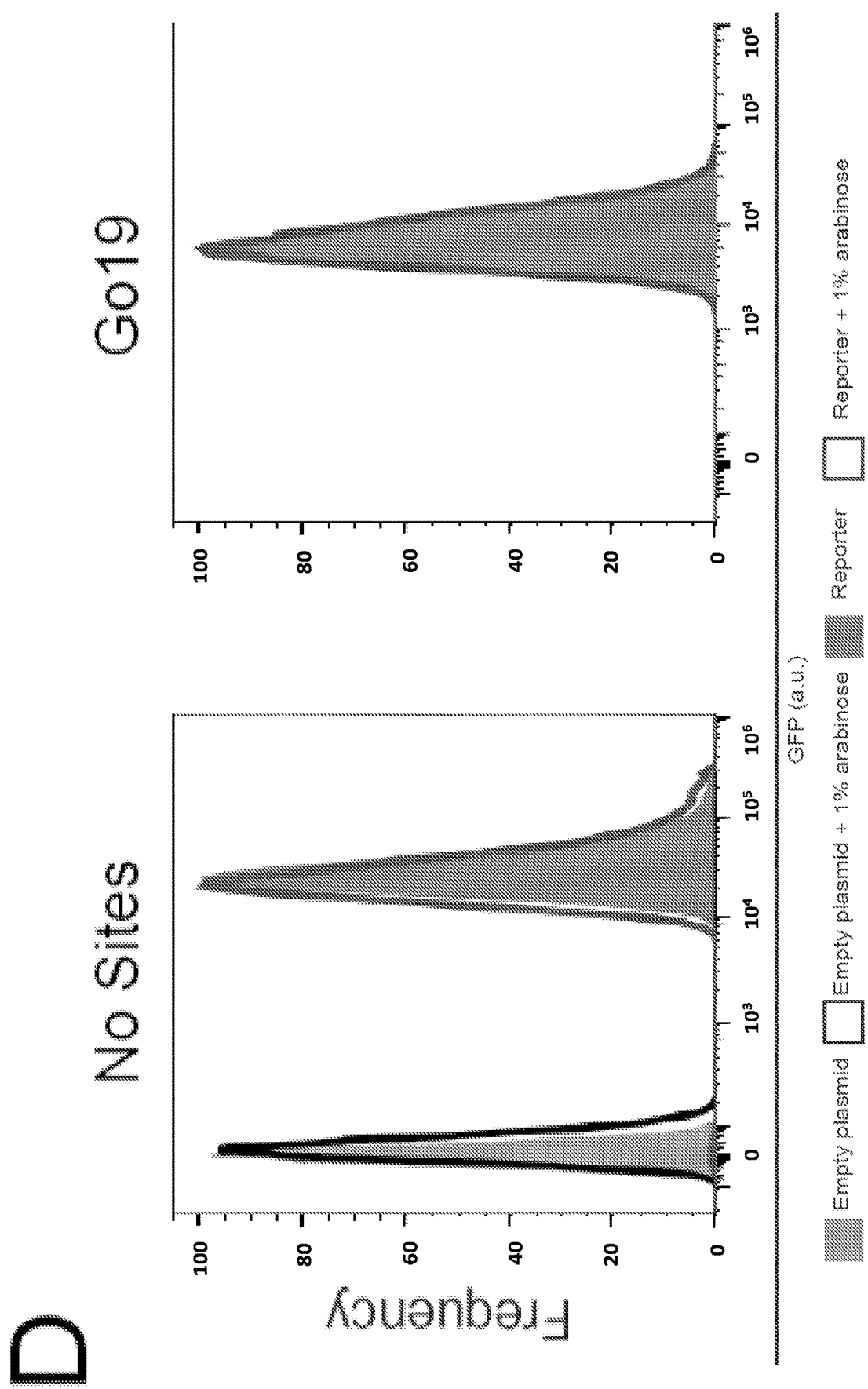
Figure 1:
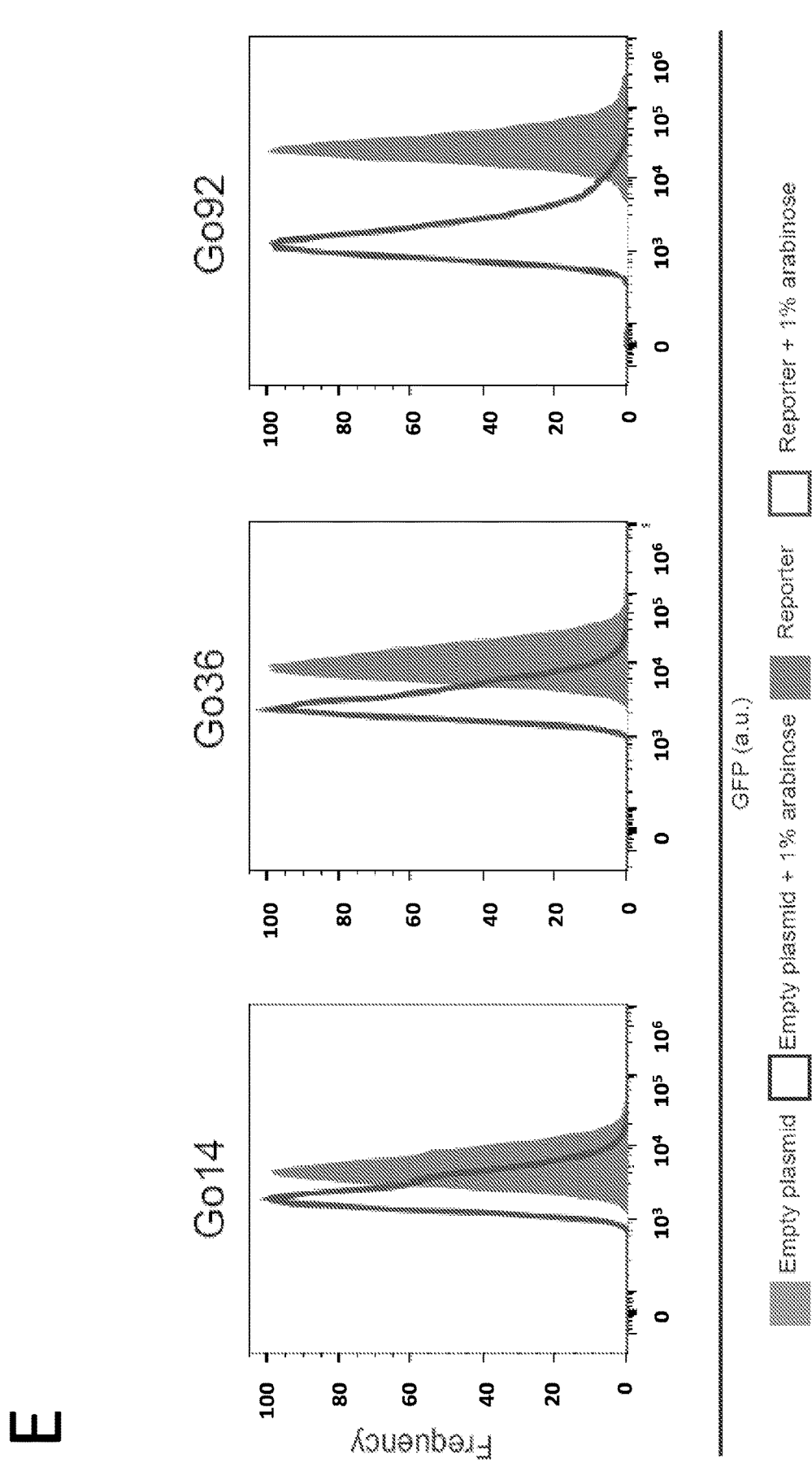

The present invention is described herein using several definitions, as set forth below and throughout the application.

Definitions

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The disclosed technology relates to "biosensors." As disclosed herein, a "biosensor" is a molecule or a system of molecules that can be used to bind to a ligand and provide a detectable response based on binding the ligand. In some cases, "biosensors" may be referred to as "molecular switches." Biosensors and molecular switches are disclosed in the art. (See, e.g., Ostermeier, Protein Eng. Des. Sel. 2005 August; 18(8):359-64; Wright et al., Curr. Opin. Chem. Biol. 2007 June; 11(3):342-6; Roberts, Chem. Biol. 2004 November; 11(11): 1475-6; and U.S. Pat. Nos. 8,771,679; 8,679,753; and 8,338,138; the contents of which are incorporated herein by reference in their entireties). Biosensors and molecular switches have been utilized in recombinant microorganisms. (See, e.g., Rogers et al., Curr. Opin. Biotechnol. 2016 Mar. 18; 42:84-91; and U.S. Published Application Nos. 2010/0242345 and 2013/0059295; the contents of which are incorporated herein by reference in their entireties). As indicated, many results have been published describing the utility of using naturally occurring biosensors for novel purposes, and applications include both high throughput screening and feedback-mediated enhanced production of various products via biosynthetic pathways. However, to the present inventors' knowledge, no one has published a bottom-up and generalizable strategy for converting metabolite-binding proteins into metabolite-responsive biosensors.

As used herein, the term "metabolite-binding protein" may be used interchangeably with the term "ligand-binding protein." As contemplated herein, a "ligand-binding protein" may include any protein that binds to a ligand. For example, a ligand-binding protein may include a receptor for a ligand. A ligand-binding protein may include an enzyme, and where the ligand-binding protein is an enzyme, the substrate for the enzyme may corresponds to the ligand as contemplated herein. As such, the term "ligand" may be used interchangeably herein with the term "substrate." A ligand-binding protein may include a periplasmic binding protein that binds a ligand or substrate. A ligand-binding protein may include a transporter that binds a ligand or substrate.

The systems, components, and methods disclosed herein may be utilized for sensing a ligand or a substrate or a metabolite in a cell or a reaction mixture. The disclosed systems, components, and methods typically include and/or utilize a fusion protein comprising a ligand-binding protein and a DNA-binding protein. The fusion protein of the disclosed systems and methods may otherwise be referred to as a "biosensor" as contemplated herein. The fusion proteins or biosensors disclosed herein bind the ligand of the ligand-binding protein and modulate expression of a reporter gene operably linked to a promoter that is engineered to include specific binding sites for the DNA-binding protein. The difference in expression of the reporter gene in the presence of the ligand versus expression of the reporter gene in the absence of the ligand can be correlated to the concentration of the ligand in a reaction mixture. As such, in some embodiments, the disclosed fusion proteins or biosensors may be referred to as metabolite-responsive transcription factors.

In some embodiments, the fusion protein or biosensor binds to the promoter that is engineered to include specific binding sites for the DNA-binding protein with an affinity ($K_{d1}$) in the absence of the ligand. When the ligand is present, the fusion protein or biosensor binds the ligand, and then the fusion protein has a second binding affinity ($K_{d2}$) for the promoter in the presence of the ligand. For example, the fusion protein or biosensor may bind the ligand and undergo a conformation change that alters the binding affinity of the fusion protein or biosensor for the promoter. In some embodiments of the disclosed systems $K_{d1}<K_{d2}$, and in other embodiments of the disclosed systems $K_{d1}>K_{d2}$. The difference in affinities in the presence and absence of the ligand may be based on a conformational change that the fusion protein exhibits in the presence of the ligand versus the absence of the ligand. The fusion protein or biosensor may modulate expression of the report gene based on whether the fusion protein or biosensor is bound to the promoter or the fusion protein or biosensor is not bound to the promoter, and the modulation may be correlated with the concentration of the ligand in the system.

As used herein, "modulating expression" may include "repressing expression" and/or "inhibiting expression," and "modulating expression may include "de-repressing expression" and/or "activating expression." As such, in some embodiments, when the fusion protein or biosensor is not bound to a ligand, the fusion protein or biosensor may repress expression and/or inhibit expression from a promoter that is engineered to include specific binding sites for the DNA-binding protein, and when the fusion protein or biosensor is bound to the ligand the fusion protein may de-repress and/or activate expression from the promoter. De-repression and/or activation of the expression of the reporter gene then can be correlated with the presence of the ligand. In other embodiments, when the fusion protein or biosensor is bound to a ligand, the fusion protein or biosensor may repress expression and/or inhibit expression from the promoter that is engineered to include specific binding sites for the DNA-binding protein, and when the fusion protein or biosensor is not bound to the ligand the fusion protein or biosensor may de-repress expression and/or activate expression from the promoter. A decrease in expression of the reporter gene then can be correlated with the presence of the ligand.

In some embodiments, when the fusion protein or biosensor is bound to the promoter engineered to include specific binding sites for the DNA-binding protein, the fusion protein may repress and/or inhibit expression of the report gene. Then, in the presence of the ligand for the ligand binding protein, the fusion protein or biosensor may bind the ligand and de-repress and/or activate expression of the reporter gene that is operably linked to the promoter. For example, in the presence of the ligand the fusion protein or biosensor may no longer bind to the promoter or may bind to the promoter with a lower affinity such that expression of the reporter gene is de-repressed and/or activated (i.e., $K_{d1}<K_{d2}$). In the absence of the ligand, the fusion protein or biosensor may undergo a conformational shift whereby the fusion protein or biosensor binds to the promoter or binds to the promoter with a higher affinity than in the presence of the ligand. De-repression and/or activation of the expression of the reporter gene then can be correlated with the presence of the ligand.

In other embodiments, when the fusion protein or biosensor is bound to the promoter engineered to include specific binding sites for the DNA-binding protein, the fusion protein or biosensor may activate expression of the reporter gene. Then, in the presence of the ligand for the ligand binding protein, the fusion protein or biosensor may bind the ligand and no longer activate expression of the reporter gene or may repress or inhibit expression of the reporter gene, effectively decreasing expression of the reporter gene. For example, in the presence of the ligand the fusion protein or biosensor may bind to the promoter with a higher affinity than in the absence of the ligand (i.e., $K_{d1}>K_{d2}$) and activate expression. In the absence of the ligand, the fusion protein or biosensor may undergo a conformational shift and may no longer bind the promoter or may bind the promoter with a lower affinity than in the presence of the ligand and no longer activate expression of the reporter gene. A decrease in expression of the reporter gene then can be correlated with the presence of the ligand.

The disclosed biosensors, systems, and methods may be utilized and/or performed using any suitable cell. Suitable cells may include prokaryotic cells and eukaryotic cells.

Reference is made herein to nucleic acid and nucleic acid sequences. The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

Reference also is made herein to peptides, polypeptides, proteins and compositions comprising peptides, polypeptides, and proteins. As used herein, a polypeptide and/or protein is defined as a polymer of amino acids, typically of length≥100 amino acids (Garrett & Grisham, Biochemistry, $2^{nd}$ edition, 1999, Brooks/Cole, 110). A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110).

As disclosed herein, exemplary peptides, polypeptides, proteins may comprise, consist essentially of, or consist of any reference amino acid sequence disclosed herein, or variants of the peptides, polypeptides, and proteins may comprise, consist essentially of, or consist of an amino acid sequence having at least about 80%, 90%, 95%, 96%, 97%, 98%, or 99% sequence identity to any amino acid sequence disclosed herein. Variant peptides, polypeptides, and proteins may include peptides, polypeptides, and proteins having one or more amino acid substitutions, deletions, additions and/or amino acid insertions relative to a reference peptide, polypeptide, or protein. Also disclosed are nucleic acid molecules that encode the disclosed peptides, polypeptides, and proteins (e.g., polynucleotides that encode any of the peptides, polypeptides, and proteins disclosed herein and variants thereof).

The term "amino acid," includes but is not limited to amino acids contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

The amino acid sequences contemplated herein may include conservative amino acid substitutions relative to a reference amino acid sequence. For example, a variant peptides, polypeptides, and proteins as contemplated herein may include conservative amino acid substitutions relative to an amino acid sequence of a reference peptide, polypeptide, or protein. "Conservative amino acid substitutions" are those substitutions that are predicted to interfere least with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

Table of Conservative Amino Acid Substitutions

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |

Table of Conservative Amino Acid Substitutions

| Original Residue | Conservative Substitution |
| --- | --- |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

"Non-conservative amino acid substitutions" are those substitutions that are predicted to interfere most with the properties of the reference peptide, polypeptide, or protein. For example, a non-conservative amino acid substitution might replace a basic amino acid at physiological pH such as Arg, His, or Lys, with a non-basic or acidic amino acid at physiological pH such as Asp or Glu. A non-conservative amino acid substitution might replace a non-polar amino acid at physiological pH such as Ala, Gly, Ile, Leu, Phe, or Val, with a polar amino acid at physiological pH such as Arg, Asp, Glu, His, or Lys.

The peptides, polypeptides, and proteins disclosed herein may be modified to include non-amino acid moieties. Modifications may include but are not limited to carboxylation (e.g., N-terminal carboxylation via addition of a di-carboxylic acid having 4-7 straight-chain or branched carbon atoms, such as glutaric acid, succinic acid, adipic acid, and 4,4-dimethylglutaric acid), amidation (e.g., C-terminal amidation via addition of an amide or substituted amide such as alkylamide or dialkylamide), PEGylation (e.g., N-terminal or C-terminal PEGylation via additional of polyethylene glycol), acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

Variants comprising deletions relative to a reference amino acid sequence or nucleotide sequence are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation or both of a reference polypeptide or a 5'-terminal or 3'-terminal truncation or both of a reference polynucleotide).

Variants comprising a fragment of a reference amino acid sequence or nucleotide sequence are contemplated herein. A "fragment" is a portion of an amino acid sequence or a nucleotide sequence which is identical in sequence to but shorter in length than the reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule, for example the N-terminal region and/or the C-terminal region of a polypeptide or the 5'-terminal region and/or the 3' terminal region of a polynucleotide. The term "at least a fragment" encompasses the full length polynucleotide or full length polypeptide.

Variants comprising insertions or additions relative to a reference sequence are contemplated herein. The words "insertion" and "addition" refer to changes in an amino acid or nucleotide sequence resulting in the addition of one or more amino acid residues or nucleotides. An insertion or addition may refer to 1, 2, 3, 4, 5, 10, 20, 30, 40, 50, 60, 70, 80, 90, 100, 150, or 200 amino acid residues or nucleotides.

Fusion proteins and fusion polynucleotides also are contemplated herein. A "fusion protein" refers to a protein formed by the fusion of at least one peptide, polypeptide, protein or variant thereof as disclosed herein to at least one molecule of a heterologous peptide, polypeptide, protein or variant thereof. The heterologous protein(s) may be fused at the N-terminus, the C-terminus, or both termini. A fusion protein comprises at least a fragment or variant of the heterologous protein(s) that are fused with one another, preferably by genetic fusion (i.e., the fusion protein is generated by translation of a nucleic acid in which a polynucleotide encoding all or a portion of a first heterologous protein is joined in-frame with a polynucleotide encoding all or a portion of a second heterologous protein). The heterologous protein(s), once part of the fusion protein, may each be referred to herein as a "portion", "region" or "moiety" of the fusion protein. For example, where the fusion protein comprises at least a portion of a ligand binding protein and at least a portion of a DNA-binding portion, the portions of the fusion may be referred to as "a ligand binding portion" and "a DNA-binding portion," respectively.

A fusion polynucleotide refers to the fusion of the nucleotide sequence of a first polynucleotide to the nucleotide sequence of a second heterologous polynucleotide (e.g., the 3' end of a first polynucleotide to a 5' end of the second polynucleotide). Where the first and second polynucleotides encode proteins, the fusion may be such that the encoded proteins are in-frame and results in a fusion protein. The first and second polynucleotide may be fused such that the first and second polynucleotide are operably linked (e.g., as a promoter and a gene expressed by the promoter as discussed below).

"Homology" refers to sequence similarity or, interchangeably, sequence identity, between two or more polypeptide sequences or polynucleotide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polypeptide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polypeptide.

A variant polypeptide may have substantially the same functional activity as a reference polypeptide. For example, a variant polypeptide may exhibit or more biological activities associated with binding a ligand and/or binding DNA at a specific binding site.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat.

No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Percent identity may be measured over the length of an entire defined polynucleotide sequence or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length may be used to describe a length over which percentage identity may be measured.

A "full length" polynucleotide sequence is one containing at least a translation initiation codon (e.g., methionine) followed by an open reading frame and a translation termination codon. A "full length" polynucleotide sequence encodes a "full length" polypeptide sequence.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polynucleotide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polynucleotide.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given polypeptide" and a "composition comprising a given polynucleotide" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

ILLUSTRATIVE EMBODIMENTS

The disclosed subject matter relates to metabolite-responsive transcription regulator biosensors. The following embodiments are illustrative and do not limit the scope of the claimed subject matter.

The disclosed subject matter may include systems and methods that comprise or utilize a biosensor. In some embodiments, the disclosed systems and methods comprises or utilize: (a) a fusion protein comprising a ligand-binding protein (LBP) and a DNA-binding protein (DBP) or portions or fragments thereof as described herein, the fusion protein comprising an amino acid sequence represented as: (N-terminal portion of the LBP)-(DBP)-(C-terminal portion of the LBP); and (b) a promoter which can be operably linked to a reporter gene. In the disclosed systems and methods, the promoter typically includes at least one heterologous binding site that is specific for the DBP and the fusion protein binds to the binding site and represses and/or inhibits transcription of the reporter gene in a cell or a reaction mixture when the ligand for the LBP is not present in the cell or the reaction mixture.

In the disclosed systems and methods, the fusion protein may bind to the promoter with an affinity ($K_{d1}$) in the absence of the ligand. When the ligand is present, the fusion protein preferably binds the ligand and the fusion protein then has a second binding affinity ($K_{d2}$) for the promoter in the presence of the ligand (or the fusion protein no longer binds the promoter). In some embodiments, the difference in affinities in the presence and absence of the ligand may be based on a conformational change that the fusion protein exhibits in the presence of the ligand versus the absence of the ligand.

Where $K_{d1}<K_{d2}$, transcription of the reporter gene may be de-repressed or activated in the presence of the ligand. In some embodiments, de-repression or activation in the presence of the ligand is proportional to the concentration of the ligand in the cell or the reaction mixture. In this embodiment, preferably the fusion protein binds to the promoter with a relatively high $K_{d1}$ in the absence of the ligand (e.g., with a $K_{d1}<$about 1 nM, 0.5 nM, 0.2 nM, 0.1 nM, 0.05 nM, 0.02 nM, 0.01 nM or lower). In this embodiment, preferably the fusion protein binds to the promoter with a relatively low $K_{d2}$ in the presence of ligand (e.g., with a $K_{d2}>$about 0.02 nM, 0.05 nM, 0.1 nM, 0.2 nM, 0.5 nM, 1 nM, 2 nM or higher). In this embodiment, preferably the ratio $K_{d2}:K_{d1}$ is at least about 5, 10, 20, 50, 100, 500, 1000 or more.

Where $K_{d1}>K_{d2}$, transcription of the reporter gene may be activated by the fusion protein when the fusion protein is bound to the ligand and expression may be no longer activated, repressed, or inhibited in the absence of the ligand, effectively decreasing expression in the absence of the ligand. In this embodiment, preferably the fusion protein binds to the promoter with a relatively high $K_{d1}$ in the presence of the ligand (e.g., with a $K_{d1}<$about 1 nM, 0.5 nM, 0.2 nM, 0.1 nM, 0.05 nM, 0.02 nM, 0.01 nM or lower). In this embodiment, preferably the fusion protein binds to the promoter with a relatively low $K_{d2}$ in the absence of ligand (e.g., with a $K_{d2}>$about 0.02 nM, 0.05 nM, 0.1 nM, 0.2 nM, 0.5 nM, 1 nM, 2 nM or higher). In this embodiment, preferably the ratio $K_{d1}:K_{d2}$ is at least about 5, 10, 20, 50, 100, 500, 1000 or more.

In the disclosed systems and methods, the fusion protein includes at least an N-terminal portion of the ligand-binding protein (LBP) fused at the N-terminus to at least a portion of the DNA-binding protein (DBP). In some embodiments, the fusion protein comprises an amino acid sequence of at least about 10, 20, 30, 40, 50, 60, 70, 80, 90, or 100 contiguous amino acids from the N-terminus of the LBP fused at the N-terminus to at least a portion of the DBP.

In the disclosed systems and methods, the fusion protein includes at least a C-terminal portion of the ligand-binding protein (LBP)-fused at the C-terminus to at least a portion of the DNA-binding protein (DBP). In some embodiments, the fusion protein comprises an amino acid sequence of at least about 10, 20, 30, 40, 50, 60, 70, 80, 90, or 100 contiguous amino acids from the C-terminus of the LBP fused at the C-terminus to at least a portion of the DBP.

In the disclosed systems and methods, the ligand-binding protein (LBP) binds to a ligand. In some embodiments of the systems and methods disclosed herein, the ligand is a cellular metabolite and the fusion protein and systems and methods disclosed herein may be utilized to detect and measure cellular metabolism. In some embodiments, the LBP is maltose binding protein and the ligand is maltose.

In the disclosed systems and methods, the fusion protein includes at least a portion of a DNA-binding protein (DBP). In some embodiments, the DBP comprises one or more DNA-binding domains selected from the group consisting of a zinc-finger protein (ZFP) DNA-binding domain, a transcription activator-like effector (TALE) DNA-binding domain, and a clustered regularly interspaced short palindromic repeat (CRISPR) DNA-binding domain. Suitable zinc-finger proteins may include, but are not limited to BCR-ABL1.

The disclosed systems and methods typically include or utilize a polynucleotide comprising a promoter, which may be operably linked to a reporter gene. The polynucleotide comprising a promoter, which may be operably linked to a reporter gene may be referred to as a reporter cassette. Suitable promoters include, but are not limited to, prokaryotic promoters. The promoter of the disclosed systems and methods typically is modified by inserting into the promoter a heterologous sequence that comprises one or more binding sites for the DNA-binding protein (DBP). In some embodiments, the promoter includes two, three, or more binding sites for the DBP. The binding sites are inserted in the promoter at positions such that when the DBP binds to the binding sites, the expression of a reporter gene that is operably linked to the promoter is repressed. In some embodiments, the binding sites are located at one or more positions in the promoter selected from: (i) between the −10 box (TATA box) and the −35 box (GC-rich region); (ii) adjacent to the −10 box or within 5 nucleotides of the −10 box; and/or (iii) adjacent to the −35 box or within 5 nucleotides of the −35 box.

The disclosed systems and methods may include or utilize a reporter gene that is operably linked to the promoter of the systems and methods, for example as part of a reporter cassette. Suitable reporter genes may provide a detectable signal when expressed (e.g., fluorescence of GFP) and/or may provide a selectable marker when expressed (e.g., a marker for anti-biotic resistance such as β-lactamase).

Also disclosed herein are methods for making and selecting components for use in the disclosed systems including methods for making and selecting biosensors or fusion proteins as discussed herein In some embodiments, the disclosed methods may be performed to prepare and select a fusion proteins comprising a ligand-binding protein (LBP) and a DNA-binding protein (DBP) or portions or fragments thereof as described herein, the fusion protein comprising an amino acid sequence represented as: (N-terminal portion of the LBP)-(DBP)-(C-terminal portion of the LBP). A library of fusion proteins may be prepared by inserting the DBP randomly into the LBP, for example, by performing a recombinant DNA method such as transposon-mediated recombination. One or more fusion proteins of the library then may be tested and selected for use as biosensors in the systems and methods disclosed herein. For example, the fusion proteins of the library may be tested for repressing transcription from a promoter that includes at least one heterologous binding site that is specific for the DBP, where the fusion protein binds to the binding site of the promoter and represses and/or inhibits transcription from the promoter when the ligand for the LBP is not present.

Applications for the disclosed technology include, but are not limited to: (i) novel sensing in which the novel metabolite-responsive biosensors enable real time monitoring of small molecules in living cells; (ii) high-throughput screening in which the novel metabolite-responsive biosensors can be used to rapidly screening very large $<10^8$ genetic libraries for high-producing strains; and (iii) dynamic feedback control in which the novel metabolite-responsive biosensors that regulate transcription can enable the engineering of feedback control to optimize production of product molecules via natural and/or engineered biosynthetic pathways.

Advantages of the disclosed technology include, but are not limited to: (i) the disclosed technology enables the use of biosensors to monitor the many metabolites not recognized by natural biosensors; (ii) the disclosed technology is generalizable in that the disclosed technology enables leveraging the wealth of naturally occurring metabolite-binding proteins into metabolite responsive transcriptional regulator proteins; (iii) the disclosed technology is broadly applicable because it utilizes modular DNA binding proteins, such as zinc finger proteins, such that novel biosensors can be easily programmed to regulate specific target genes; and (iv) the disclosed technology provides a library of zinc finger-responsive promoters, which we have built and characterized, that exhibit a range of response profiles, and as such, a user can predictably implement a desired biosensor-regulated function by pairing an engineered biosensor with a desired promoter design based upon the provided library.

In one embodiment, the present inventors developed a generalizable strategy for engineering novel metabolite-responsive transcriptional regulators. The inventors explored several strategies for converting a ligand-binding protein into a functioning biosensor, applied quantitative analysis to identify rules for designing biosensor-regulated promoters, and quantitatively characterized these novel biological parts. The inventor's systematic investigation guides the engineering of customized metabolite-responsive biosensors.

ILLUSTRATIVE EMBODIMENTS

The following embodiments are illustrative and should not be interpreted to limit the scope of the claimed subject matter.

Embodiment 1

A system comprising: (a) a fusion protein that functions as a biosensor, the fusion protein comprising a ligand-binding protein (LBP) and a DNA-binding protein (DBP), the fusion protein comprising an amino acid sequence represented as: (N-terminal portion of the LBP)-(DBP)-(C-terminal portion of the LBP); and (b) a promoter which can be operably linked to a reporter gene, wherein the promoter comprises at least one heterologous binding site that is specific for the DBP and the fusion protein binds to the ligand and modulates expression from the promoter.

Embodiment 2

The system of embodiment 1, wherein the fusion protein has a first binding affinity ($K_{d1}$) for the promoter in the absence of the ligand, and the fusion protein has a second binding affinity ($K_{d2}$) for the promoter in the presence of the ligand, such that $K_{d1} < K_{d2}$ and transcription of the reporter gene is de-repressed or activated in the presence of the ligand.

Embodiment 3

The system of embodiment 2, wherein de-repression or activation is proportional to concentration of the ligand in the system.

Embodiment 4

The system of embodiment 2 or 3, wherein $K_{d1}$ is <about 1 nM, 0.5 nM, 0.2 nM, 0.1 nM, 0.05 nM, 0.02 nM, 0.01 nM or lower.

Embodiment 5

The system of any of embodiments 2-4, wherein $K_{d2}$ is >about 0.02 nM, 0.05 nM, 0.1 nM, 0.2 nM, 0.5 nM, 1 nM, 2 nM or higher.

Embodiment 6

The system of any of embodiments 2-5, wherein the ratio $K_{d2}:K_{d1}$ is at least about 5, 10, 20, 50, 100, 500, 1000 or more.

Embodiment 7

The system of embodiment 1, wherein the fusion protein has a first binding affinity ($K_{d1}$) for the promoter in the absence of the ligand, and the fusion protein has a second binding affinity ($K_{d2}$) for the promoter in the presence of the ligand, such that $K_{d1} > K_{d2}$ and transcription of the reporter gene is repressed or de-activated in the presence of the ligand.

Embodiment 8

The system of embodiment 7, wherein repression or de-activation is proportional to concentration of the ligand in the system.

Embodiment 9

The system of embodiment 7 or 8, wherein $K_{d2}$ is <about 1 nM, 0.5 nM, 0.2 nM, 0.1 nM, 0.05 nM, 0.02 nM, 0.01 nM or lower.

Embodiment 10

The system of any of embodiments 7-9, wherein $K_{d1}$ is >about 0.02 nM, 0.05 nM, 0.1 nM, 0.2 nM, 0.5 nM, 1 nM, 2 nM or higher.

Embodiment 11

The system of any of embodiments 7-10, wherein the ratio $K_{d1}:K_{d2}$ is at least about 5, 10, 20, 50, 100, 500, 1000 or more.

Embodiment 12

The system of any of the foregoing embodiments, wherein the N-terminal portion of the LBP within the fusion protein comprises an amino acid sequence of at least about 10, 20, 30, 40, 50, 60, 70, 80, 90, or 100 contiguous amino acids from the N-terminus of the LBP.

Embodiment 13

The system of any of the foregoing embodiments, wherein the C-terminal portion of the LBP within the fusion protein comprises an amino acid sequence of at least about 10, 20, 30, 40, 50, 60, 70, 80, 90, or 100 contiguous amino acids from the C-terminus of the LBP.

Embodiment 14

The system of any of the foregoing embodiments, wherein the ligand is a cellular metabolite.

Embodiment 15

The system of any of the foregoing embodiments, wherein the LBP is maltose binding protein.

Embodiment 16

The system of any of the foregoing embodiments, wherein the DBP comprises one or more DNA-binding domains selected from the group consisting of a zinc-finger protein (ZFP) DNA-binding domain, a transcription activator-like effector (TALE) DNA-binding domain, and a clustered regularly interspaced short palindromic repeat (CRISPR) DNA-binding domain.

Embodiment 17

The system of embodiment 16, wherein the ZFP is BCR-ABL1.

Embodiment 18

The system of any of the foregoing embodiments, wherein the promoter is a prokaryotic promoter.

Embodiment 19

The system of embodiment 18, wherein the promoter comprises two or more binding sites for the DBP.

Embodiment 20

The system of embodiment 19, wherein the binding sites are located at one or more positions selected from: (i) between the −10 box (TATA box) and the −35 box (GC-rich region); (ii) adjacent to the −10 box (TATA box) or within 5 nucleotides of the −10 box (TATA box); and (iii) adjacent to the −35 box (GC-rich region) or within 5 nucleotide of the −35 box (GC-rich region).

Embodiment 21

A method for preparing a fusion protein for use as a biosensor, the fusion protein comprising a ligand-binding protein (LBP) and a DNA-binding protein (DBP) or portions or fragments thereof, where the fusion protein comprises an amino acid sequence represented as (N-terminal portion of the LBP)-(DBP)-(C-terminal portion of the LBP), the method comprising preparing a library of fusion proteins by inserting the DBP randomly into the amino acid sequence of the LBP via performing a recombinant DNA method, and selecting a fusion protein from the library of fusion proteins as a biosensor.

Embodiment 22

The method of embodiment 21, wherein the recombinant DNA method is transposon-mediated DNA recombination.

Embodiment 23

The method of embodiment 21, wherein the fusion protein is selected as a biosensor via testing whether the fusion protein modulates transcription from a promoter comprising a binding site for the DBP of the fusion protein in the presence or absence of the ligand for the LBP of the fusion protein.

EXAMPLES

The following Examples are illustrative and are not intended to limit the scope of the claimed subject matter.

Example 1

Reference is made to Younger et al., "Engineering novel modular biosensors to confer metabolite-responsive regulation of transcription," ACS Synth. Biol. 2017 Feb. 17; 6(2):311-325, the content of which is incorporated herein by reference in its entirety.

Title: Engineering Modular Biosensors to Confer Metabolite-Responsive Regulation of Transcription

Abstract

Efforts to engineer microbial factories have benefitted from mining biological diversity and high throughput synthesis of novel enzymatic pathways, yet screening and optimizing metabolic pathways remain rate-limiting steps. Metabolite-responsive biosensors may help to address these persistent challenges by enabling the monitoring of metabolite levels in individual cells and metabolite-responsive feedback control. We are currently limited to naturally-evolved biosensors, which are insufficient for monitoring many metabolites of interest. Thus, a method for engineering novel biosensors would be powerful, yet we lack a generalizable approach that enables the construction of a wide range of biosensors. As a step towards this goal, we here explore several strategies for converting a metabolite-binding protein into a metabolite-responsive transcriptional regulator. By pairing a modular protein design approach with a library of synthetic promoters and applying robust statistical analyses, we identified strategies for engineering biosensor-regulated bacterial promoters and for achieving design-driven improvements of biosensor performance. We demonstrated the feasibility of this strategy by fusing a programmable DNA binding motif (zinc finger module) with a model ligand binding protein (maltose binding protein), to generate a novel biosensor conferring maltose-regulated gene expression. This systematic investigation provides insights that may guide the development of additional novel biosensors for diverse synthetic biology applications.

Introduction

Cells evaluate and respond to their internal states through a range of mechanisms, including the wide use of molecular biosensors. In a general sense, a biosensor may be understood to comprise a species that senses one or more analytes, typically through a molecular recognition event involving binding to the analyte, such that recognition of the analyte is transduced into a change in the biosensor that enables it to effect a change in cell state. Biosensors may be composed of a range of biomolecules, most commonly including RNA[1-3] or protein[4-15]. Early applications included the generation of whole-cell biosensors, in which an environmental analyte enters a cell through active or passive transport. Upon recognition of the analyte by an intracellular biosensor, an output signal such as fluorescence, luminescence, or color-change is generated, most commonly by biosensor-induced expression of a reporter gene or by analyte binding-induced changes in the activity of a fluorescent or enzymatic biosensor protein. A particularly exciting frontier is the use of biosensors to sense not external factors, but rather a cell's internal metabolic state.

Metabolite-responsive biosensors may help to address several pervasive and persistent challenges in the fields of synthetic biology and metabolic engineering[3-7, 9, 11, 13-16]. First, biosensors may help overcome the costliest and rate-limiting step in the development of new biosynthetic pathways—screening and evaluating pathway or strain variants to both identify well-performing constructs and glean insights into pathway function that may be utilized in subsequent iterative rounds of the design-build-test engineering cycle. By coupling metabolite-binding to outputs such as fluorescence or antibiotic resistance, biosensors can enable the screening of large libraries (e.g., >$10^8$ members), which remain beyond the capacity of even contemporary automated platforms for performing clonal evaluations. For example, the naturally occurring transcription factor BmoR was harnessed to confer growth in the presence of butanol, which enabled the screening of a plasmid library to identify strains exhibiting robust production of 1-butanol[6]. Similar approaches have been harnessed to screen plasmid libraries to achieve enhanced production of mevalonate[17], triacetic acid lactone[18], and L-lysine[19]. Such an approach may be extended to screen for high-performing variants generated through genomic mutation, including both random mutagenesis, which has been utilized to optimize L-lysine production via mutation of endogenous enzymes[20], and targeted genome-wide mutagenesis, which has been used to optimize naringenin and glucaric acid production via combinatorial perturbation of endogenous gene regulation[4]. While most investigations to date have applied these methods to bacterial chasses, such approaches may also be extended to yeast and other organisms[9]. In general, "digital" biosensor outputs, such as expression of antibiotic resistance, are most useful for screening, while "analog" biosensor outputs, such as fluorescence, enable both screening and characterization of internal metabolite concentrations, potentially at the single-cell level, to guide construct analysis and iterative refinement.

A powerful, yet less explored extension of this approach is the use of metabolite-responsive transcriptional regulators to implement feedback control in order to optimize system performance. An early demonstration of this opportunity was the use of an acetyl phosphate biosensor to sense excess glycolytic flux, and in response, regulate the expression of limiting genes in the lycopene biosynthesis pathway. This activity resulted in both enhanced lycopene production and diminished growth defects[16]. More recently, feedback control was used to achieve balanced flux through several pathways that led to enhanced yields and improved cell survival during the production of a biofuel (fatty acid ethyl ester)[7]. This investigation made use of the natural FadR biosensor, which is antagonized by Acyl-CoA, paired with synthetic promoters engineered to achieve robust regulation by FadR. Similarly, lysine-responsive riboswitches were utilized to control the expression of citrate synthase and thereby increase lysine production by controlling flux in the TCA cycle[3]. The potential utility of biosensor-mediated feedback control is now widely recognized[11, 21, 22], and further implementation is currently limited largely by the pool of suitable biosensors.

A general challenge in the use of biosensors is that the pool of metabolites one would like to measure and potentially utilize for feedback control is much larger than the pool of metabolite-responsive transcriptional regulators that have been identified. Bioinformatic approaches and surveys of published literature may identify a number of useful biosensors that have simply not yet been utilized as such. For example, a recent study elegantly applied a systematic characterization of known metabolite-responsive transcriptional regulators to generate quantitative fingerprints enabling these biological "parts" to be harnessed for engineering applications[5]. However, since the entire pool of naturally-evolved biosensors is likely much smaller than the pool of metabolite targets, it would be attractive to develop approaches for engineering novel biosensors. Ideally, such a biosensor could be constructed to recognize an analyte of interest (with some practical degree of specificity), would exhibit a dynamic range suitable (or tunable) to the application of interest, and could be directed to regulate a gene (or genes) of interest in a ligand-dependent fashion. Although this comprises a daunting protein engineering challenge, a number of smaller-scale successes suggest strategies that may help to achieve this goal.

The most widely used approach for engineering novel biosensors is to genetically fuse a ligand-binding protein with a distinct functional domain, such that the fusion causes the activity of the functional domain to be conditional upon the presence or absence of the ligand of interest[10, 23-29]. Most commonly, the functional domain comprises a fluorescent protein or enzyme conferring antibiotic resistance, each of which comprises an output amenable to screening the large libraries required to identify functional fusion proteins. For example, maltose binding protein (MBP) and β-lactamase (BLA) were circularly permutated to generate a library of fusion proteins, such that successful fusions exhibited high BLA activity only in the presence of maltose[24]. Calmodulin, which experiences a conformational change upon binding to $Ca^{2+}$, is similarly amenable to such a fusion strategy to create fusion proteins based upon BLA[26] or GFP and its derivatives[30]. Indeed, many similar approaches have harnessed proteins in which ligand binding induces a conformational change in order to generate biosensors in which fluorescence, often via FRET, provides a metric of intracellular metabolite concentration (reviewed in[10, 31-33]). Furthermore, zinc finger proteins (ZFP), transcription activator-like effectors (TALE), and CRISPR-based DNA binding domains have been fused to putative repressor and activator domains to create novel transcription factors to regulate both prokaryotic and eukaryotic transcription, although such functions are not generally regulated by ligand binding to the transcription factor ([34-39]). However, recently an allosterically regulated version of Cas9 has been developed by fusing the estrogen receptor-α to create a protein that represses transcription in the presence of the ligand, 4-hydroxytamoxifen[40]. Given the broad homology within the LacI/GalR family of ligand-responsive transcription factors, novel biosensors have also been constructed by fusing the ligand-binding domains from LacI paralogs to the LacI DNA binding domain, conferring regulation of the lac promoter by fructose, ribose, or other species[17, 18, 41, 42]. Ultimately, computational protein design could guide the development of novel biosensors. To date, such methods have been used primarily to shift ligand specificity of existing biosensor proteins[17, 43-47], although de novo design of novel ligand-binding proteins and biosensors is another promising frontier[48, 49] Overall, these approaches bespeak the promise of engineering novel biosensor proteins, but to date no generalizable approach for engineering novel metabolite-responsive transcriptional regulators has been described.

In this study, we investigated, validated, and developed a strategy for engineering novel metabolite-responsive transcriptional regulators. Our central goals were to quantitatively evaluate several strategies for converting a ligand-binding protein into a functioning biosensor that regulates transcription, and to elucidate design principles governing the performance of biosensors constructed in such a fashion. To this end, we leveraged the facts that MBP is a well-characterized ligand-binding protein, and that zinc finger proteins (ZFP) are well-characterized and programmable DNA binding domains. Furthermore, we applied quantitative analyses to identify rules for designing biosensor-regulated promoters and quantitatively characterize these new biological parts. This systematic investigation establishes a foundation for applying a potentially generalizable strategy towards the ultimate goal of engineering customized metabolite-responsive bio sensors.

Results

Developing Novel Zinc Finger Protein-Regulated Constitutive Promoters.

In this investigation, we sought to develop a readily generalizable strategy for engineering novel biosensor proteins from the ground up. We hypothesized that such a goal might be achieved by first using an orthogonal DNA binding protein to regulate transcription of an engineered promoter, and then fusing this DNA binding domain to a distinct protein capable of binding the target ligand, such that when the fusion protein binds ligand, DNA binding (and thus transcriptional regulation) is either disrupted or enhanced.

To begin investigating this overall strategy, we first sought to engineer a novel transcriptional regulator by leveraging the modular, programmable DNA binding properties conferred by the zinc finger protein (ZFP) architecture[50-52]. ZFPs are small (compared to alternative architectures such as TALEs[38, 39]), easy to manipulate, and can be designed to bind to nearly any sequence. The ZFP architecture has previously been utilized to create novel transcription factors in $E.\ coli$[36], as well as in eukaryotes[34, 35, 53]. The $Cys_2$-$His_2$ class of ZFPs is an attractive DNA binding domain, since each "finger" of the ZFP binds to a distinct 3 bp DNA sequence (FIG. 1A)[54], and thus sequence specific binding is achieved by engineering ZFPs comprising multiple "fingers" fused in tandem. Therefore, to initially investigate our strategy for biosensor engineering, we utilized the BCR-ABL1 ZFP as our DNA binding domain. BCR-ABL1 is well-characterized, exhibits a low equilibrium dissociation constant when binding its cognate 9 bp DNA binding site with three tandem fingers ($K_d$~78 µM), and has been shown to exhibit conditional DNA binding when genetically split and reconstituted[50, 55]. Notably, although the BCR-ABL1 consensus binding sequence is known, no $E.\ coli$ promoters have been previously repressed by BCR-ABL1.

In order to begin elucidating the rules for building novel ZFP-regulatable promoters, a library of 68 different constitutive promoters was designed (FIG. 7). The library was built by inserting BCR-ABL1 binding site(s) at various locations around the consensus –10 box (TATAAT) and –35 region (TTGACA). The –10 box and –35 region are critical for recruitment of the $\sigma^{70}$ factor of RNA polymerase, and these sequences are necessary and sufficient to create a constitutive promoter[56, 57] Design features that varied across the library included BCR-ABL1 binding site location(s), relative to the consensus elements, and spacing between BCR-ABL1 binding sites. Although this design did not presuppose that ZFP-binding would repress transcription from these constitutive promoters, this was the anticipated mechanism because BCR-ABL1 was not fused to a trans-activation domain[36]. Each promoter was encoded on a low copy number plasmid and drove expression of $E.\ coli$-optimized GFP as a reporter.

Figure 8:
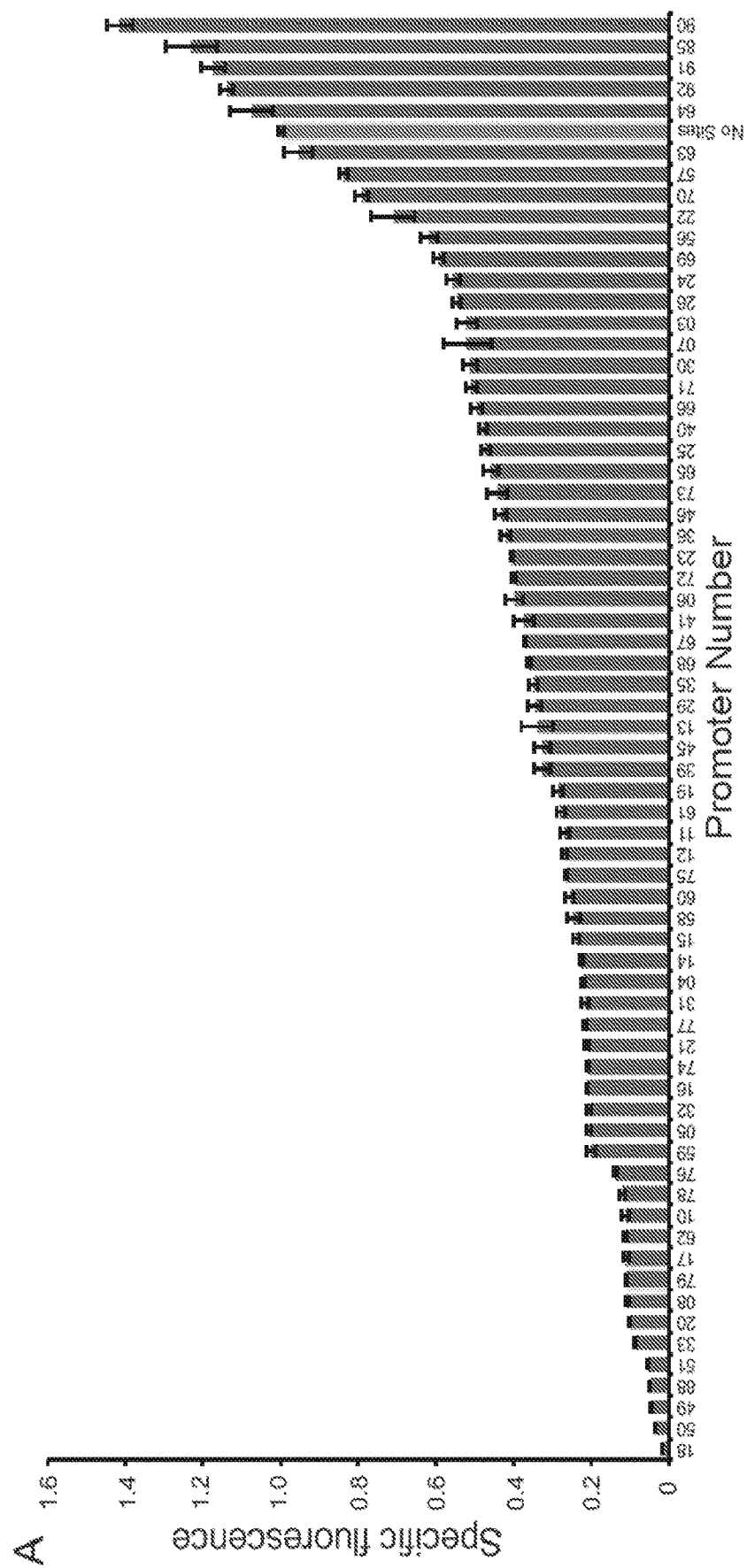
FIG. 8. Specific fluorescence variation across the promoter library. (A) The impact of BCR-ABL1 expression on GFP reporter output was evaluated using a library of promoters bearing BCR-ABL1 sites at various locations in the promoter. The specific fluorescence (GFP fluorescence per $OD_{600}$) was measured for each promoter in the library in the absence of BCR-ABL1 and normalized to that of the No Sites control promoter. (B) Comparison of specific fluorescence without BCR-ABL1 to BCR-ABL1-mediated repressibility (relative expression); note that each quantity was normalized to value associated with the No Sites control promoter. Relative expression is defined as the ratio of $GFP/OD_{600}$ (for any given promoter) of the induced case relative to that of the uninduced case, divided by this same ratio for the No Sites promoter (a full description and rationale can be found in the Materials and Methods section of the main manuscript). All experiments were run in biological triplicate, and error bars indicate one standard deviation.
Figure 8:
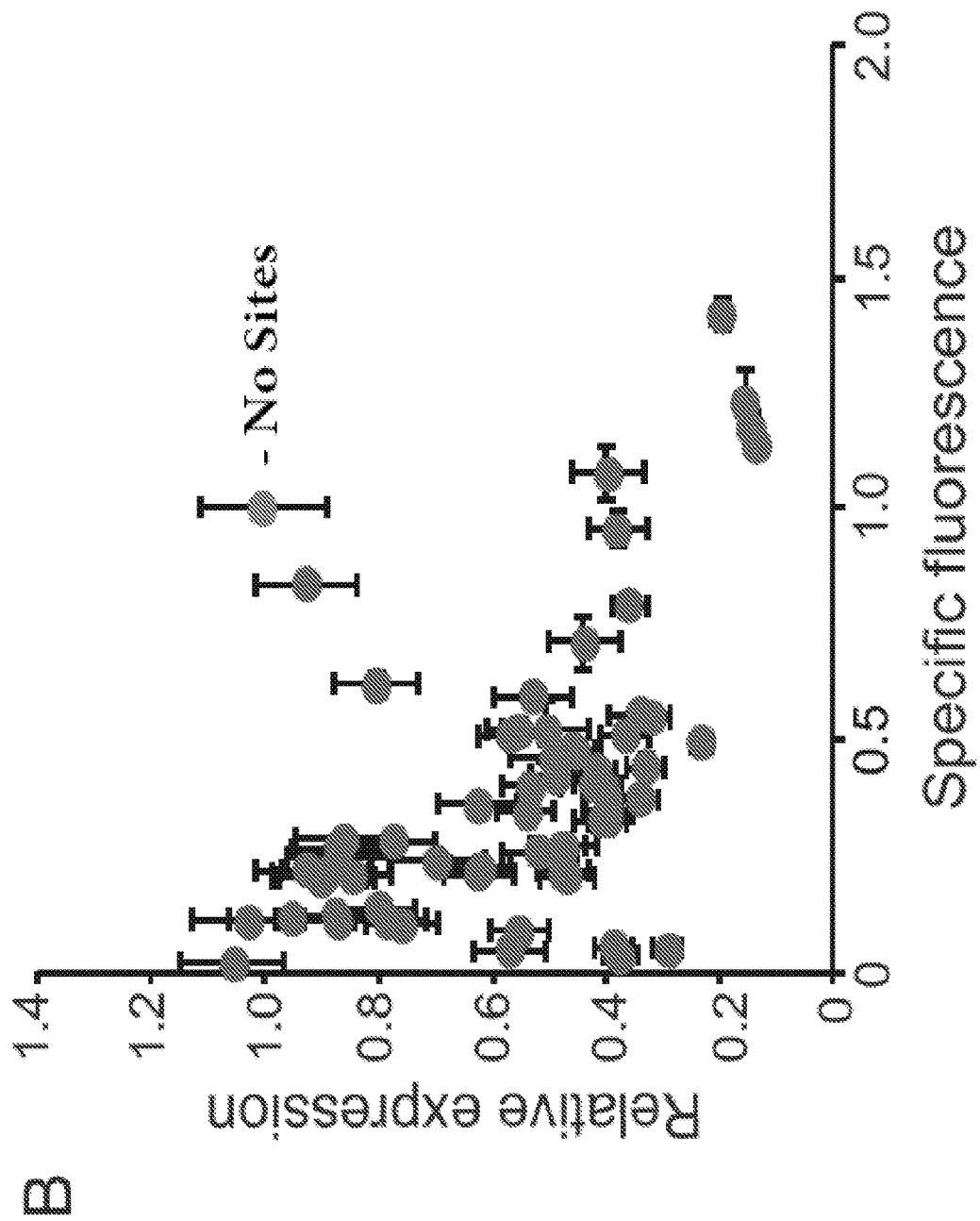
Figure 9:
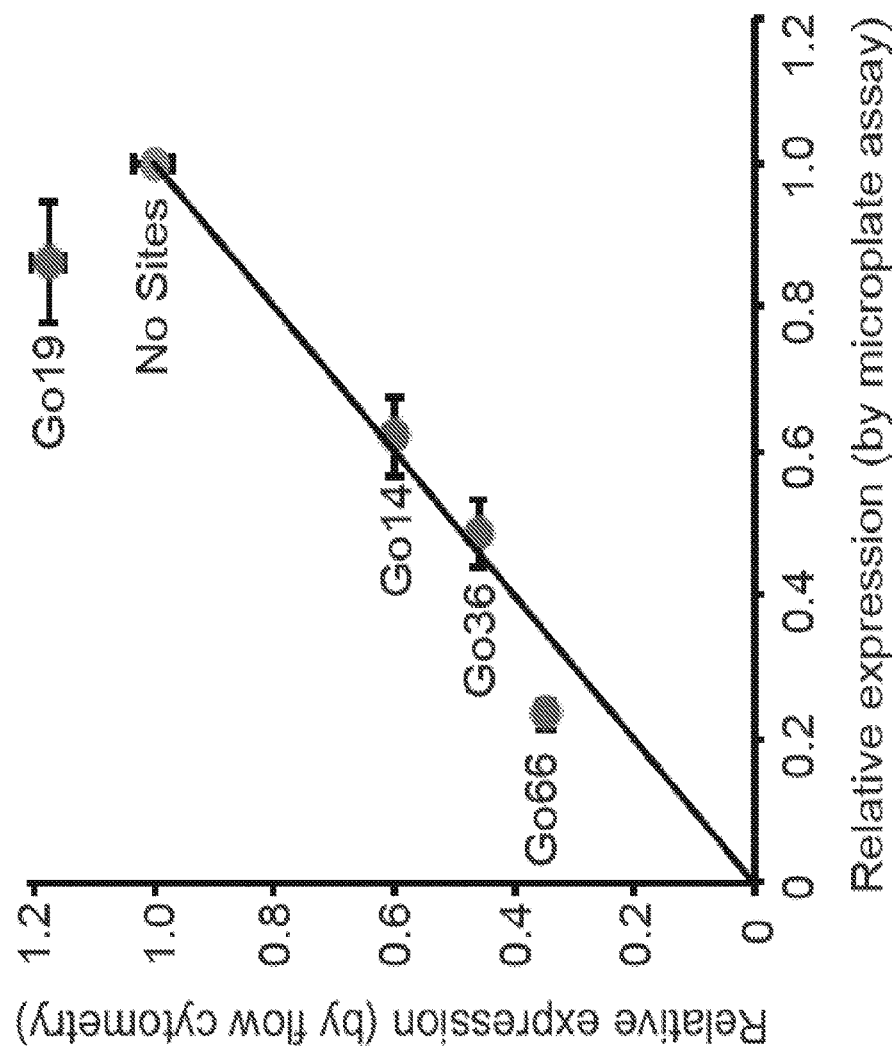
FIG. 9. Comparison of flow cytometry and microplate assay-based quantification of BCR-ABL1-mediated repressibility. Select promoter constructs were analyzed by both methods. Close association of each point with the diagonal line (y=x) drawn as a visual guide indicates agreement between the two methods of quantifying relative expression, with the possible exception of Go19, which was the least repressible promoter analyzed. All samples were normalized to the No Sites control promoter. Experiments were conducted in biological triplicate, and error bars indicate one standard deviation.

To quantify the extent to which each promoter was repressed or activated by BCR-ABL1 during exponential growth, we defined a metric of "relative expression" that describes how induction of BCR-ABL1 expression impacts expression from the promoter as compared to a "No Sites" control promoter lacking BCR-ABL1 binding sites (see Material and Methods). This relative expression normalization strategy was utilized in order to implicitly correct for any effects that arabinose many confer on GFP/$OD_{600}$ in a manner unrelated to expression of the ZFP. Thus, low relative expression indicates that a promoter is highly repressed by BCR-ABL1. The library of promoters exhibited wide ranges of basal expression (FIG. 8) and repressibility by BCR-ABL1 (FIG. 1B). Nearly all of the promoters exhibited a decrease in GFP expression upon the induction of the BCR-ABL1 ZFP, and no promoters showed any level of activation upon BCR-ABL1 induction. When relative expression was quantified at 10 h post-induction, at which point cultures had reached stationary phase, the observed repressibility was much more pronounced (FIG. 1C). To investigate how relative expression patterns differed between cells within each population, we also examined several representative promoter cases at the single cell level using flow cytometry (FIG. 1D). Overall, responses were unimodal, such that population-averaged fluorescence measured by flow cytometry corresponded well to comparable metrics obtained by microplate-based assays (FIG. 9), and thus the latter method was used for subsequent analyses. Given this wide range of phenotypes, we next investigated the relationship between promoter design and repressibility.

Figure 2:
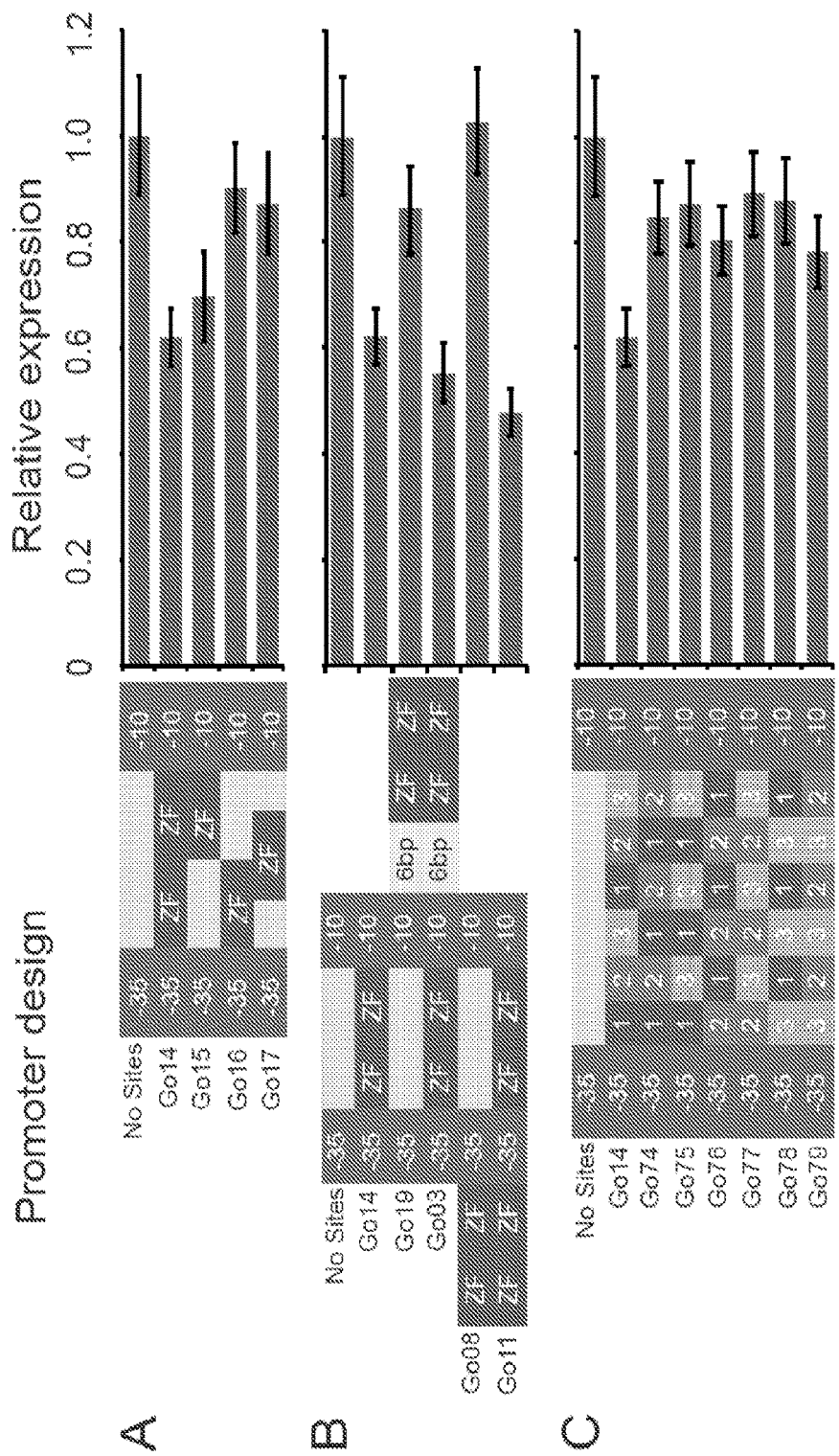
FIG. 2. Inspection-based evaluation of promoter design rules. Promoters were manually grouped to represent exploration of design features including (A) presence and location of ZFP binding sites between the −10 box and −35 region, (B) combinatorial effects of having a pair of binding sites between the −10 box and −35 region, (C) variations in the locations of individual ZFP binding sites within the core, (D, E) contributions of additional BCR-ABL1 binding sites either downstream or upstream of the −10 box and −35 region, (F) spacing between the −10 box and the downstream ZFP binding sites, (G) combinatorial effects of directly flanking the −10 box and −35 region with ZFP binding sites. All data are re-plotted from FIG. 1B. Abbreviations and conventions: ZF is the 9 bp BCR-ABL1 binding site; 1, 2, and 3 represent the first, second, or third, 3 bp finger binding sites within the BCR-ABL1 binding site; boxes represent spacer sequences of the indicated length (1, 2, 3, 4, 5, or 6 bp). Microplate data were collected over 7 sequential time points, spanning ~1.5 h of mid-exponential phase growth, and averaged. All data represent mean values calculated from three independent experiments, and error bars represent one standard deviation.
Figure 2:
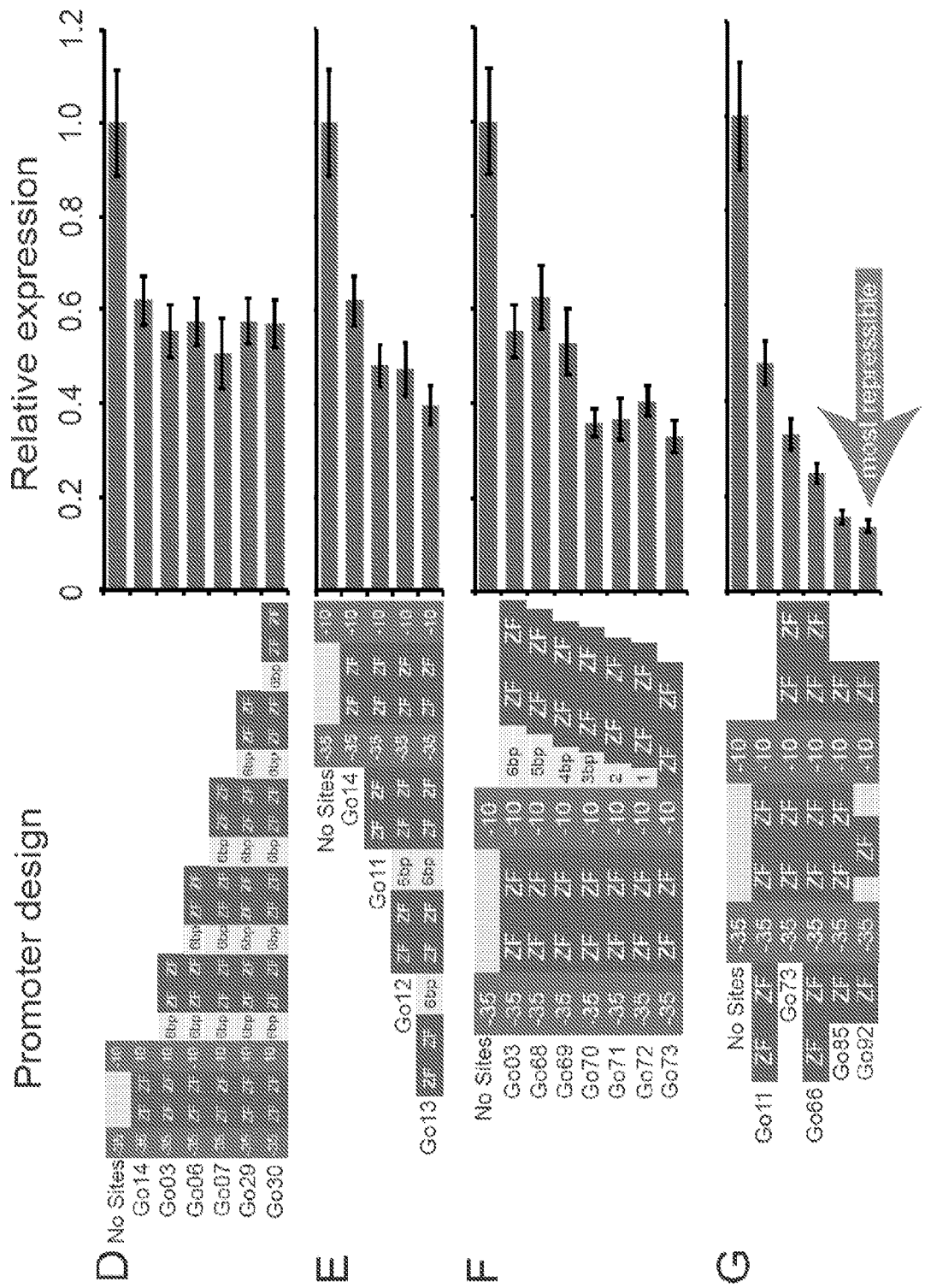

We first examined the impact of promoter design on repressibility by inspection. As depicted in FIG. 2, promoters representing variations on a particular design feature were first grouped together in order to identify simple trends, with the caveat that such trends are potentially restricted to the scope of promoters evaluated in our library. Generally, placing two ZFP binding sites in between the –10 box and the –35 region (the promoter "core") led to greater repressibility than did insertion of a single ZFP binding site, regardless of its position (FIG. 2A). Go15 is an exception to this trend, as it was not dramatically less repressible than was Go14. Furthermore, promoters with two ZFP binding sites in the core were more repressible than were comparable promoters that lacked these core sites but shared other ZFP binding sites (FIG. 2B). Compared to promoters including all three ZFP binding sites required for recognition by BCR-ABL1, promoters in which only two sites were present exhibited reduced repressibility by BCR-ABL1 (FIG. 2C). Adding additional ZFP binding sites downstream of the –10 box did not increase repressibility (FIG. 2D). However, adding additional binding sites upstream of the –35 box did effectively increase repressibility (FIG. 2E). Decreasing the spacer distance between the –10 box and the first downstream binding site increased repressibility (FIG. 2F). Similarly, removing any spacer between the ZFP binding sites and the –10 box and –35 region resulted in greater repressibility than did removing spacers adjacent to either the –10 box or –35 region alone (FIG. 2G). To explain the increase in repressibility observed for Go85 compared to Go66, we hypothesize that BCR-ABL1 cannot simultaneously occupy adjacent binding sites, and furthermore, that binding to the sites directly upstream of the –10 box and downstream of the –35 region results in greater repressibility than is conferred by BCR-ABL1 binding to the more distal binding sites present in Go66. Altogether, promoter Go92 exhibited the greatest repressibility of any library member, and this promoter appears to follow many of the design rules suggested by the above inspection-based analysis. However, since only a subset of our promoter library was amenable to this direct inspection-based analysis, we next pursued a systematic analysis of the entire library to further refine our understanding of the applicable design rules.

Computational Identification of Promoter Design Features Conferring ZFP-Mediated Repression.

Figure 3:
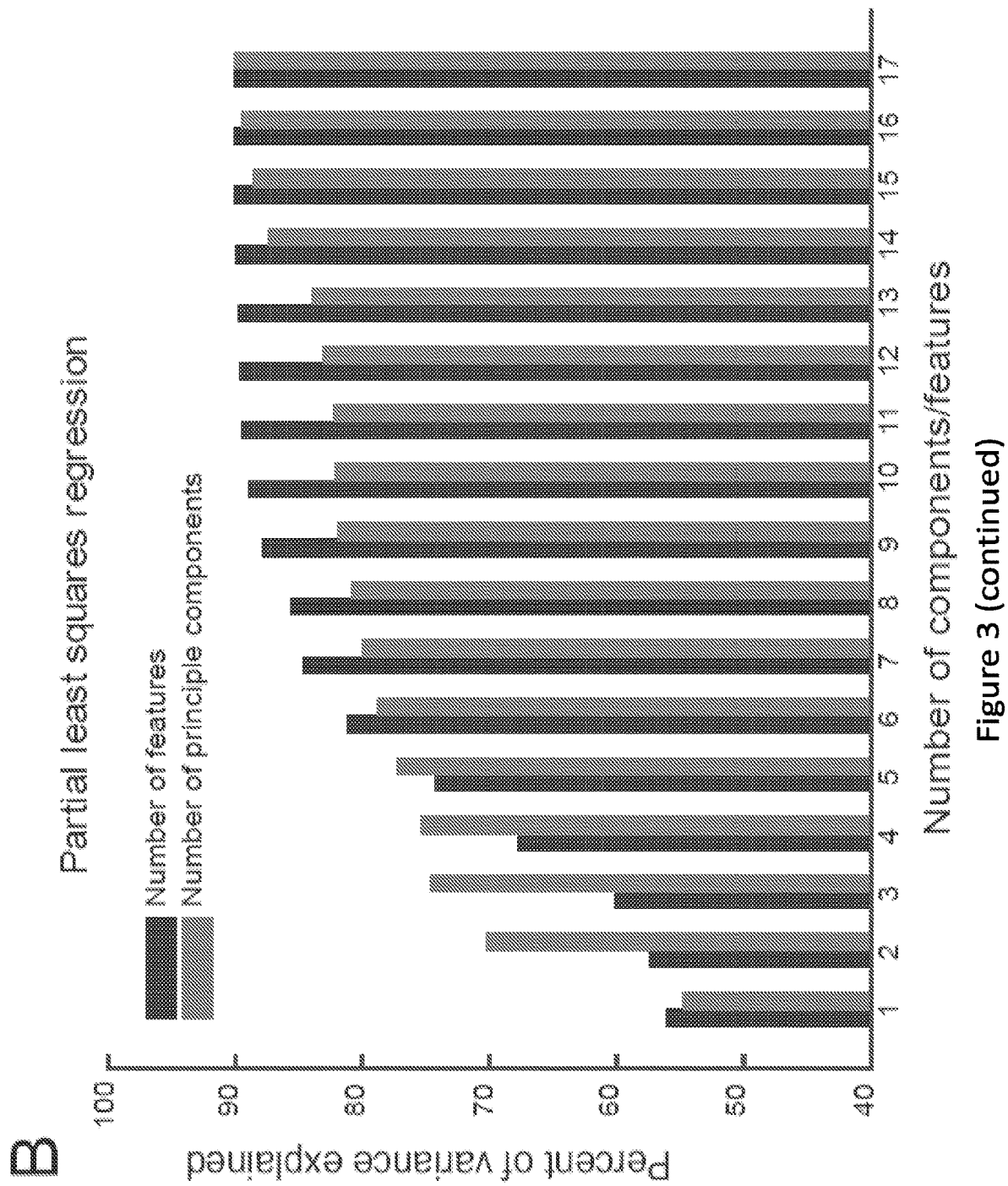
FIG. 3. Computational identification of promoter design features conferring ZFP-mediated repressibility (A) Shorthand names and descriptions of the 17 features chosen to describe the promoter library. One binding site is defined as the nine base pair ZFP binding site. One pair is defined as two adjacent binding site sequences. (B) PLSR analysis of the degree to which promoter features explain variance in the relative expression data (BCR-ABL-mediated repressibility) reported in FIG. 1. Each series evaluates the explanatory power achieved using an increasing number of features or principle components, each of which is added to the set in ranked order from most to least important. (C) Lasso regression analysis of the degree to which promoter features explain variance in the relative expression data reported in FIG. 1. This plot displays the number of features with non-zero coefficients (and the resulting mean squared error) as $\lambda$ is increased, causing less important features to be eliminated from the regression analysis. The mean squared error was obtained through 10-fold cross validation, which also produced a standard error for the mean squared error, which is shown as error bars. (D) Relative importance of each feature, vis-à-vis explaining BCR-ABL1-mediated repressibility as determined by PLSR, Random Forest, and Lasso regression, with the overall order listed here determined by average rank across the three feature selection methods. (+)-positive coefficients (large feature values confer more repressibility); and (−) negative coefficients (small feature values confer more repressibility). Detailed regression coefficients and importance values are provided in FIG. 10.
Figure 3:
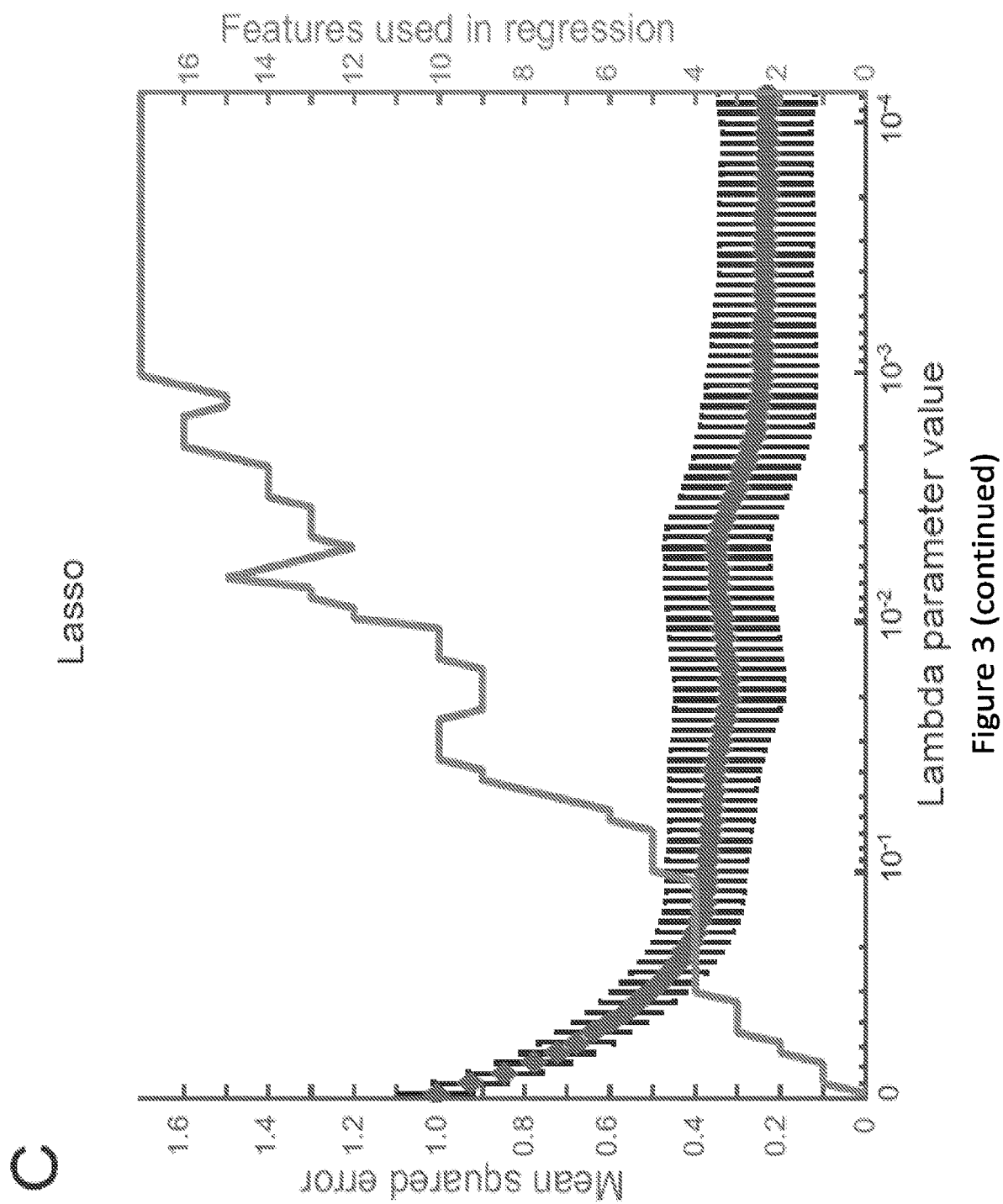
Figure 3:
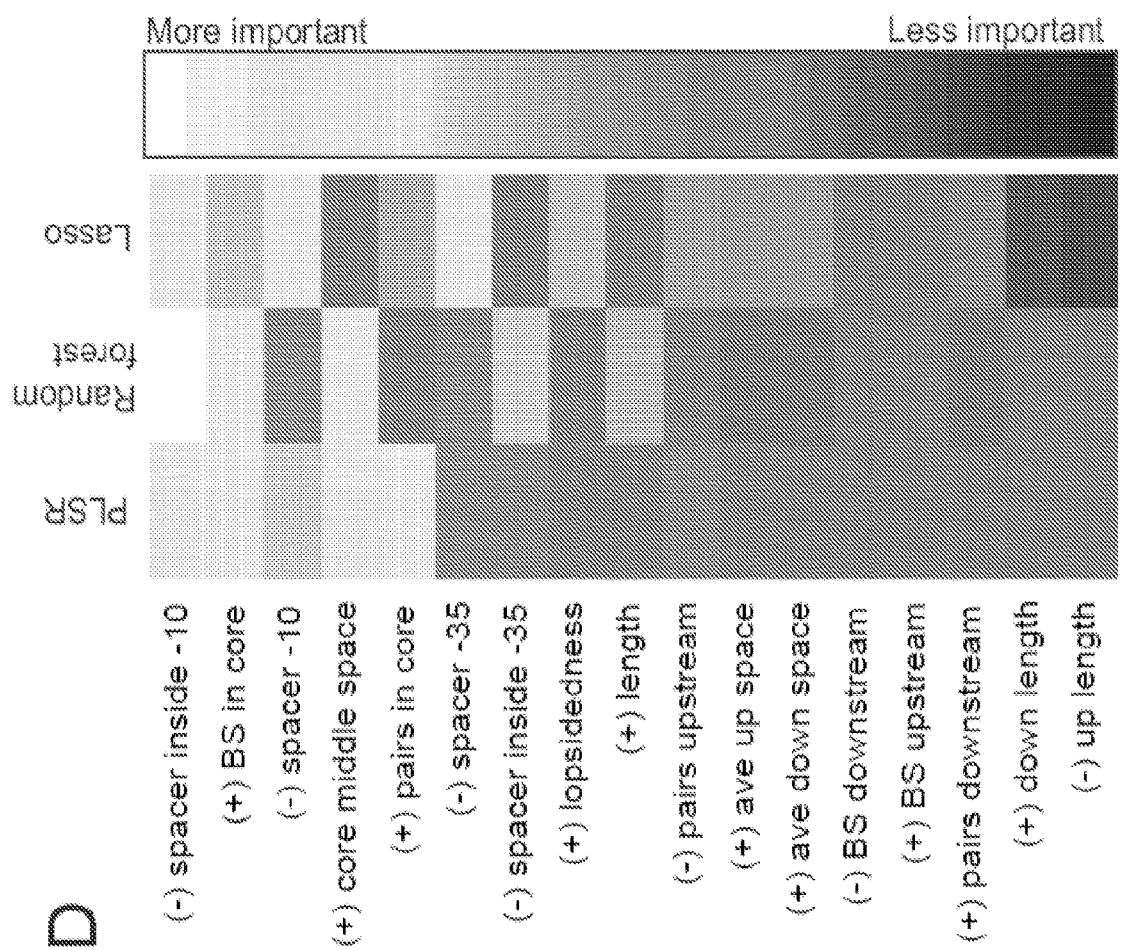

Statistical methods can provide insights into large or diverse data sets that are difficult to compare qualitatively or by inspection alone. Therefore, we performed a series of statistical analyses termed computational "feature selection" in order to determine which promoter features are important for predicting the relative repressibility of a given promoter in the presence of the ZFP. Given a set of feature "inputs," feature selection seeks to eliminate those features that are redundant or irrelevant to the prediction of a particular output. In our analysis, the output was defined as the repressibility (the negative of relative expression) exhibited by each promoter in the library. To generate the input list, we defined a set of 17 quantitative features that described each promoter in the library. Because we sought to elucidate general design rules and avoid over-fitting our particular promoter library, we defined the 17 features strictly on the basis of describing the locations of each ZFP binding site relative to the −10 box, the −35 region, and to other ZFP binding sites (FIG. 3A).

Figure 10:
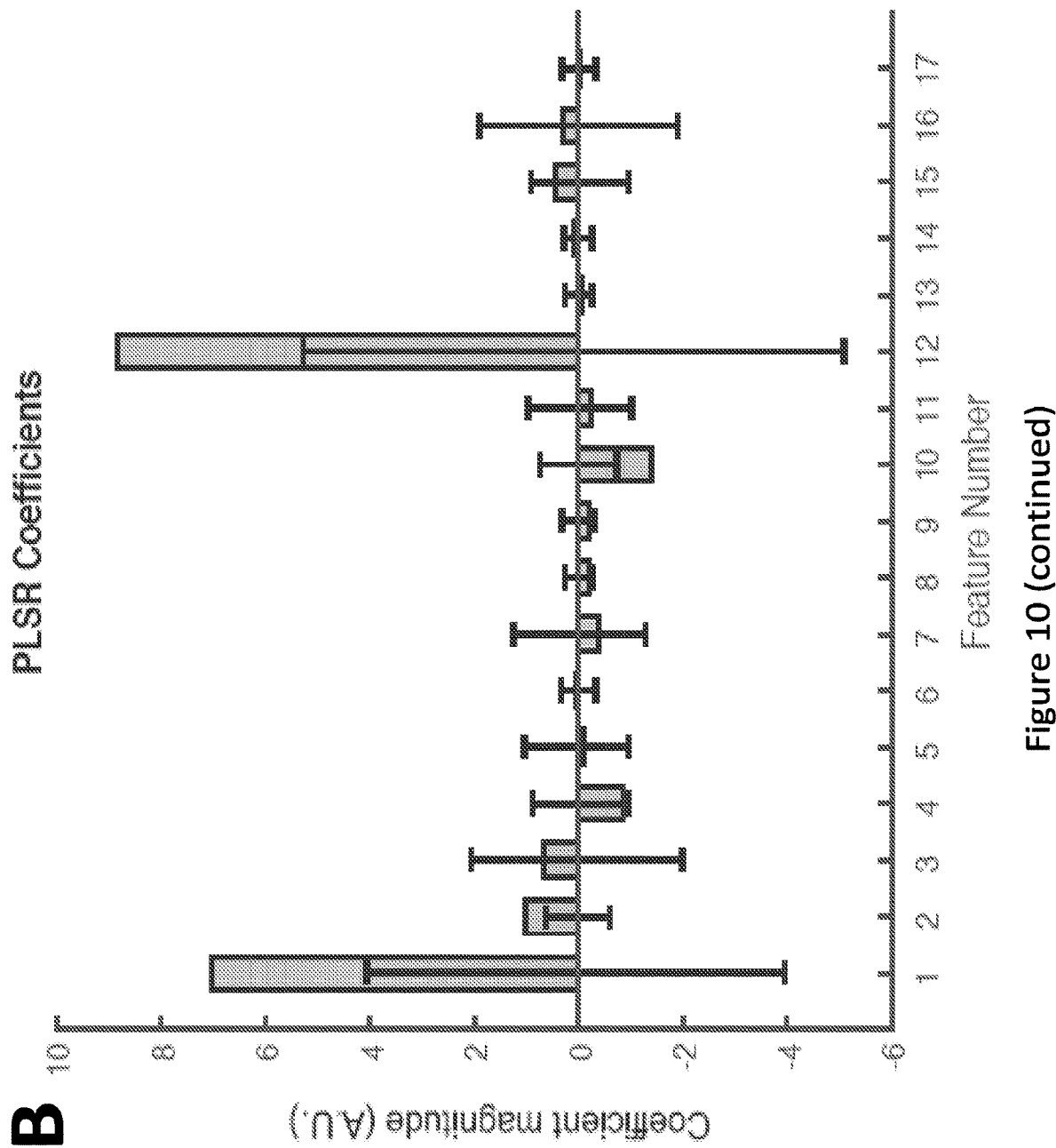
FIG. 10. Feature selection for BCR-ABL1-mediated repression. (A) Shorthand names and descriptions of the 17 features chosen to describe the promoter library. (B) Partial least squares repression (PLSR) coefficients associated with each feature (bars) are plotted along with corresponding standard deviations (error bars, which indicate the error around the mean coefficient value obtained by iterative permutation; this mean value was 0 in all cases, and thus error bars are plotted as deviations from 0). (C) PLSR coefficients associated with each feature were normalized by dividing each coefficient by its associated standard deviation, as obtained by iterative permutation (see Materials and Methods). Features with a large normalized coefficient value are most important. (D) Average mean squared errors obtained when each feature was permuted during the Random Forest analysis (see Materials and Methods). Features associated with a high mean squared error (when permuted) are more important. Feature numbers correspond to those listed in FIG. 3A in the main text.
Figure 10:
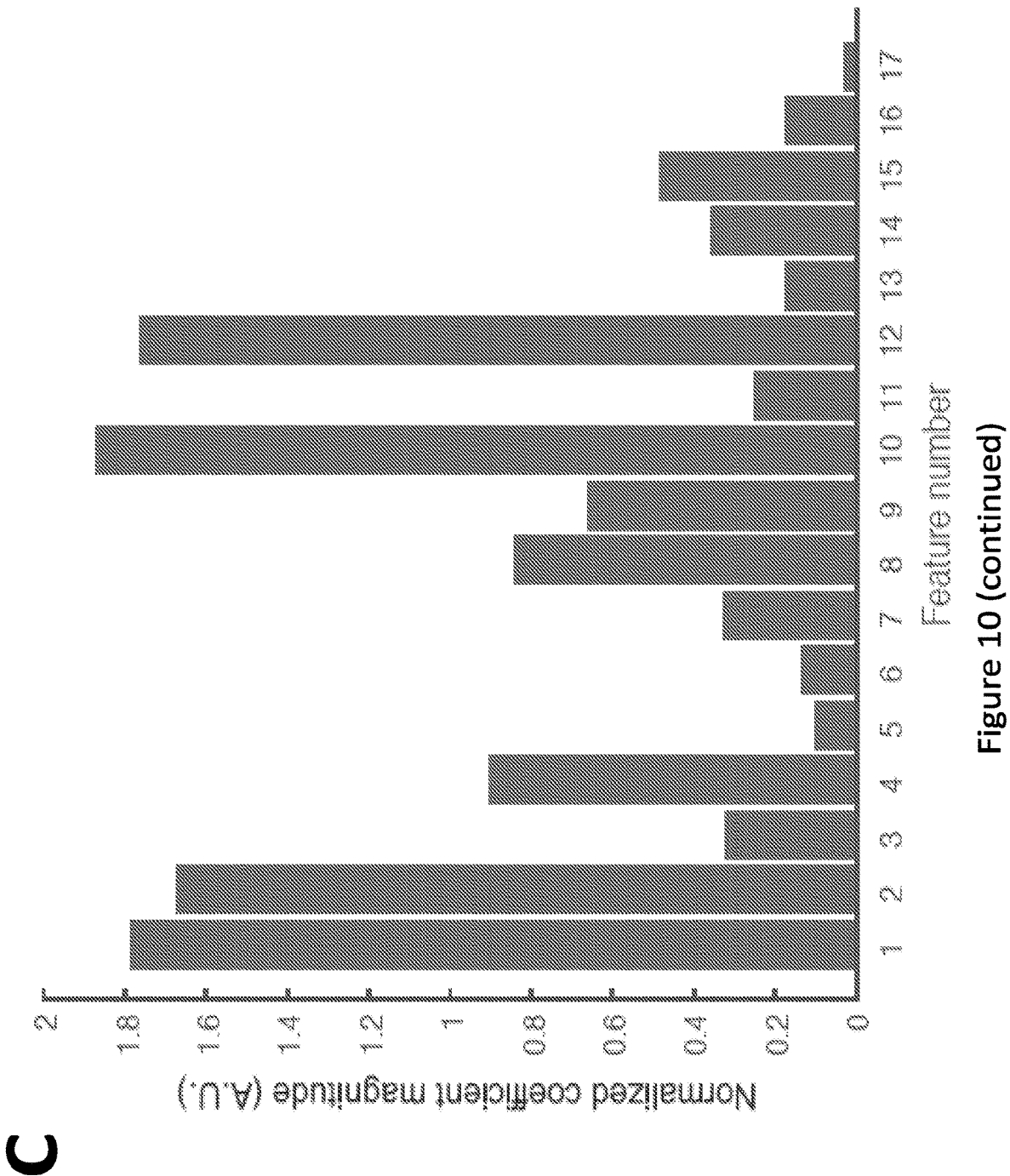
Figure 10:
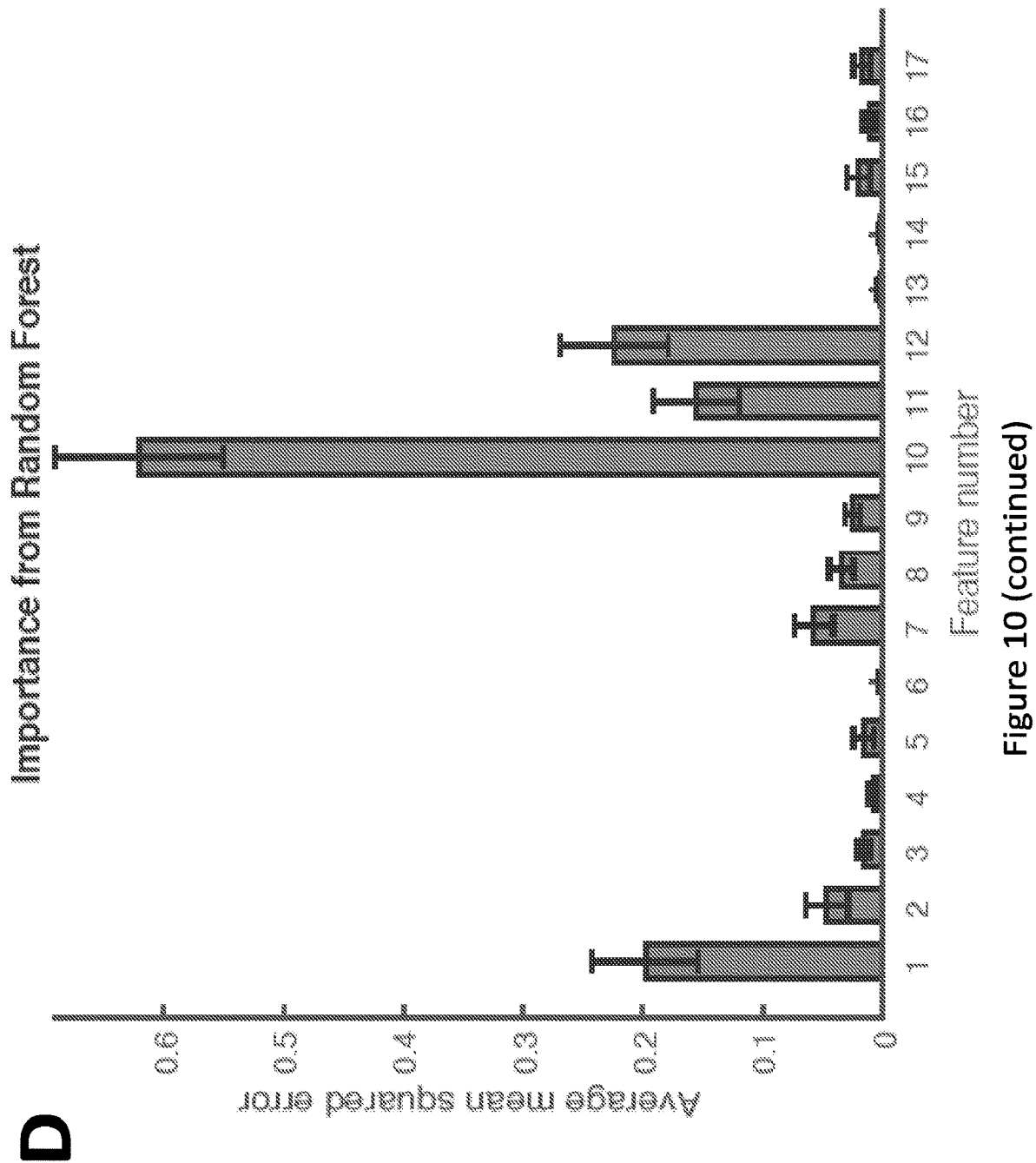

Three different feature selection methods were applied to analyze BCR-ABL1-mediated repression of our promoter library. We first used partial least squares regression (PLSR), in which the regression coefficient associated with each feature indicates the degree to which that feature explains variations in repressibility within our dataset. Each coefficient was scaled using a permutation test to correct for the coefficient one would calculate for a randomized (meaningless) output vector[58], and these corrected coefficients were used to generate a ranked lists of features (for PLSR coefficients, see FIG. 10). By repeating the PLSR using only fixed numbers of most important features, we found that the first few features explained much of the variance in the overall dataset (FIG. 3B). A similar trend was observed when repeating the PLSR with a limited number of principal components, indicating that principal components do not provide deeper understanding of this system than do single features. The second method used was Random Forest, which creates a predictive model of the system using decision trees. By iteratively generating decision trees using a subset of features, this method calculates the mean loss of accuracy when a given feature is removed, and this quantity is used to generate a ranked list of features by importance (FIG. 10). The final method used was Lasso regression, which performs least squares regression with an additional penalty placed on the magnitudes of regression coefficients[59]. This penalty is weighted by a parameter, $\lambda$, such that as $\lambda$ is increased, the coefficients of unimportant features shrink to zero; features are thus ranked by the number of iterations that they retain a non-zero coefficient as $\lambda$ is increased. For each value of $\lambda$, the regression fit was tested with 10-fold cross validation, to obtain a mean squared error (MSE) and number of retained coefficients for each value of $\lambda$ (FIG. 3C). A reasonable fit of the system was obtained using 3-5 features, with lower MSE for larger feature numbers likely representing over-fitting of noise in the dataset.

Overall, the three feature selection methods (PLSR, Random Forest, and Lasso) generated similar but not identical ranked lists of features (FIG. 3D). The most important features included spacer inside −10 and spacer −10, which were undesirable for repressibility, and BS in core, core middle space, and pairs in core, which were desirable for repressibility. Together, these findings indicate that placing binding sites as close as possible to the −10 box and −35 region are predicted to confer strong repressibility. Interpreting other features is less straightforward, such as core middle space, which describes whether there exist base pairs in the core other than ZFP binding sites; the three methods appear to disagree on the importance of core middle space. One possible explanation for this discrepancy is the influence of Go22 and Go92 on this analysis, since both of these promoters contain space in the core but no space on either side of the −10 box (Go22 and Go92) and no space on either side of the −35 region (Go92). As such, for these promoters, containing space in the core may be merely associated with the presence of other promoter features conferring repressibility. These cases may well emphasize the importance of spacer inside −10 and spacer −10. Moreover, Lasso, which is considered the most robust method for feature selection, ranked core middle space as unimportant, potentially by resolving this contradiction better than did the other methods. Altogether, this analysis enabled us to leverage our diverse promoter library to glean general, quantitative design principles for engineering ZFP-repressible promoters. However, it was not yet clear whether such rules would extend to the design of promoters regulated by ZFP-based biosensors.

Conversion of Transcriptional Repressors into Ligand-Responsive Biosensors.

Having established that BCR-ABL1 functions as a transcriptional repressor, we next investigated two strategies for converting this repressor into a biosensor. Here, the primary goal was to investigate general strategies for converting a ligand-binding protein into a ligand-responsive transcription factor. As described above, we hypothesized that such conditional regulation of gene expression may be achieved by fusing BCR-ABL1 to a ligand-binding domain. To investigate the feasibility of this approach, we chose the uniquely well-studied maltose binding protein (MBP), in part because this protein experiences a substantial and well-characterized conformational change (~9 Å decrease in separation between N and C termini) upon ligand binding[60-65] The first strategy we explored was termed the Split Zinc Finger (SZF) approach, in which BCR-ABL1 was split genetically such that the N and C termini of MBP were fused to BCR-ABL1-derived ZFPs. This strategy leverages prior observations in which the N and C termini of MBP were fused to FRET-paired fluorophores[66-69] split GFP fragments[28], or context-dependent fluorophores[45], each enabling the monitoring of ligand binding-induced conformational changes in MBP. Further rationale for this strategy is that ZFPs exhibited conditional DNA binding when this domain was genetically split and then reconstituted using either self-splicing inteins or protein-protein interactions[55, 70]. The second strategy we explored was termed the Split Protein (SP) approach, in which MBP was genetically split, with the halves fused to the N and C termini of intact BCR-ABL1. We hypothesized that such a construct may permit ZFP-DNA interactions in a manner that depends upon whether MBP is bound to maltose. The three most repressible reporters (Go66, Go85, and Go92) were used to evaluate the feasibility of each of these proposed biosensor mechanisms.

Figure 4:
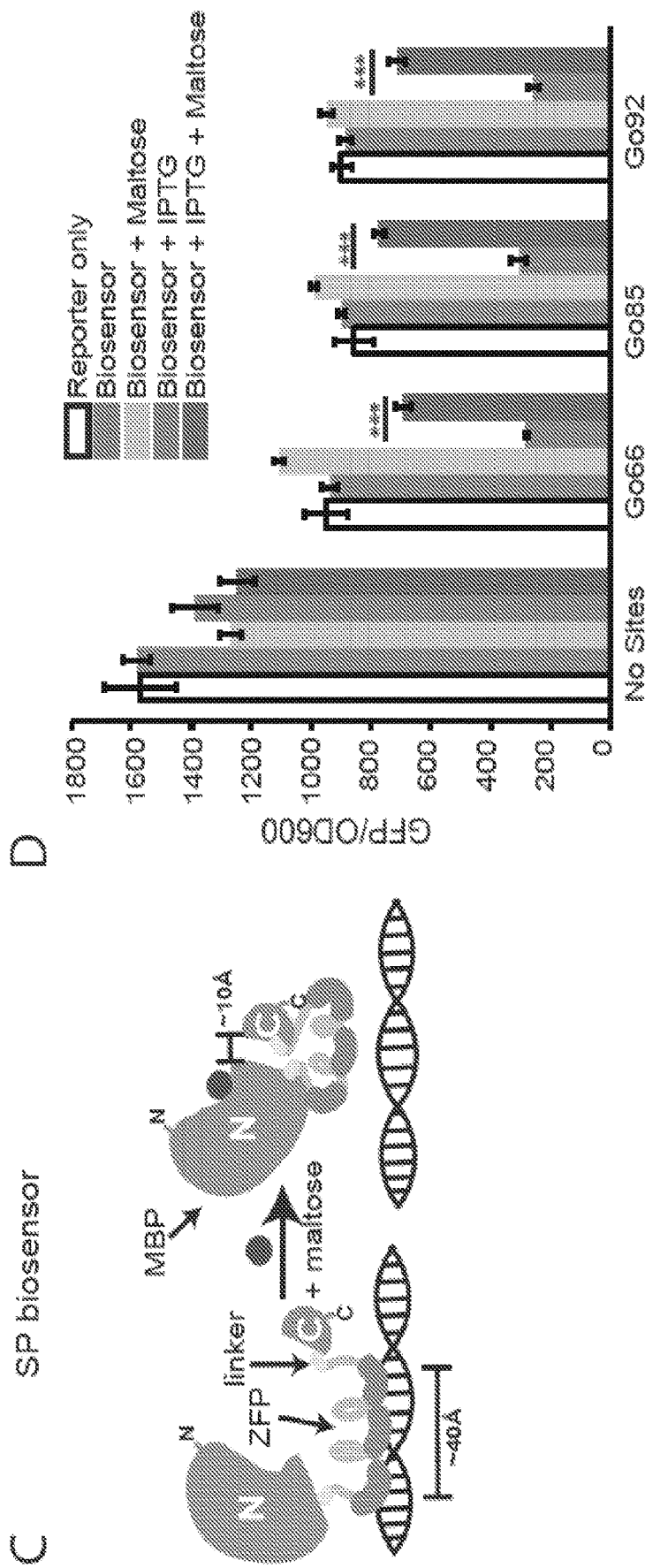
FIG. 4. Engineering novel biosensors using the split zinc finger (SZF) and Split Protein (SP) strategies. (A) This cartoon illustrates the proposed mechanism of action of an SZF biosensor. (B) SZF biosensor performance, when paired with the reporter plasmids indicated, was evaluated by inducing biosensor expression (30 µM IPTG) and evaluating alleviation of repression upon addition of maltose (100 mM). Five graph bars from left to right: Reporter Only; Biosensor; Biosensor+Maltose; Biosensor+IPTG; and Biosensor+IPTG+Maltose. (C) This cartoon illustrates the proposed mechanism of action of an SP biosensor. (D) SP biosensor performance was evaluated as in panel B. Five graph bars from left to right: Reporter Only; Biosensor; Biosensor+Maltose; Biosensor+IPTG; and Biosensor+IPTG+Maltose. (E) Comparison of the repression (i.e., reduction of relative expression) of reporter output upon expression of the SZF and SP biosensors compared to that mediated by inducing expression of the BCR-ABL1 ZFP alone. Three top points are values from SZF biosensors. Three bottom points are values from SP biosensors. (F) Tradeoff between level of expression of the SP biosensor (IPTG dose) with both repression (-maltose, bottom curve) and alleviation (+100 mM maltose, top curve) of expression from the Go66 reporter. (G) Response of reporter output to various extracellular concentrations of maltose, under two levels of biosensor expression (IPTG doses). Top horizontal bars indicate the 0 mM maltose case for 10 µM IPTG. Bottom horizontal boars indicated the 0 mM maltose case for 30 µM IPTG, with the width of each bar indicating one standard deviation. Top curves indicate 10 µM IPTG for increasing concentration of maltose: 0.1, 1, 10, or 100 mM. Bottom curves indicate 30 µM IPTG for increasing concentration of maltose: 0.1, 1, 10, or 100 mM. (H) The impact of the W340A mutation (SP: top curve: SP(W340A): bottom curve), which is reported to diminish maltose binding[72], on biosensor performance was evaluated using the Go92 reporter and analyses paralleling those used in panel G. Horizontal bars correspond to the indicated biosensor with 0 mM maltose, with the width of each bar indicating one standard deviation. Microplate data were collected over 7 sequential time points, spanning ~1.5 h of mid-exponential phase growth, and averaged. Relative expression was utilized in order to implicitly correct for any minor effects that IPTG or maltose many confer on $GFP/OD_{600}$ in a manner that is unrelated to expression of the ZFP or biosensor (see Materials and Methods for details). All data points represent mean values calculated from two independent experiments, each run in biological triplicate, and error bars represent one standard deviation ($p \leq 0.01$, *$p \leq 0.001$).
Figure 4:
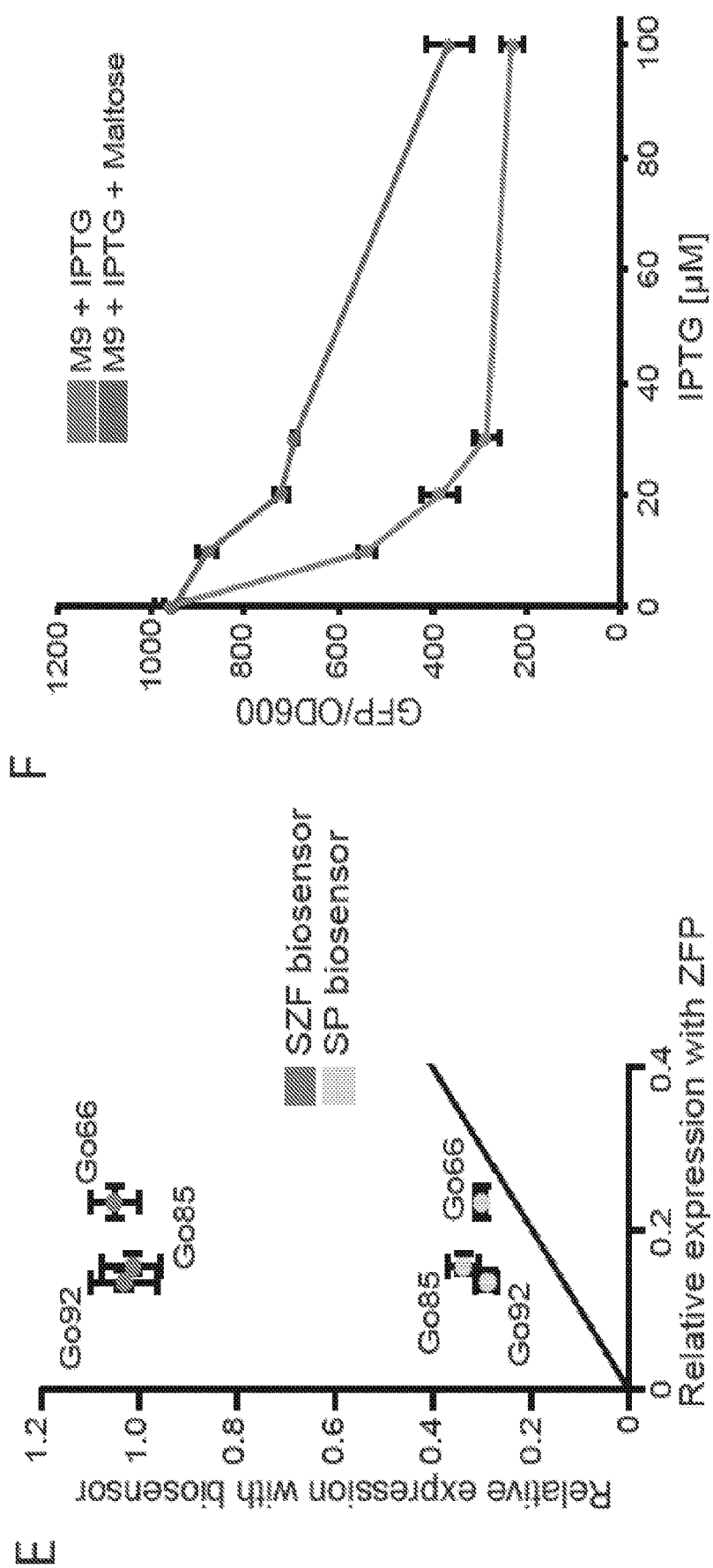
Figure 4:
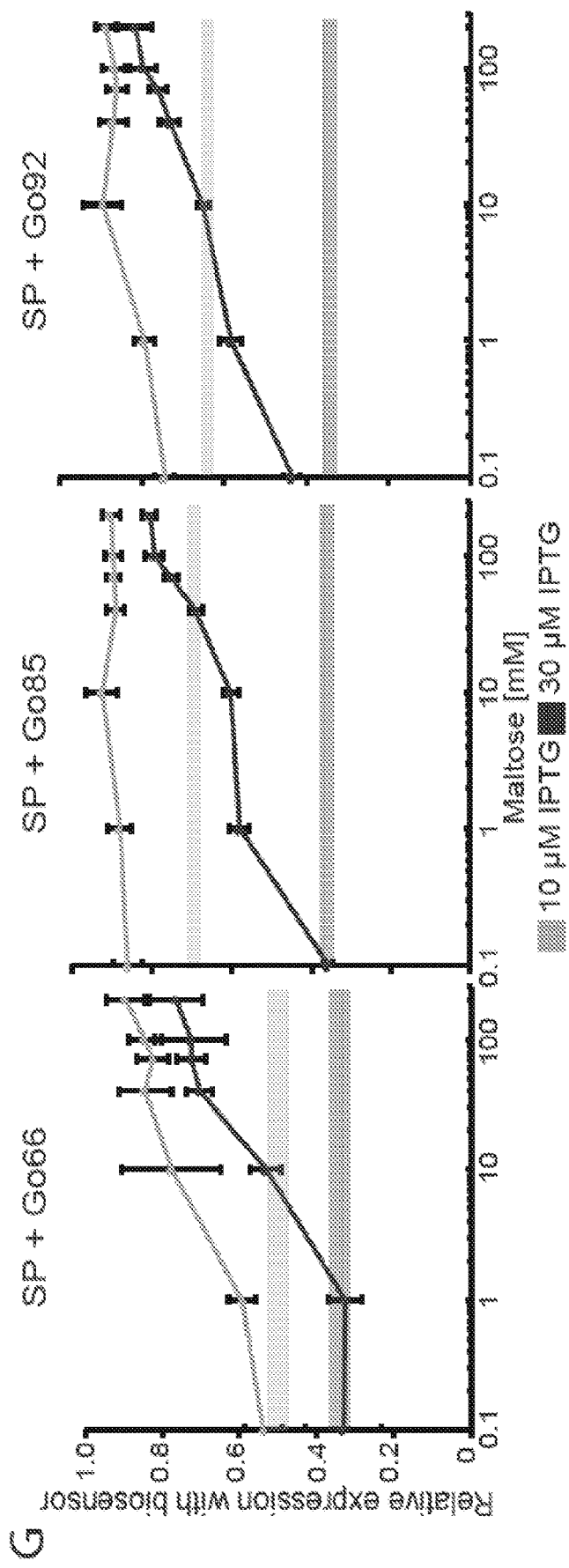
Figure 4:
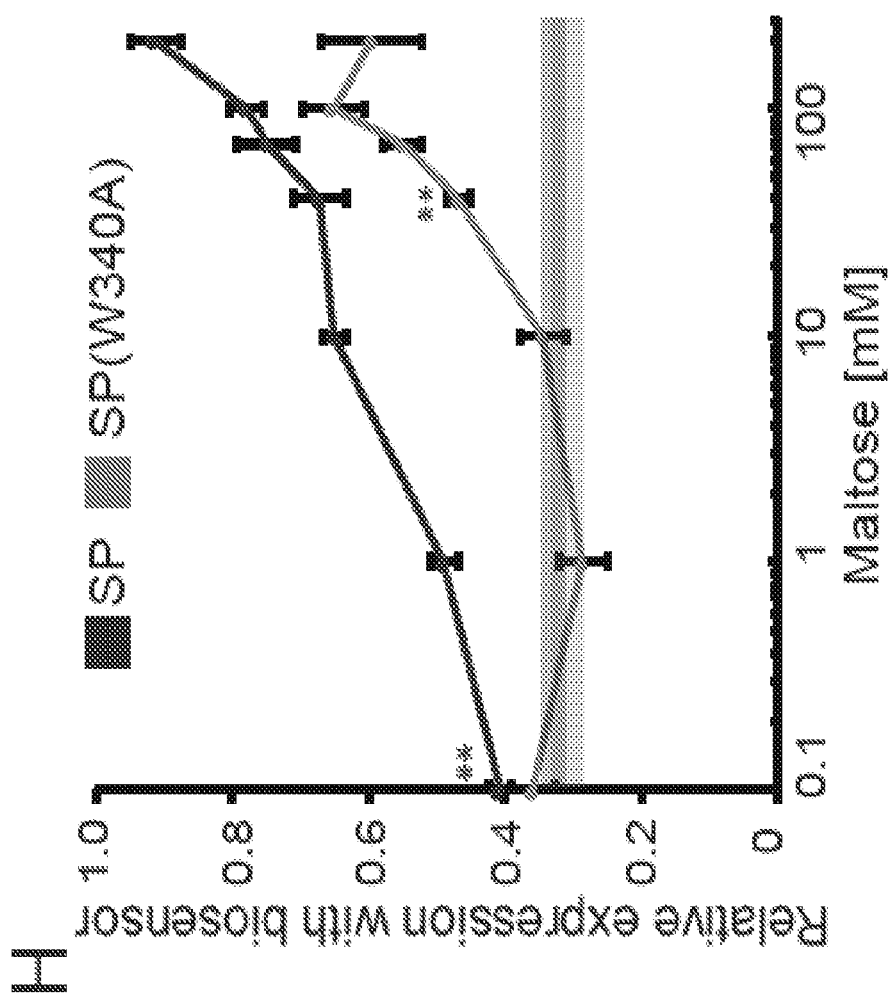

To investigate the SZF strategy, BCR-ABL1 was split between the first and second zinc fingers as previously described[55] (see FIG. 4A for the proposed mechanism). None of the reporters evaluated exhibited repression upon the induction of SZF biosensor expression (FIG. 4B). One potential explanation is that the three zinc fingers could not localize with the spacing or geometric orientation required to simultaneously bind a single BCR-ABL1 DNA binding site. While it may be possible to improve SZF biosensor-mediated repression by identifying promoters that place BCR-ABL1 binding sites in geometries that enable a split ZFP to bind, there is no guarantee that such a configuration would exist. Moreover, even if such a promoter were identified, such a design is likely to be a "one-off" solution specific to the MBP SZF biosensor. Therefore, we next evaluated the alternative SP biosensor design strategy, which has the potential to be more generalizable.

Figure 11:
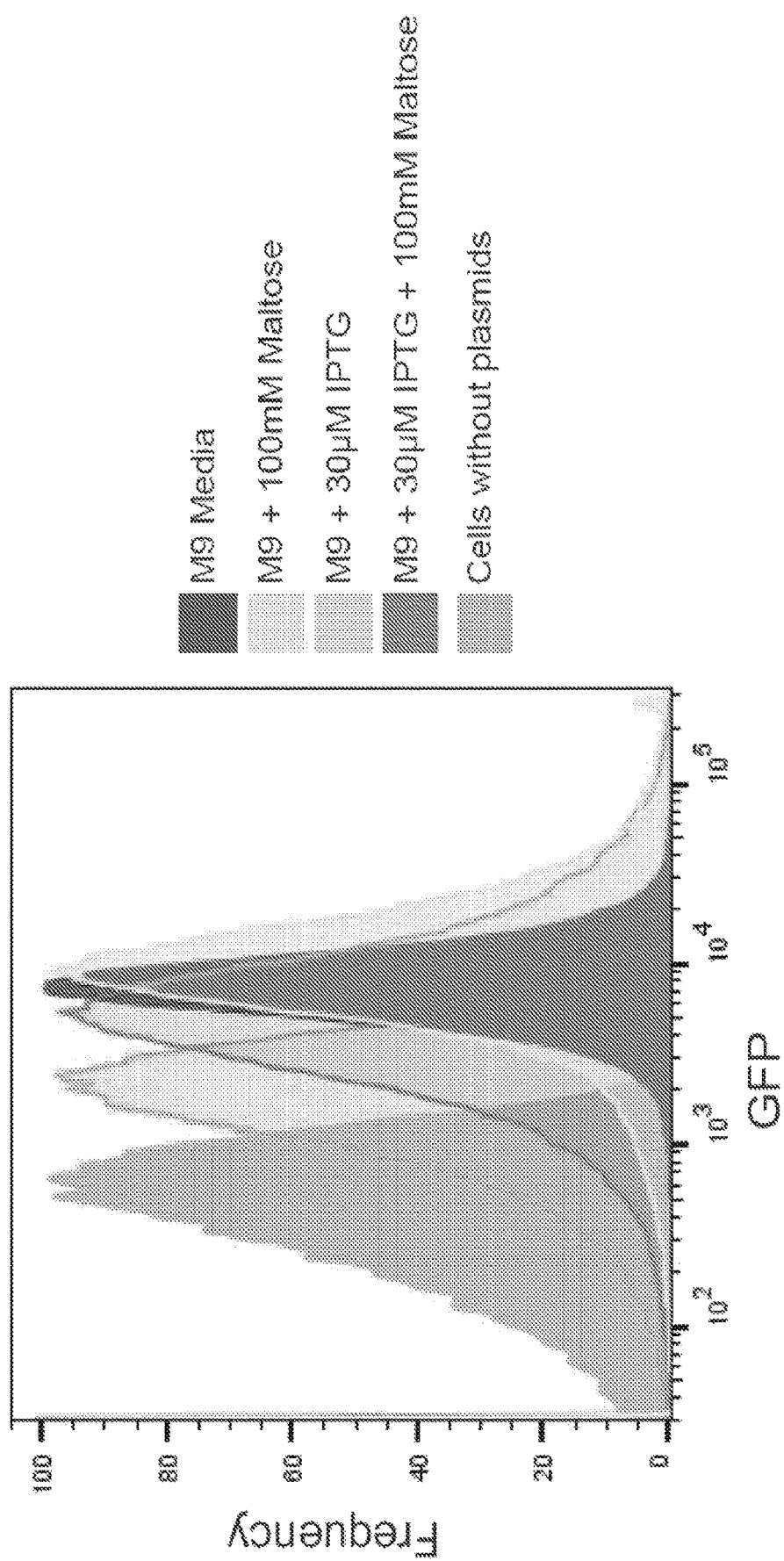
FIG. 11. Analysis of SP biosensor performance at the individual cell level. Cells containing the SP biosensor and the Go92 reporter were grown and induced in the same manner as was used for microplate reader analysis, and then these cells were analyzed by flow cytometry. Cells were gated using forward and side scatter to exclude debris. The histogram represents cells that contain neither the biosensor nor the reporter plasmids. The remaining histograms represent cells expressing the SP biosensor and the Go92 reporter, cultured under the medium conditions indicated.

To initially investigate the SP strategy, MBP was genetically split at the point previously reported to generate a functional chimera with beta-lactamase (BLA), termed "RG13"[24], and BCR-ABL1 was inserted between these N and C terminal fragments (see FIG. 4C for the proposed mechanism). We hypothesized that such a split site might support the SP mechanism because (a) in RG13, MBP retains the capacity to bind maltose and (b) in RG13, binding of maltose to MBP likely induces a conformational rearrangement of the overall fusion protein (or at least the stabilization of a conformation that alleviates disruption of the BLA active site[71]). This SP biosensor was again evaluated against a select set of reporters. Notably, induction of biosensor expression suppressed reporter output in a manner that was significantly alleviated in the presence of maltose (FIG. 4D). These data thus support the fundamental feasibility of the SP strategy. This observation is also consistent with our hypothesis that DNA binding was impaired in the SZF architecture, at least compared to the SP architecture. Notably, repressibility conferred by the SP biosensor was only slightly less than that observed with BCR-ABL1 ZFP alone (FIG. 4E). This correspondence suggests that the rules for predicting robust ZFP-mediated repression of reporter output (FIGS. 2, 3) seem to hold true for the SP biosensor, which also supports the generalizability of the SP strategy with respect to reporter construct design. As was observed for BCR-ABL1-mediated repression (FIG. 1D), SP biosensor-mediated repression and alleviation was also unimodal when analyzed by flow cytometry (FIG. 11).

Figure 12:
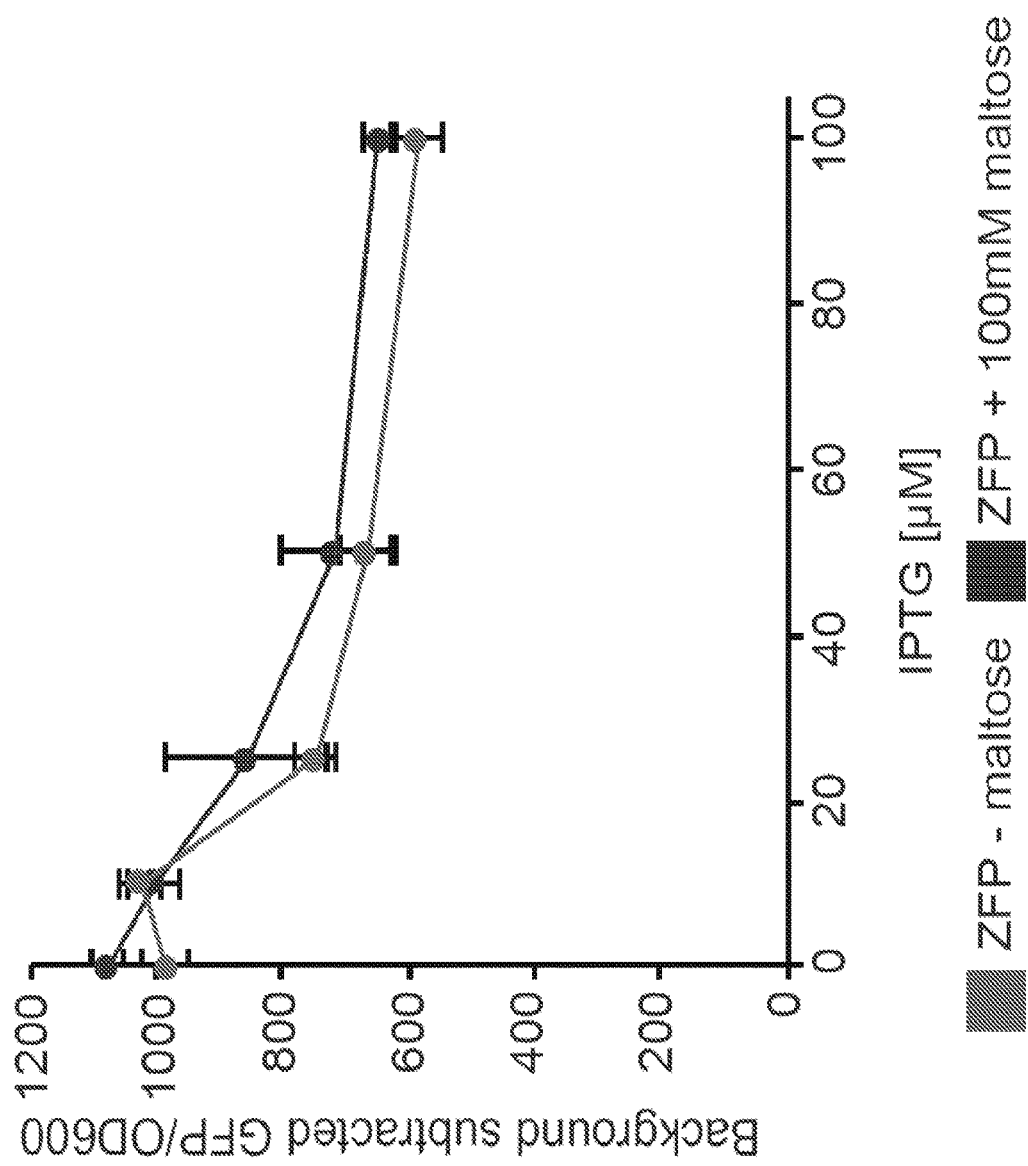
FIG. 12. The effect of maltose on the BCR-ABL1 zinc finger's repressibility over a range of IPTG induction levels. The BCR-ABL1 zinc finger was expressed with the pTrc2 promoter in combination with the Go66 reporter. Compare to biosensor performance in FIG. 4F. Note that the differences in repressibility between pTrc-BCR-ABL1 (shown here) and pBAD-BCR-ABL1 (shown in FIG. 1, FIGS. 2, 8, and 9) may be attributed to different levels of expression of this ZFP from the aforementioned promoters. Given the potential for catabolite repression of the pBAD promoter in the presence of maltose, pTrc-BCR-ABL1 was constructed to enable testing the effect of maltose on BCR-ABL1-mediated repression of the reporters. All data represent mean values calculated from two independent experiments, each run in biological triplicate, and error bars represent one standard deviation.
Figure 13:
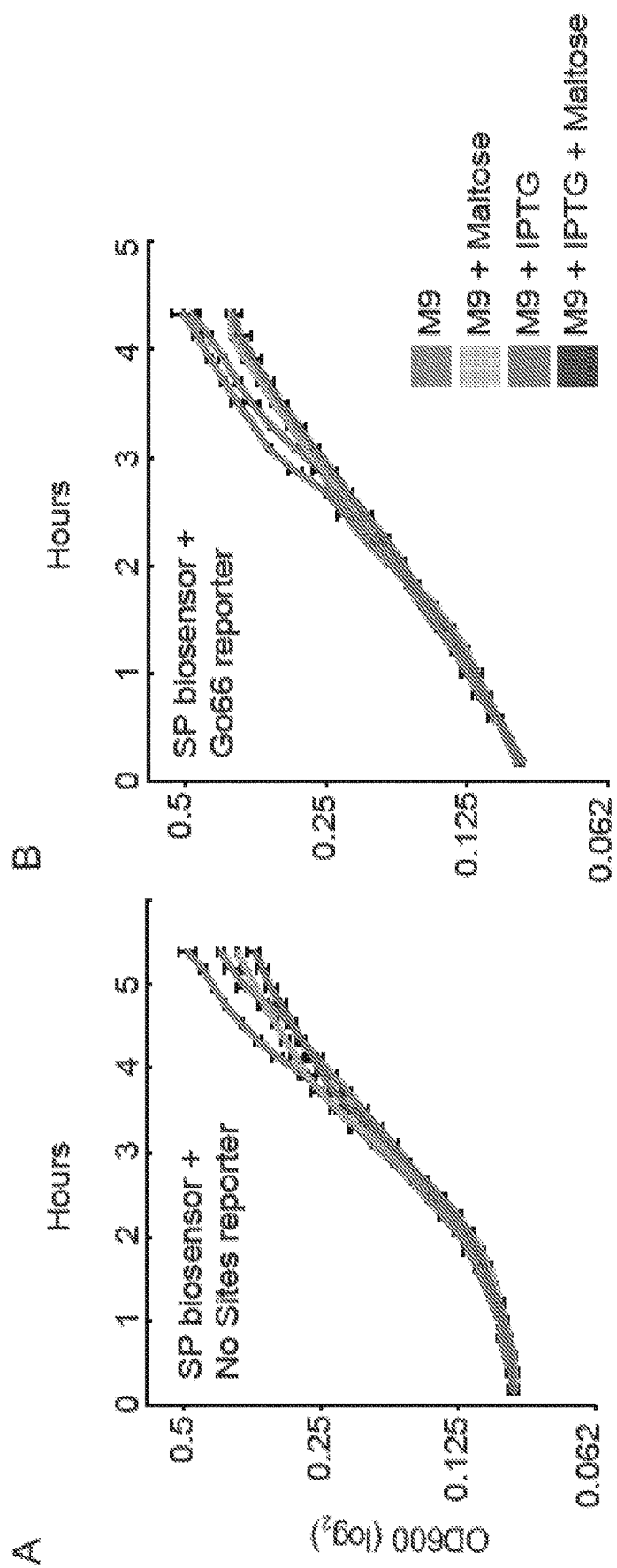
FIG. 13. Impact of 100 mM maltose and IPTG on cell growth. (A, B) Growth curves were collected for cells transformed with either the SP biosensor+the No Sites reporter (A) or the SP biosensor+the Go66 reporter (B). Experiments were conducted in biological triplicate, and error bars indicate one standard deviation.

Given these promising initial results, we next investigated how the method of SP biosensor implementation impacts the performance of the system. We first investigated how biosensor expression levels impact performance (FIG. 4F). With increasing biosensor expression levels, repression of the promoter increased (bottom curve), although maltose-mediated alleviation of reporter output also decreased (upper curve). Such a trend is the expected behavior of this system if, at higher levels of biosensor expression, intracellular concentrations of maltose are insufficient to drive all of the biosensors into the ligand-bound (alleviated) state. We would propose two hypotheses that could explain this phenomenon. First, at higher concentrations of maltose, transport limitations may confer an upper bound on the intracellular concentration of maltose, irrespective of the extracellular maltose concentration. Second, it remains possible that even at saturating intracellular concentrations of maltose, the maltose-bound form of our biosensor may still bind DNA (and repress transcription) to a lesser but finite extent, compared to the apo form of the biosensor. Thus, we determined that for the case of a relatively high extracellular concentration of maltose (100 mM in medium, which is expected to be substantially higher than the concentration in the cytoplasm), induction of biosensor expression with 30 µM IPTG conferred a robust balance between repression and maltose-mediated alleviation of reporter output. To exclude the possibility that some other aspect of cell biology or ZFP function could explain the maltose-mediated alleviation of reporter output, a similar analysis was performed using cells expressing the ZFP alone (i.e., in place of the SP biosensor). As expected, the addition of maltose had no significant impact on ZFP-mediated repression of the reporter (FIG. 12). Moreover, the addition of maltose did not substantially impact cell growth (FIG. 13). We next investigated how extracellular maltose concentration impacts biosensor performance (FIG. 4G). With the caveat that intracellular concentrations of maltose are expected to be substantially lower than are extracellular concentrations, we observed that biosensor responsiveness varied with extracellular maltose concentration, and for the most sensitive reporters (Go92 and Go85), modest but significant alleviation was observed at extracellular maltose concentrations as low as 0.1 mM. To further investigate how maltose binding to MBP domains impacts SP biosensor performance, we repeated this dose-response analysis after making a mutation in the MBP domain (W340A), which has been reported to substantially weaken, but not ablate, MBP binding to maltose[72] (FIG. 4H). As expected, a substantially higher (~400×) extracellular concentration of maltose was required to alleviate reporter output in the W340A SP mutant case. Altogether, these observations demonstrate the feasibility of engineering novel biosensors using the SP strategy. Although the MBP split site used in this initial construct was not selected to optimally implement the SP strategy, our overall goal was to evaluate the SP strategy in general. Therefore, we carried this functional SP biosensor forward for further development.

Contributions of Biosensor Biophysical Properties to Biosensor Performance.

In order to investigate how general biophysical properties of a biosensor impact its performance, we next performed a series of rational modifications of the SP biosensor protein. First, we hypothesized that if DNA binding affinity limits the degree to which our biosensors repress transcription, then replacing the BCR-ABL1 domain with a ZFP that binds to DNA with higher affinity would improve transcriptional repressibility in the absence of maltose. However, since BCR-ABL1 interacts with its binding site with a $K_d$~78 pM[50], a simple model of binding equilibrium would suggest that promoter occupancy should not vary much with changes in this high affinity binding constant. As a point of reference, we note that the dimeric tetracycline repressor (TetR) binds to its operator sequence (tetO) with a similar $K_d$~20 pM[73], although tetR is understood to achieve exquisite transcriptional repression through contorting the target DNA rather than through high affinity binding alone[74]. In order to directly investigate the relationship between affinity and repression in our system, and to investigate the modularity of our biosensor vis-à-vis ZFP domain choice, we replaced BCR-ABL1 with the Zif268 ZFP domain from the human EGR1 protein. Zif268 binds its 9 bp binding site with a $K_d$~8 pM (~10 times tighter than that of BCR-ABL1)[50]. Go92 was converted to Zif268-responsive promoter by replacing the BCR-ABL1 binding sites with Zif268 binding sites (GCA-GAAGCC versus GCGTGGGCG, respectively). The SP biosensor was also modified to replace the BCR-ABL1 ZFP with Zif268 (SP-Zif268). SP-Zif268 did not exhibit an enhanced capacity to suppress reporter output, although it instead exhibited reduced fold-alleviation in the presence of maltose compared to the original SP biosensor (FIG. 5A). Altogether, these observations are consistent with a simple model wherein increasing the affinity of the biosensor for its target DNA did not increase repression, presumably because such a change would not impact promoter occupancy. Moreover, the fact that the SP-Zif268 biosensor exhibited significant (if somewhat diminished) functionality indicates that the ZFP domains within SP biosensors may be exchanged in a modular fashion.

Figure 5:
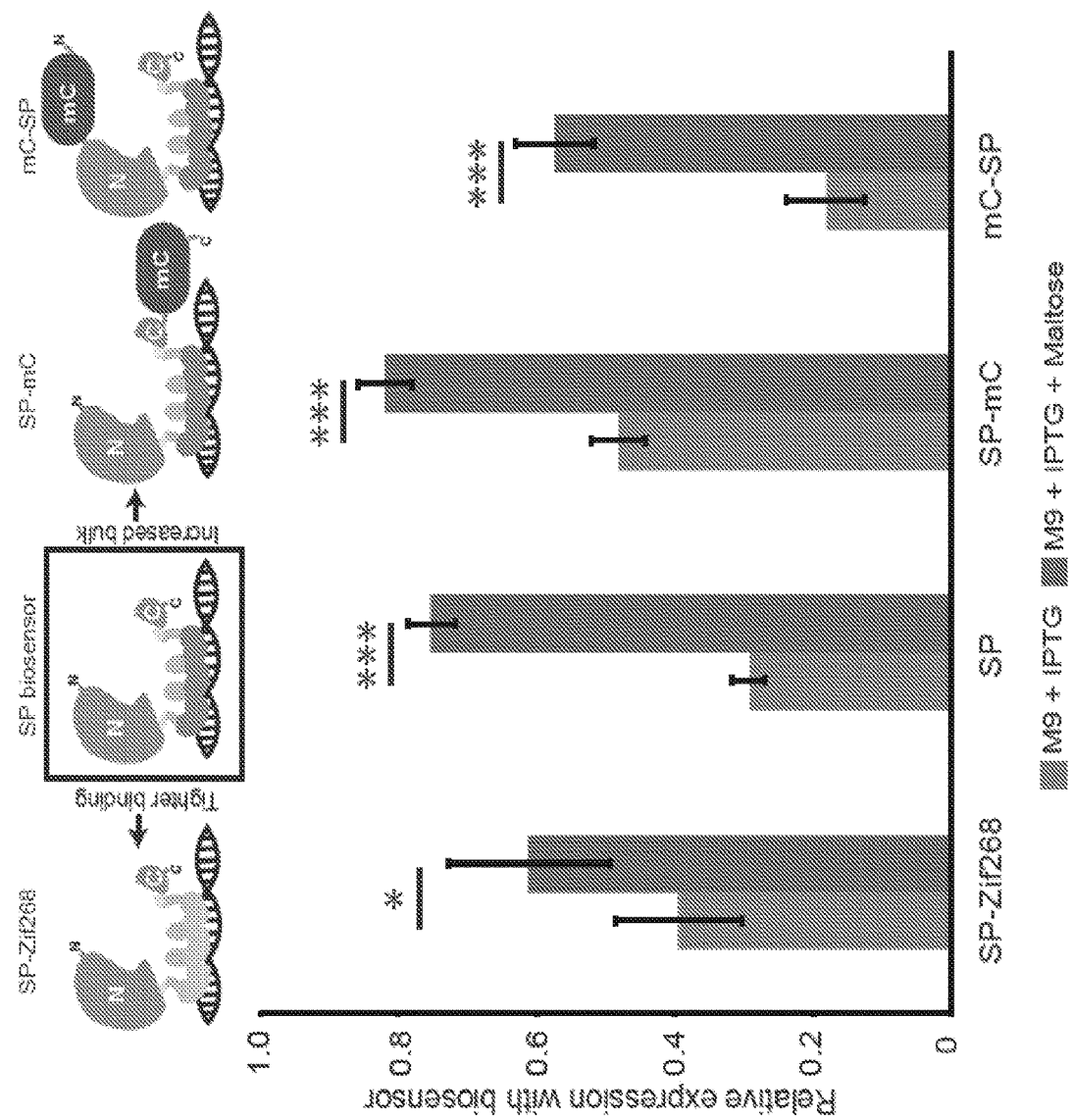
FIG. 5. Contributions of biosensor biophysical properties to biosensor performance. At top, the illustration summarizes the biosensor design space explorations described in this figure, using the SP biosensor as a reference case. SP-Zif268 incorporates the tighter binding Zif268 ZFP in place of BCR-ABL1. In SP-mC and mC-SP, mCherry was fused to the C-terminus or N-terminus of the SP biosensor, respectively. Below, biosensor performance, when paired with the Go92 reporter, was evaluated by inducing biosensor expression (30 µM IPTG) and evaluating alleviation of repression upon addition of maltose (100 mM). Microplate data were collected over 7 sequential time points, spanning ~1.5 h of mid-exponential phase growth, and averaged. All data represent mean values calculated from two independent experiments, each run in biological triplicate, and error bars represent one standard deviation (*$p \leq 0.05$, *** $p \leq 0.001$).

We next investigated how biosensors size may impact reporter repression, for example by sterically occluding RNA polymerase binding to the −10 box and −35 region. To this end, the fluorescent protein mCherry was fused to either the N- or C-terminus of the SP biosensor to generate mC-SP or SP-mC, respectively. In this experiment, mCherry was selected as a functionally "neutral" fusion partner in order to investigate the impact of increasing the bulk of the biosensor alone. Although the SP-mC modification did not improve biosensor performance, the mC-SP construct notably exhibited both improved repression and increased fold-induction of reporter output upon the addition of maltose (FIG. 5). Altogether, these data suggest a useful strategy for building novel biosensors in which the tradeoff between desired performance characteristics may be optimized for a particular application. In general, adding steric "bulk" may outperform enhancing DNA binding for increasing repression in the "off" state without sacrificing the degree to which the regulated gene is expressed when in the "on" state.

Discussion

In this study, we investigated a potentially generalizable strategy for converting metabolite-binding proteins into metabolite-responsive transcription factors. By systematically and quantitatively evaluating the design principles governing the performance of such biosensors, which was the focus of this investigation, this work establishes a foundation for pursuing the long-term goal of engineering repertoires of customized metabolite-responsive biosensors. By leveraging modular design of both promoter libraries and biosensor proteins, these investigations elucidated a number of design principles that are useful for both explaining the variations observed in our libraries and for guiding the design of novel biosensors in subsequent work.

Using a library of engineered promoters, we identified several important rules by which binding of a ZFP to DNA confers a repression of transcription. Interestingly, nearly all promoters evaluated were repressed, at least to some degree, and none exhibited increased expression in the presence of the ZFP. The BCR-AB1 ZFP alone was sufficient to achieve significant transcriptional repression, even though this protein is smaller than canonical natural transcription factors, such as TetR and LacI (106 aa compared to 221 aa (TetR) and 374 aa (LacI)). This minimal ZFP also regulated gene expression in manner somewhat different from that conferred by a previously described fusion between a ZFP and a transactivation domain from CRP. Lee at al. observed that this ZFP-CRP fusion conferred transcriptional activation when bound upstream of the +1 site and repression when bound downstream of the +1 site[36], while our minimal ZFP (which lacks a transactivation domain) conferred repression even when bound upstream of the +1 site (FIG. 2). We determined that placing ZFP binding sites as close as possible to the consensus −10 box and −35 region of the promoter yielded the highest level of transcriptional repression. The −10 box and −35 region are the sites at which the transcription initiation factor σ70 binds in order to mediate recruitment and assembly of the RNA polymerase (RNAP) complex. Therefore, we hypothesize that placing the ZFP binding sites very close to the −10 box and −35 region effectively prevents the σ70 from binding to this region of DNA and/or σ70-mediated recruitment of RNAP. The greatest repression was observed when both the −10 box and −35 region were abutted with ZFP binding sites, and blocking the −10 box may confer greater repression than does blocking the −35 region (FIGS. 2G, 3D). It is possible that these observations may be leveraged to achieve greater repression by overlapping the ZFP binding sites with the conserved −10 box and −35 region, since binding of biosensors to these sites may more efficiently block σ70-mediated recruitment of RNAP. One potential challenge associated with this strategy is the potential to repress endogenous genes that share the consensus −10 box and −35 regions, although minimizing overlap with these consensus sequences could mitigate this problem.

Our comparison of two potential biosensor engineering strategies—the SP (split protein) and SZF (split zinc finger) architectures—revealed several insights into the feasibility and generalizability of each approach. The SP biosensors repressed the most-repressible reporters to nearly the same extent as did the ZFPs alone, suggesting that the rules governing promoter design may be generalizable across SP biosensors (FIG. 4D). In contract, the SZF biosensor evaluated conferred no repression of reporter output (FIG. 4B). We hypothesize that insertion of MBP between the fingers of BCR-ABL1 precluded simultaneous binding of DNA by all three zinc fingers. Even if this geometric constraint were alleviated by modulating the protein or DNA sequences, it is likely that such a solution would be unique to each biosensor. Therefore, the SZF approach may be generalizable, but not readily so. In contrast, the SP approach was both more effective and may also be more readily generalizable.

Our investigation also provided several insights into the mechanism by which this initial SP biosensor functions and the prospects for extending this approach to generate novel biosensors. In many ways, these insights leverage the wealth of information available to describe our model ligand-binding domain, MBP. The SP biosensors utilized the MBP split sites that were identified by using a random domain insertion approach to generate the "RG13" MBP/BLA fusion protein[24]; the N terminal half of SP comprises the first 316 aa of MBP, and the C terminal half comprises residues 319-370 of MBP. In the crystal structures of both MBP and RG13, residues 316R and 319A are ~10 Å apart[62, 71]. However, it should be noted that the RG13 crystal structure was obtained in the presence of saturating $Zn^{2+}$, a condition which ablated the activity of the BLA subdomain of the protein, and that no maltose-bound (or zinc-free) structure of RG13 has been obtained. Thus, these distances should be treated as estimates as to how RG13 residues 316R and 319A are positioned when the protein is expressed under physiological conditions. When MBP binds maltose, the separation of these residues increases by no more than ~3 Å[60]. In contrast, when a $Cys_2$-$His_2$ class ZFP binds to its cognate 9 bp of DNA, the distance separating the N- and C-termini of the ZFP is ~40 Å[75]. Therefore, we hypothesize that in order for the ZFP domain of the SP biosensor to adopt a conformation capable of binding its 9 bp DNA target, residues 316R and 319A may be separated by as much as 40 Å. Furthermore, since the addition of maltose alleviates biosensor-mediated repression of transcription (and therefore impairs or ablates DNA binding), we hypothesize that maltose binding to the SP biosensor stabilizes interactions between the split MBP fragments, such that residues 316R and 319A are retained in a close (~13 Å) spacing, which prevents the ZFP domain from adopting a conformation capable of DNA binding (FIG. 4C). Importantly, if the SP biosensor operates via this ligand binding-induced stabilization mechanism, then biosensor function need not rely upon a ligand-binding induced conformational change in MBP. Thus, this mechanism could be extended to ligand-binding proteins that do not experience a ligand binding-induced conformation change as dramatic as that exhibited by MBP. Moreover, the proposed ligand binding-induced stabilization mechanism is consistent with the "induced fit" model of substrate binding, in which ligand binding causes a shift in protein structure that results in an increase in the stability of the ligand-bound complex. Indeed, ligand binding-induced stabilization may confer allosteric regulation of many proteins, and this property may even be engineerable[76]. Thus, we speculate that the mechanism of the MBP-based SP biosensor may be extended to biosensors based upon distinct ligand-binding domains. Moreover, there exist many methods by which proteins can be split, fused, and screened, including in vitro methods such as circular permutation and domain insertions, as well as computational methods for predicting effective split sites, such that evaluating whether a given ligand-binding protein is amenable to conversion into a biosensor using the SP approach is relatively straightforward[25, 77-80]. In fact, periplasmic binding proteins such as MBP may be generally amenable to conversion into molecular switches via domain insertion, as was demonstrated by the insertion of TEM-1 beta-lactamase into ribose binding protein, glucose binding protein, and xylose binding protein[81]. Additionally, an allosterically regulated version of Cas9 has been developed by using domain insertion to fuse Cas9 to estrogen receptor-α to create a repressor that is inducible by the addition of 4-hydroxytamoxifen[40]. In this study, a site in Cas9 that is permissive to protein insertion was first identified using random domain insertion of a PDZ domain. Thereafter, the estrogen receptor-α was inserted into this site following the rationale that this receptor undergoes a substantial conformation change upon ligand binding, bringing its termini within 21 Å of one another in the presence of ligand, such that only the ligand bound conformation of the receptor may exhibit a structure that avoids disruption of the Cas9 structure (and, presumably, function). Thus, while this technology is of substantial utility for regulating Cas9, it is not yet clear whether or how this approach may be extended to generate Cas9-based regulators that are responsive to a range of metabolites or ligands. Altogether, the SP strategy appears to be a promising and potentially generalizable method for generating novel biosensors, although further investigation is required to determine which types of ligand-binding proteins may be most readily converted into biosensors via this approach.

Our investigation also provided several insights into how biophysical properties of the biosensor itself could impact its overall performance. First, comparing SP biosensors based upon BCR-ABL1 to those based upon Zif268, the latter of which binds its cognate DNA with approximately 10-fold greater affinity, we observed that the SP-Zif268 biosensor repressed transcription to a similar extent but exhibited a reduced response to the addition of maltose. As discussed above, the observed comparable degree of repression is consistent with a simple model of high affinity binding, in which both SP and SP-Zif268 biosensors achieve a similar level of promoter occupancy. To interpret the reduced response to maltose, we hypothesize that due to the tighter binding of Zif268 to DNA, even the maltose-bound state may interact with DNA to some extent that represses reporter output (indeed, the same may be true to a lesser extent for the original SP biosensor). For example, if each maltose-bound biosensor exists in an equilibrium between states that are competent (disfavored) versus incompetent (favored) for DNA binding, then the higher affinity with which Zif268 binds DNA may cause biosensors based upon this protein to become "trapped" in a DNA-bound state, even when bound to maltose. Finally, the fact that the SP-Zif268 biosensor nonetheless exhibited significant (if somewhat diminished) functionality indicates that, within the SP framework, the ZFP domains may be exchanged to tune biosensor performance or to regulate novel reporter constructs.

We also investigated the role of biosensor size on performance, which provided some insights into how biosensor performance may be tuned. We observed that fusing mCherry to the N terminus of the SP biosensor (mC-SP) improved both reporter repression and fold induction upon the addition of maltose, although no such effect was observed when mCherry was fused to the C terminus of the SP biosensor (SP-mC). While it is not possible to provide a specific structural explanation for these effects, a reasonable speculation is that the mC-SP biosensor sterically occludes recruitment of the RNAP to a greater extent than does the original SP biosensor. If this were true, it could be possible to achieve even greater repression of reporter expression by exploring the addition of "bulky" domains of various sizes, shapes, and linker geometries to a candidate SP biosensor.

We also attempted to compare the performance of our initial SP biosensors to that of some naturally-evolved biosensors, using the systematic characterization of the latter that was recently reported by Rogers et al.[5]. Rogers et al. evaluated fold-induction after cells had reached stationary phase, while we evaluated both repression and alleviation during exponential growth, so we re-analyzed our data from the experiments reported in FIG. 5 using a later time point at which cell growth had slowed, to facilitate this comparison (FIG. 14). While this analysis did indeed lead to higher calculated values for degree of repression and fold-alleviation upon the addition of ligand (6±0.4 fold-repression and 3.8±0.3 fold-alleviation for the mC-SP biosensor), the natural biosensors generally achieved a greater fold-induction, due in large part to the more efficient suppression of output gene expression when in the ligand-free "off" state. While such nuances reflect the manner in which biosensor performance is evaluated to some extent, this investigation more importantly identifies specific performance attributes of SP biosensors that might be targeted to better approach the performance of naturally-evolved biosensors.

Although we evaluated and identified several promising strategies for improving biosensor performance, it is possible that when extending the SP approach to target applications, biosensor performance may be further improved by either design-driven or screening-based methods. Some strategies could entail refining reporter design. Depending on the application requirements, fold-induction may be improved by locating the reporters on single-copy plasmids or on chromosomal DNA (instead of on low copy number plasmids as described here) to increase promoter occupancy for a given quantity of biosensors. Alternatively, the promoter sequence could be altered to partially diminish interactions with 670, potentially using either targeted mutations or random promoter mutagenesis followed by selection to "tune" a promoter to match the properties of a given biosensor. Other strategies could improve the biosensor proteins. In particular, although utilizing the RG13 split site for MBP proved to be feasible for generating our initial SP biosensors, it is likely that evaluating all possible ZFP insertion sites into a ligand binding protein may identify fusion proteins that are specifically suited to the SP mechanism. Based upon our observations of the factors limiting SP biosensor performance, candidate biosensors may also be improved by random mutation and directed evolution (e.g., optimizing allosteric regulation to enhance ligand binding-induced alleviation of DNA binding). A final strategy could be to process the output of our existing biosensor/reporter(s) system to achieve preferable overall performance characteristics. For example, reporter output could be coupled to additional genetic circuitry, such as RNA-based toe hold switches or positive feedback circuits to amplify reporter output, and with some tuning, increase fold-induction[82, 83]. By leveraging the modularity conferred by programmable ZFP binding[50, 75] it may also be possible to implement multiple SP biosensors in a single cell. Moreover, high throughput genome engineering approaches such as MAGE[84] could make it possible to place even endogenous genes under partial or total control of such engineered biosensors. In sum, a modular approach to biosensor engineering is likely to accelerate the generation of novel biosensors, iterative improvement of biosensor performance, and adaptation of biosensors for novel applications in metabolic engineering and synthetic biology.

Materials and Methods

Bacterial Strains and Culturing.

All experiments were conducted in TOP10 *Escherichia coli* cells (F-mcrA Δ(mrr-hsdRMS-mcrBC) φ80lacZΔM15 ΔlacX74 nupG recA1 araD139 Δ(ara-leu)7697 galE15 galK16 rpsL(Str$^R$) endA1 λ$^-$) (Life Technologies). Cells were maintained in Lysogeny Broth (LB) Lennox formulation (10 g/L of tryptone, 5 g/L of yeast extract, 5 g/L of NaCl) supplemented with appropriate antibiotics (Ampicillin 100 μg/mL or Kanamycin 50 μg/mL). All experimental analysis was conducted in M9 minimal media (1×M9 salts, 0.2% Casamino Acids, 2 mM $MgSO^4$, 0.1 mM $CaCl^2$, 1 mM Thiamine HCl) containing glycerol (0.4%) as the primary carbon source. 1% arabinose and variable amounts of maltose monohydrate and isopropyl β-D-1-thiogalactopyranoside (IPTG) were added as indicated. M9 medium containing both Ampicillin and Kanamycin was used to maintain the strains that contained both a reporter plasmid and a biosensor plasmid.

Plasmid Construction.

Figure 6:
FIG. 6. Plasmid maps of representative plasmids used in this study. pAY242 is the pBAD (arabinose-inducible) vector expressing the BCR-ABL1 zinc finger and mCherry (co-cistronically). This is a high copy plasmid (ColE1 origin) and contains the KanR resistance marker. pAY268 is a representative reporter plasmid with the Go3 promoter, driving the expression of EGFP. This is a medium copy plasmid (pA15 origin) and contains the $Amp^R$ resistance marker. pAY419 drives expression of the SP biosensor (and mCherry, co-cistronically) from the pTrc2 promoter (which is IPTG-inducible). The site at which MBP is split via the BCR1 insertion is indicated on this map. This is a high copy plasmid (ColE1 origin) and contains the $Kan^R$ resistance marker.
Figure 6:
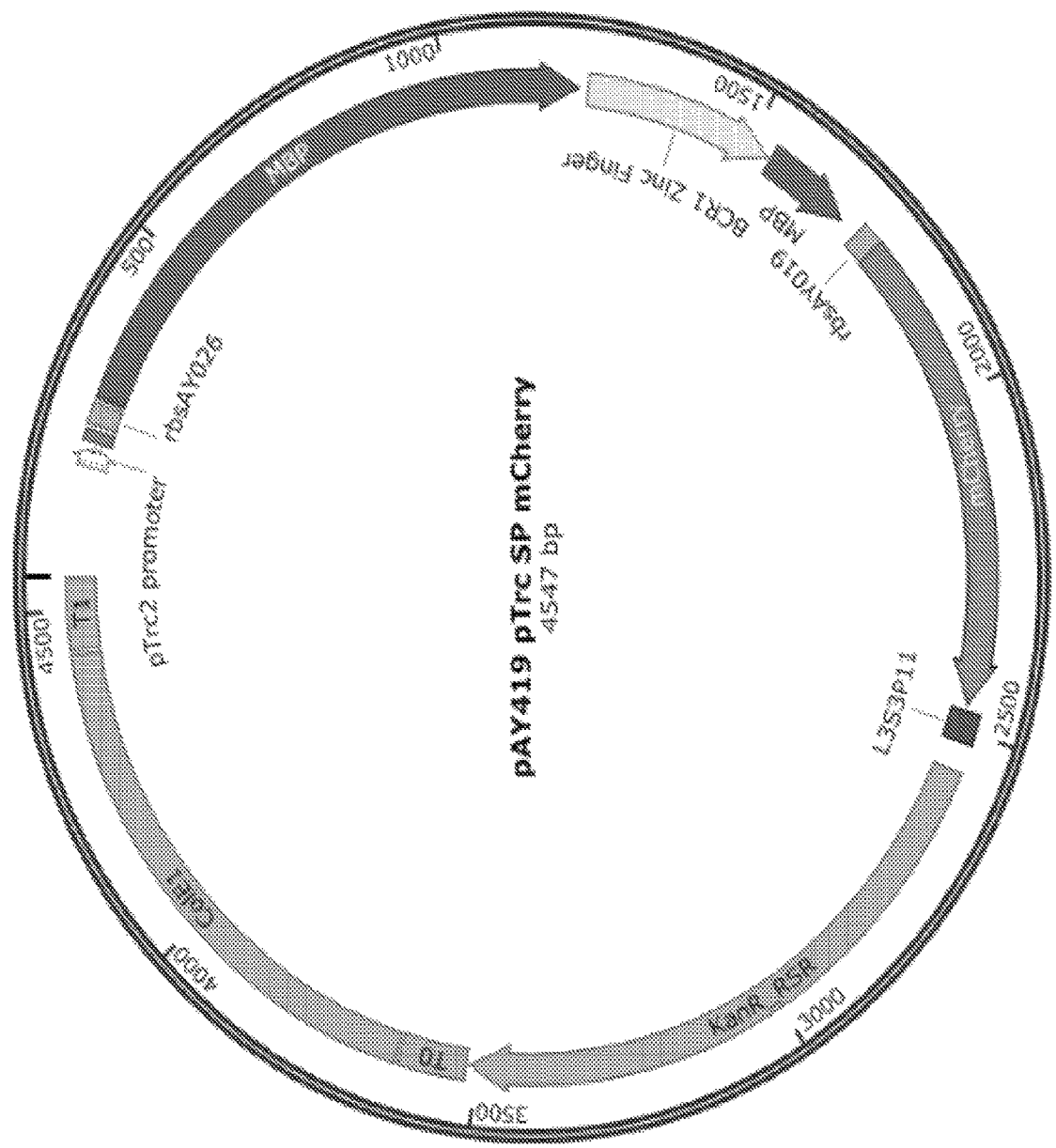
Figure 6:
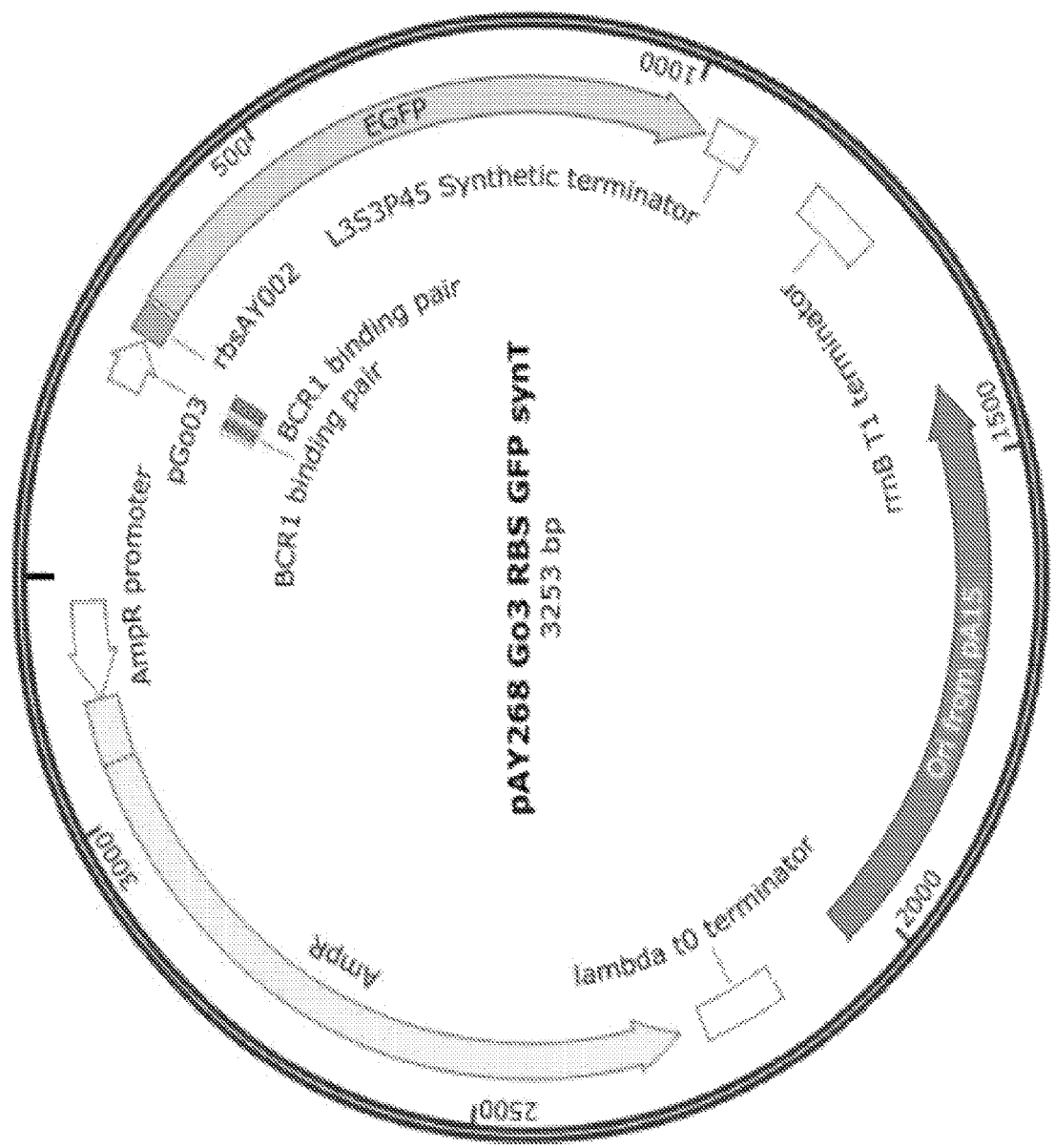

All plasmids were assembled using standard molecular biology techniques. Plasmid backbones containing "plug-and-play" multiple cloning sites and compatible plasmids containing synthetic parts (mCherry, GFPmut3b, pBAD, AraC, pTrc2) were generously provided by Jim Collins (MIT)[85]. Custom RBS sequences were designed using the RBS Calculator[86]. The pA15 low copy number origin was obtained from the Registry of Standard Biological Parts, plasmid pSB3K3. Template sequences derived from published descriptions were used for terminators[87], BCR-ABL1[55], and the Zif268 portion of human EGR1[88] (AddGene #52724). MBP was PCR amplified directly from TOP10 genomic DNA. The library of constitutive reporters was cloned in a low copy number pA15 backbone (~10 copies per cell) with the ampicillin resistance cassette. All of the pBAD-based inducible ZFP and pTrc-based inducible biosensor expression constructs included a ColE1 backbone (~300 copies per cell) and kanamycin resistance cassette. The mCherry gene was cloned behind each ZFP or biosensor gene to act as a co-cistronic reporter to confirm arabinose and IPTG mediated induction of gene expression. Representative plasmid maps are included in FIG. 6.

Microplate-Based Fluorescence Assays and Analysis.

Cultures were inoculated from single colonies into 2 mL of M9 media and grown overnight to stationary phase. Overnight cultures were diluted 1:20 and grown into exponential phase ($OD_{600}$~0.5). Cultures were again diluted to an $OD_{600}$~0.05, plated in black-walled clear bottom 96-well plates in biological triplicate, and induced with 1% arabinose (to drive expression of the ZFP) or IPTG as indicated (to drive expression of the biosensor), +/−maltose as specified. In each experiment, IPTG-induced expression of biosensor constructs was confirmed via the co-cistronic expression of mCherry (data not shown). Plates with lids were incubated and shaken in a continuous double orbital pattern at 548 cpm (2 mm) inside a BioTek Synergy H1 plate reader for 10 h with GFP, mCherry, and $OD_{600}$ measurements taken every 15 min. Monochrometer settings were 481/511 nm for GFP and 585/620 nm for mCherry.

To quantify reporter output, GFP fluorescence per $OD_{600}$ was quantified and averaged over 7 time points that span ~1.5 h of exponential growth (unless otherwise indicated). The specific fluorescence of each sample was defined as the mean ($GFP/OD_{600}$) averaged across these 7 time points, and this specific fluorescence was averaged across 3 biological replicate samples. To quantify fluorescence attributable to GFP, each sample was background-subtracted using a control sample comprising cells expressing no fluorescent proteins. To enable comparisons between promoters, each specific fluorescence value from the arabinose or IPTG-induced condition was normalized to the specific fluorescence of the uninduced condition, yielding "relative specific fluorescence". To normalize this metric of promoter performance to the base case, the relative specific fluorescence calculated for each promoter-ZFP (or promoter-biosensor) combination was then normalized to the same value calculated for that repressor using the "No sites" promoter, yielding a quantity we termed, "relative expression". This normalization strategy was utilized in order to implicitly correct for any minor effects that arabinose, IPTG, or maltose many confer on $GFP/OD_{600}$ in a manner that is unrelated to expression of the ZFP or biosensor. Thus, when quantifying biosensor performance, relevant control samples for the "+maltose" case (e.g., the uninduced case and No sites control case) were also quantified in the presence of maltose. For each metric, error was propagated according to the division rule to generate reported standard deviations.

Flow Cytometry.

Flow cytometry was used to quantify fluorescent reporter output on a single cell basis. Cells were grown and induced as described for the microplate-based fluorescence assays. Samples were collected after 5 hours of growth. Cells were then placed on ice, diluted 1:2 in chilled phosphate buffer saline (PBS) supplemented with 5 mM EDTA, and analyzed on an LSR II flow cytometer (BD). A minimum of 100,000 events were collected per sample. Mean fluorescent intensity was calculated using a minimum of 20,000 cells per sample using FlowJo software (Treestar), and relative expression calculations and error propagation were conducted as described for the microplate assays.

Statistical Analysis of Promoter Design Features.

In order to use computational analysis to compare promoter designs, it was necessary to define quantitative descriptors, or features, that capture distinguishing architectural aspects of each promoter. Because our goal was to elucidate general design principles, we chose to limit our features to those describing the quantity and location of the various 9 bp ZFP binding sites. Following this approach, we defined 17 features that describe the locations of ZFP binding sites relative to both the −10 box (TATA box) and −35 region and relative positioning amongst the ZFP binding sites. In order to determine which promoter features were important for explaining variation in performance between promoters, several feature selection methods were applied to each set of input and output data (both of which were mean-centered and variance-scaled) to generate rankings of feature importance, noting that feature independence was not assumed. For these analyses, features always served as the regression inputs. The output was the "repressibility", which we defined as the negative of relative expression, such that a promoter-ZFP combination with a high repressibility exhibits low relative expression.

Three feature selection techniques were utilized: partial least squares regression (PLSR), Random Forest, and Lasso. PLSR was executed using the built-in MATLAB function, plsregress. To determine feature importance, a permutation test was used[58]. Briefly, the output vector was randomly permuted, and PLSR was executed for this meaningless output vector, such that when this process was repeated multiple times, we calculated the standard deviation associated with each coefficient (one coefficient per feature); thereby, the ratio of true coefficient magnitude to the standard deviation associated with this coefficient provided a metric by which features can be ranked in order of importance. To implement the Random Forest method, we modified a MATLAB script developed by Jaiantilal (http://code.google.com/p/randoinforest-matlab/), which was based upon a method originally described by Breiman and Cutler (http://www.stat.berkeley.edu/~breiman/RandomForests/). The last feature selection method used was Lasso regression, also known as sparse or regularized regression[59]. Lasso feature selection is generally considered more robust than a permutation test or Random Forest, because the selection is built into model generation and does not require removing features from a predictive model. Each of these methods is described in full detail below.

Statistical Analysis of Promoter Design Features.

In order to apply computational methods to describe the library of promoters, it was necessary to choose quantitative descriptors, or features, that describe architectural properties of each promoter. We chose 17 features to describe the location of binding sites, relative to the −10 and −35 boxes, and to other binding sites. Two assumptions are associated with our choice of features. First, features were not assumed to be independent. Second, the expression of the reporter gene was assumed to depend solely on the repression of a bound biosensor or zinc finger protein.

In order to determine which promoter features are important, three feature selection methods were used. All three methods used the same input and output data to generate a ranking of feature importance. All data were mean-centered and variance-scaled before these methods were applied. Input data consisted of a matrix of promoter indices and feature variables (62 promoter indices in rows, 17 feature variables in columns). Output data are described above. The "repressibility" value for each promoter was defined as the negative relative expression of the reporter gene (GFP).

The following three feature selection techniques generated rankings of the features in order of importance.

Partial Least Squares Regression.

The first feature selection method used was a permutation test using partial least squares regression (PLSR). First, PLSR was executed using the built-in MATLAB function, plsregress. This function returns a predictive model for the output values through regression coefficients for each feature. To determine feature importance, a permutation test was used (Janes et al., 2004). The output vector was randomly permuted, and PLSR was executed for the meaningless output vector. Regression coefficients were recorded for 1000 permutations, and a mean and standard deviation was calculated for the coefficient for each feature. After many permutations, coefficient means approached zero, as is expected for random permutations, but the standard deviations associated with each coefficient approached a different finite value for each feature, which indicates the degree to which that coefficient fluctuates randomly. Features for which the coefficients were greater in magnitude than the random variance are likely to be more significant. Therefore, the ratio of coefficient magnitude to the standard deviation associated with each coefficient provided a metric by which features were ranked in order of importance. In addition to rankings described in the main text (FIG. 3), coefficients and standard deviations for each feature are reported FIG. 10.

The MATLAB function, plsregress, also provides a vector of output variance explained by each feature. Summing these gives the overall variance explained in the output data by the regression. PLSR was executed with one feature removed, and the loss of output variance explained was recorded for each feature. It is important to note that ranking through this loss of output variance explained, or loss of predictive power, yields the same ranking as the permutation test. Using this ranking, PLSR was executed with an increasing number of features, in order of importance, with the output variance explained recorded each time. The output variance explained was also recorded for an increasing number of principal components used in the regression. These both were plotted to show the contribution of each feature or principal component to the regression model (FIG. 3B).

Random Forest.

The second feature selection method utilized was Random Forest. To implement the Random Forest method, we modified a MATLAB script developed by Jaiantilal (https://code.google.com/p/randomforest-matlab/), which was based upon a method originally described by Breiman and Cutler (http://www.stat.berkeley.edu/~breiman/RandomForests/). First, the promoter library was divided into 54 promoters selected randomly to comprise a training set, leaving 8 promoters as a test set. Next, 6 features were "bagged" into a subset by random selection without replacement. The size of this subset is traditionally one third of the total set of features, which in this case rounds to 6 features (http://statweb.stanford.edu/~tibs/ElemStatLearn/). Next, a subset of promoters from the training set was randomly selected with replacement. The size of this subset is similarly one third of the total number of promoters in the training set, yielding an 18 promoter subset. A decision tree was then generated, its predictions were tested against the data from the test set of promoters, and the mean square error was recorded. This process was repeated for a large number of bagged promoter training sets, while retaining the same subset of 6 features. This overall sequence was then repeated for a large number of feature subsets, generating a total of 100 decision trees, each of which used the same test set. Finally, this entire process was repeated for 100 different random choices of test set, generating a total of 10,000 decision trees. To assess the importance of a feature, the input data within the test set were perturbed such that the feature values associated with each promoter (e.g., number of ZFP binding sites) were randomly permuted by shuffling. Any decision tree that included the feature of interest was then retested using the perturbed input data. The increase in mean squared error (i.e., reduction in predictive power) was averaged over all trees containing this feature. This metric (average increase in mean square error) was thus used to generate a ranking of features by importance, such that features with a greater average increase in mean square error were ranked as more important. (FIG. 10).

Lasso Regression.

The last feature selection method used was Lasso regression, also known as sparse or regularized regression. This type of feature selection is generally considered more robust than a permutation test or random forest, because the selection is built into the model generation, and does not require removing features from a predictive model (Tibshirani, R. (1996)). Lasso regression uses the least squares method, and is regularized by placing a constraint on the sum of the absolute value of the regression coefficients. Mathematically, the method places a penalty on large coefficient magnitudes by minimizing the following expression:

$$\sum_{i=1}^{N}\left(y_i - \sum_j \beta_j x_{ij}\right)^2 + \lambda \sum_j |\beta_j|$$

In this expression, yi represents output data for the ith promoter, β is the regression coefficient for the jth feature, and xij is input data (feature variable j for promoter i). The value of λ is a tunable parameter that determines the extent of regularization. With this method, coefficients of unimportant features shrink to zero as λ is increased. Using the MATLAB function, lasso, Lasso regression was executed for 100 increasing values of lambda, with the number of features with non-zero coefficients shrinking from 17 to 0. Each regression iteration (corresponding to each value of λ) was tested using 10-fold cross validation, and a mean squared error was recorded for each iteration. For each feature, the number of regression iterations for which it had a non-zero coefficient was recorded. This metric was used to generate a ranking of features in order of importance, with the most important features having non-zero coefficients for larger values of A. In addition to the feature ranking, the mean squared error and number of features with non-zero coefficients were plotted together versus the value of λ (FIG. 3C).

Abbreviations
MBP—Maltose binding protein
ZFP—Zinc finger protein
TALE—Transcription activator-like effector
PLSR—Partial Least squares regression
MSE—Mean squared error
BLA—Beta-lactamase
SZF—Split zinc finger
SP—Split protein
IPTG—Isopropyl β-D-1-thiogalactopyranoside
LB—Lysogeny broth
OD—Optical density at 600 nm

REFERENCES

[1] Michener, J. K., Thodey, K., Liang, J. C., and Smolke, C. D. (2012) Applications of genetically-encoded biosensors for the construction and control of biosynthetic pathways, Metab Eng 14, 212-222.

[2] Kang, Z., Zhang, C., Zhang, J., Jin, P., Zhang, J., Du, G., and Chen, J. (2014) Small RNA regulators in bacteria: powerful tools for metabolic engineering and synthetic biology, Applied microbiology and biotechnology 98, 3413-3424.

[3] Zhou, L. B., and Zeng, A. P. (2015) Exploring Lysine Riboswitch for Metabolic Flux Control and Improvement of 1-Lysine Synthesis in Corynebacterium glutamicum, ACS Synth Biol 4, 729-734.

[4] Raman, S., Rogers, J. K., Taylor, N. D., and Church, G. M. (2014) Evolution-guided optimization of biosynthetic pathways, Proc Natl Acad Sci USA 111, 17803-17808.

[5] Rogers, J. K., Guzman, C. D., Taylor, N. D., Raman, S., Anderson, K., and Church, G. M. (2015) Synthetic biosensors for precise gene control and real-time monitoring of metabolites, Nucleic Acids Res.

[6] Dietrich, J. A., Shis, D. L., Alikhani, A., and Keasling, J. D. (2013) Transcription factor-based screens and synthetic selections for microbial small-molecule biosynthesis, ACS Synth Biol 2, 47-58.

[7] Zhang, F., Carothers, J. M., and Keasling, J. D. (2012) Design of a dynamic sensor-regulator system for production of chemicals and fuels derived from fatty acids, Nat Biotechnol 30, 354-359.

[8] Golynskiy, M. V., Koay, M. S., Vinkenborg, J. L., and Merkx, M. (2011) Engineering protein switches: sensors, regulators, and spare parts for biology and biotechnology, Chembiochem 12, 353-361.

[9] Li, S., Si, T., Wang, M., and Zhao, H. (2015) Development of a Synthetic Malonyl-CoA Sensor in Saccharomyces cerevisiae for Intracellular Metabolite Monitoring and Genetic Screening, ACS Synth Biol.

[10] Zhao, Y., and Yang, Y. (2015) Profiling metabolic states with genetically encoded fluorescent biosensors for NADH, Curr Opin Biotechnol 31, 86-92.

[11] Brockman, I. M., and Prather, K. L. (2015) Dynamic metabolic engineering: New strategies for developing responsive cell factories, Biotechnol J.

[12] Watstein, D. M., McNerney, M. P., and Styczynski, M. P. (2015) Precise metabolic engineering of carotenoid biosynthesis in Escherichia coli towards a low-cost biosensor, Metab Eng.

[13] Venayak, N., Anesiadis, N., Cluett, W. R., and Mahadevan, R. (2015) Engineering metabolism through dynamic control, Curr Opin Biotechnol 34C, 142-152.

[14] Dahl, R. H., Zhang, F., Alonso-Gutierrez, J., Baidoo, E., Batth, T. S., Redding-Johanson, A. M., Petzold, C. J., Mukhopadhyay, A., Lee, T. S., Adams, P. D., and Keasling, J. D. (2013) Engineering dynamic pathway regulation using stress-response promoters, Nat Biotechnol 31, 1039-1046.

[15] Liu, D., Xiao, Y., Evans, B. S., and Zhang, F. (2015) Negative feedback regulation of fatty acid production based on a malonyl-CoA sensor-actuator, ACS Synth Biol 4, 132-140.

[16] Farmer, W. R., and Liao, J. C. (2000) Improving lycopene production in Escherichia coli by engineering metabolic control, Nat Biotechnol 18, 533-537.

[17] Tang, S. Y., and Cirino, P. C. (2011) Design and application of a mevalonate-responsive regulatory protein, Angew Chem Int Ed Engl 50, 1084-1086.

[18] Tang, S. Y., Qian, S., Akinterinwa, O., Frei, C. S., Gredell, J. A., and Cirino, P. C. (2013) Screening for enhanced triacetic acid lactone production by recombinant Escherichia coli expressing a designed triacetic acid lactone reporter, J Am Chem Soc 135, 10099-10103.

[19] Yang, J., Seo, S. W., Jang, S., Shin, S. I., Lim, C. H., Roh, T. Y., and Jung, G. Y. (2013) Synthetic RNA devices to expedite the evolution of metabolite-producing microbes, Nature communications 4, 1413.

[20] Binder, S., Schendzielorz, G., Stabler, N., Krumbach, K., Hoffmann, K., Bott, M., and Eggeling, L. (2012) A high-throughput approach to identify genomic variants of bacterial metabolite producers at the single-cell level, Genome biology 13, R40.

[21] Zhang, F., and Keasling, J. (2011) Biosensors and their applications in microbial metabolic engineering, Trends Microbiol 19, 323-329.

[22] Dietrich, J. A., McKee, A. E., and Keasling, J. D. (2010) High-throughput metabolic engineering: advances in small-molecule screening and selection, Annu Rev Biochem 79, 563-590.

[23] Edwards, W. R., Busse, K., Allemann, R. K., and Jones, D. D. (2008) Linking the functions of unrelated proteins using a novel directed evolution domain insertion method, Nucleic Acids Res 36, e78.

[24] Guntas, G., Mitchell, S. F., and Ostermeier, M. (2004) A molecular switch created by in vitro recombination of nonhomologous genes, Chem Biol 11, 1483-1487.

[25] Guntas, G., and Ostermeier, M. (2004) Creation of an allosteric enzyme by domain insertion, J Mol Biol 336, 263-273.

[26] Meister, G. E., and Joshi, N. S. (2013) An engineered calmodulin-based allosteric switch for Peptide biosensing, Chembiochem 14, 1460-1467.

[27] Qi, L., Lucks, J. B., Liu, C. C., Mutalik, V. K., and Arkin, A. P. (2012) Engineering naturally occurring trans-acting non-coding RNAs to sense molecular signals, Nucleic Acids Res 40, 5775-5786.

[28] Jeong, J., Kim, S. K., Ahn, J., Park, K., Jeong, E. J., Kim, M., and Chung, B. H. (2006) Monitoring of conformational change in maltose binding protein using split green fluorescent protein, Biochem Biophys Res Commun 339, 647-651.

[29] Wang, B., Barahona, M., Buck, M., and Schumacher, J. (2013) Rewiring cell signalling through chimaeric regulatory protein engineering, Biochem Soc Trans 41, 1195-1200.

[30] Miyawaki, A., Llopis, J., Heim, R., McCaffery, J. M., Adams, J. A., Ikura, M., and Tsien, R. Y. (1997) Fluorescent indicators for Ca2+ based on green fluorescent proteins and calmodulin, Nature 388, 882-887.

[31] Liu, D., Evans, T., and Zhang, F. (2015) Applications and advances of metabolite biosensors for metabolic engineering, Metab Eng.

[32] Strianese, M., Staiano, M., Ruggiero, G., Labella, T., Pellecchia, C., and D'Auria, S. (2012) Fluorescence-based biosensors, Methods Mol Biol 875, 193-216.

[33] Oldach, L., and Zhang, J. (2014) Genetically encoded fluorescent biosensors for live-cell visualization of protein phosphorylation, Chem Biol 21, 186-197.

[34] Park, K. S., Lee, D. K., Lee, H., Lee, Y., Jang, Y. S., Kim, Y. H., Yang, H. Y., Lee, S. I., Seol, W., and Kim, J. S. (2003) Phenotypic alteration of eukaryotic cells using randomized libraries of artificial transcription factors, Nat Biotechnol 21, 1208-1214.

[35] Bae, K. H., Kwon, Y. D., Shin, H. C., Hwang, M. S., Ryu, E. H., Park, K. S., Yang, H. Y., Lee, D. K., Lee, Y., Park, J., Kwon, H. S., Kim, H. W., Yeh, B. I., Lee, H. W., Sohn, S. H., Yoon, J., Seol, W., and Kim, J. S. (2003) Human zinc fingers as building blocks in the construction of artificial transcription factors, Nat Biotechnol 21, 275-280.

[36] Lee, J. Y., Sung, B. H., Yu, B. J., Lee, J. H., Lee, S. H., Kim, M. S., Koob, M. D., and Kim, S. C. (2008) Phenotypic engineering by reprogramming gene transcription using novel artificial transcription factors in Escherichia coli, Nucleic Acids Res 36, e102.

[37] Copeland, M. F., Politz, M. C., and Pfleger, B. F. (2014) Application of TALEs, CRISPR/Cas and sRNAs as trans-acting regulators in prokaryotes, Curr Opin Biotechnol 29, 46-54.

[38] Bogdanove, A. J., and Voytas, D. F. (2011) TAL effectors: customizable proteins for DNA targeting, Science 333, 1843-1846.

[39] Cermak, T., Doyle, E. L., Christian, M., Wang, L., Zhang, Y., Schmidt, C., Baller, J. A., Somia, N. V., Bogdanove, A. J., and Voytas, D. F. (2011) Efficient design and assembly of custom TALEN and other TAL effector-based constructs for DNA targeting, Nucleic Acids Res 39, e82.

[40] Oakes, B. L., Nadler, D. C., Flamholz, A., Fellmann, C., Staahl, B. T., Doudna, J. A., and Savage, D. F. (2016) Profiling of engineering hotspots identifies an allosteric CRISPR-Cas9 switch, Nat Biotechnol 34, 646-651.

[41] Shis, D. L., Hussain, F., Meinhardt, S., Swint-Kruse, L., and Bennett, M. R. (2014) Modular, multi-input transcriptional logic gating with orthogonal LacI/GalR family chimeras, ACS Synth Biol 3, 645-651.

[42] Meinhardt, S., Manley, M. W., Jr., Becker, N. A., Hessman, J. A., Maher, L. J., 3rd, and Swint-Kruse, L. (2012) Novel insights from hybrid LacI/GalR proteins: family-wide functional attributes and biologically significant variation in transcription repression, Nucleic Acids Res 40, 11139-11154.

[43] Benson, D. E., Conrad, D. W., de Lorimier, R. M., Trammell, S. A., and Hellinga, H. W. (2001) Design of bioelectronic interfaces by exploiting hinge-bending motions in proteins, Science 293, 1641-1644.

[44] Benson, D. E., Haddy, A. E., and Hellinga, H. W. (2002) Converting a maltose receptor into a nascent binuclear copper oxygenase by computational design, Biochemistry 41, 3262-3269.

[45] Marvin, J. S., Corcoran, E. E., Hattangadi, N. A., Zhang, J. V., Gere, S. A., and Hellinga, H. W. (1997) The rational design of allosteric interactions in a monomeric protein and its applications to the construction of biosensors, Proc Natl Acad Sci USA 94, 4366-4371.

[46] Marvin, J. S., and Hellinga, H. W. (2001) Conversion of a maltose receptor into a zinc biosensor by computational design, Proc Natl Acad Sci USA 98, 4955-4960.

[47] Collins, C. H., Arnold, F. H., and Leadbetter, J. R. (2005) Directed evolution of Vibrio fischeri LuxR for increased sensitivity to a broad spectrum of acyl-homoserine lactones, Mol Microbiol 55, 712-723.

[48] Tinberg, C. E., Khare, S. D., Dou, J., Doyle, L., Nelson, J. W., Schena, A., Jankowski, W., Kalodimos, C. G., Johnsson, K., Stoddard, B. L., and Baker, D. (2013) Computational design of ligand-binding proteins with high affinity and selectivity, Nature 501, 212-216.

[49] Feng, J., Jester, B. W., Tinberg, C. E., Mandell, D. J., Antunes, M. S., Chari, R., Morey, K. J., Rios, X., Medford, J. I., Church, G. M., Fields, S., and Baker, D. (2015) A general strategy to construct small molecule biosensors in eukaryotes, Elife 4.

[50] Hurt, J. A., Thibodeau, S. A., Hirsh, A. S., Pabo, C. O., and Joung, J. K. (2003) Highly specific zinc finger proteins obtained by directed domain shuffling and cell-based selection, Proc Natl Acad Sci USA 100, 12271-12276.

[51] Wright, D. A., Thibodeau-Beganny, S., Sander, J. D., Winfrey, R. J., Hirsh, A. S., Eichtinger, M., Fu, F., Porteus, M. H., Dobbs, D., Voytas, D. F., and Joung, J. K. (2006) Standardized reagents and protocols for engineering zinc finger nucleases by modular assembly, Nature protocols 1, 1637-1652.

[52] Maeder, M. L., Thibodeau-Beganny, S., Osiak, A., Wright, D. A., Anthony, R. M., Eichtinger, M., Jiang, T., Foley, J. E., Winfrey, R. J., Townsend, J. A., Unger-Wallace, E., Sander, J. D., Muller-Lerch, F., Fu, F.,

[52] Pearlberg, J., Gobel, C., Dassie, J. P., Pruett-Miller, S. M., Porteus, M. H., Sgroi, D. C., Iafrate, A. J., Dobbs, D., McCray, P. B., Jr., Cathomen, T., Voytas, D. F., and Joung, J. K. (2008) Rapid "open-source" engineering of customized zinc-finger nucleases for highly efficient gene modification, Molecular cell 31, 294-301.

[53] Khalil, A. S., Lu, T. K., Bashor, C. J., Ramirez, C. L., Pyenson, N. C., Joung, J. K., and Collins, J. J. (2012) A synthetic biology framework for programming eukaryotic transcription functions, Cell 150, 647-658.

[54] Hashimoto, H., Olanrewaju, Y. O., Zheng, Y., Wilson, G. G., Zhang, X., and Cheng, X. (2014) Wilms tumor protein recognizes 5-carboxylcytosine within a specific DNA sequence, Genes Dev 28, 2304-2313.

[55] Lohmueller, J. J., Armel, T. Z., and Silver, P. A. (2012) A tunable zinc finger-based framework for Boolean logic computation in mammalian cells, Nucleic Acids Res 40, 5180-5187.

[56] Deaner, M., and Alper, H. S. (2016) Promoter and Terminator Discovery and Engineering, Adv Biochem Eng Biotechnol.

[57] Blazeck, J., and Alper, H. S. (2013) Promoter engineering: recent advances in controlling transcription at the most fundamental level, Biotechnol J 8, 46-58.

[58] Janes, K. A., Kelly, J. R., Gaudet, S., Albeck, J. G., Sorger, P. K., and Lauffenburger, D. A. (2004) Cue-signal-response analysis of TNF-induced apoptosis by partial least squares regression of dynamic multivariate data, J Comput Biol 11, 544-561.

[59] Tibshirani, R. (1996) Regression shrinkage and selection via the Lasso, J Roy Stat Soc B Met 58, 267-288.

[60] Quiocho, F. A., Spurlino, J. C., and Rodseth, L. E. (1997) Extensive features of tight oligosaccharide binding revealed in high-resolution structures of the maltodextrin transport/chemosensory receptor, Structure 5, 997-1015.

[61] Sharff, A. J., Rodseth, L. E., and Quiocho, F. A. (1993) Refined 1.8-A structure reveals the mode of binding of beta-cyclodextrin to the maltodextrin binding protein, Biochemistry 32, 10553-10559.

[62] Sharff, A. J., Rodseth, L. E., Spurlino, J. C., and Quiocho, F. A. (1992) Crystallographic evidence of a large ligand-induced hinge-twist motion between the two domains of the maltodextrin binding protein involved in active transport and chemotaxis, Biochemistry 31, 10657-10663.

[63] Spurlino, J. C., Lu, G. Y., and Quiocho, F. A. (1991) The 2.3-A resolution structure of the maltose- or maltodextrin-binding protein, a primary receptor of bacterial active transport and chemotaxis, J Biol Chem 266, 5202-5219.

[64] Spurlino, J. C., Rodseth, L. E., and Quiocho, F. A. (1992) Atomic interactions in protein-carbohydrate complexes. Tryptophan residues in the periplasmic maltodextrin receptor for active transport and chemotaxis, J Mol Biol 226, 15-22.

[65] Riggs, P. D. (2012) Engineered Derivatives of Maltose-Binding Protein, In Protein Engineering (Kaumaya, P., Ed.), InTech.

[66] Fehr, M., Frommer, W. B., and Lalonde, S. (2002) Visualization of maltose uptake in living yeast cells by fluorescent nanosensors, Proc Natl Acad Sci USA 99, 9846-9851.

[67] Fehr, M., Okumoto, S., Deuschle, K., Lager, I., Looger, L. L., Persson, J., Kozhukh, L., Lalonde, S., and Frommer, W. B. (2005) Development and use of fluorescent nanosensors for metabolite imaging in living cells, Biochem Soc Trans 33, 287-290.

[68] Kaper, T., Lager, I., Looger, L. L., Chermak, D., and Frommer, W. B. (2008) Fluorescence resonance energy transfer sensors for quantitative monitoring of pentose and disaccharide accumulation in bacteria, Biotechnol Biofuels 1, 11.

[69] Ha, J. S., Song, J. J., Lee, Y. M., Kim, S. J., Sohn, J. H., Shin, C. S., and Lee, S. G. (2007) Design and application of highly responsive fluorescence resonance energy transfer biosensors for detection of sugar in living *Saccharomyces cerevisiae* cells, Appl Environ Microbiol 73, 7408-7414.

[70] Meister, G. E., Chandrasegaran, S., and Ostermeier, M. (2008) An engineered split M.HhaI-zinc finger fusion lacks the intended methyltransferase specificity, Biochem Biophys Res Commun 377, 226-230.

[71] Ke, W., Laurent, A. H., Armstrong, M. D., Chen, Y., Smith, W. E., Liang, J., Wright, C. M., Ostermeier, M., and van den Akker, F. (2012) Structure of an engineered beta-lactamase maltose binding protein fusion protein: insights into heterotropic allosteric regulation, PLoS One 7, e39168.

[72] Martineau, P., Szmelcman, S., Spurlino, J. C., Quiocho, F. A., and Hofnung, M. (1990) Genetic approach to the role of tryptophan residues in the activities and fluorescence of a bacterial periplasmic maltose-binding protein, J Mol Biol 214, 337-352.

[73] Kamionka, A., Bogdanska-Urbaniak, J., Scholz, O., and Hillen, W. (2004) Two mutations in the tetracycline repressor change the inducer anhydrotetracycline to a corepressor, Nucleic Acids Res 32, 842-847.

[74] Ramos, J. L., Martinez-Bueno, M., Molina-Henares, A. J., Teran, W., Watanabe, K., Zhang, X., Gallegos, M. T., Brennan, R., and Tobes, R. (2005) The TetR family of transcriptional repressors, Microbiol Mol Biol Rev 69, 326-356.

[75] Pabo, C. O., Peisach, E., and Grant, R. A. (2001) Design and selection of novel Cys2His2 zinc finger proteins, Annu Rev Biochem 70, 313-340.

[76] Makhlynets, O. V., Raymond, E. A., and Korendovych, I. V. (2015) Design of allosterically regulated protein catalysts, Biochemistry 54, 1444-1456.

[77] Yu, K., Liu, C., Kim, B. G., and Lee, D. Y. (2015) Synthetic fusion protein design and applications, Biotechnol Adv 33, 155-164.

[78] Mehta, M. M., Liu, S., and Silberg, J. J. (2012) A transposase strategy for creating libraries of circularly permuted proteins, Nucleic Acids Res 40, e71.

[79] Ostermeier, M. (2005) Engineering allosteric protein switches by domain insertion, Protein Eng Des Sel 18, 359-364.

[80] Topilina, N. I., and Mills, K. V. (2014) Recent advances in in vivo applications of intein-mediated protein splicing, Mob DNA 5, 5.

[81] Tullman, J., Nicholes, N., Dumont, M. R., Ribeiro, L. F., and Ostermeier, M. (2016) Enzymatic protein switches built from paralogous input domains, Biotechnol Bioeng 113, 852-858.

[82] Green, A. A., Silver, P. A., Collins, J. J., and Yin, P. (2014) Toehold switches: de-novo-designed regulators of gene expression, Cell 159, 925-939.

[83] Nistala, G. J., Wu, K., Rao, C. V., and Bhalerao, K. D. (2010) A modular positive feedback-based gene amplifier, J Biol Eng 4, 4.

[84] Wang, H. H., Isaacs, F. J., Carr, P. A., Sun, Z. Z., Xu, G., Forest, C. R., and Church, G. M. (2009) Programming cells by multiplex genome engineering and accelerated evolution, Nature 460, 894-898.

[85] Litcofsky, K. D., Afeyan, R. B., Krom, R. J., Khalil, A. S., and Collins, J. J. (2012) Iterative plug-and-play methodology for constructing and modifying synthetic gene networks, Nat Methods 9, 1077-1080.

[86] Salis, H. M., Mirsky, E. A., and Voigt, C. A. (2009) Automated design of synthetic ribosome binding sites to control protein expression, Nat Biotechnol 27, 946-950.

[87] Chen, Y. J., Liu, P., Nielsen, A. A., Brophy, J. A., Clancy, K., Peterson, T., and Voigt, C. A. (2013) Characterization of 582 natural and synthetic terminators and quantification of their design constraints, Nat Methods 10, 659-664.

[88] Worringer, K. A., Rand, T. A., Hayashi, Y., Sami, S., Takahashi, K., Tanabe, K., Narita, M., Srivastava, D., and Yamanaka, S. (2014) The let-7/LIN-41 pathway regulates reprogramming to human induced pluripotent stem cells by controlling expression of prodifferentiation genes, Cell Stem Cell 14, 40-52.

Example 2

Title: Development of Novel Metabolite-Responsive Transcription Factors Via Transposon-Mediated Protein Fusion Abstract Naturally evolved metabolite-responsive biosensors enable applications in metabolic engineering, ranging from screening large genetic libraries to dynamically regulating biosynthetic pathways. However, there are many metabolites for which a natural biosensor does not exist. To address this need, we developed a general method for converting metabolite-binding proteins into metabolite-responsive transcription factors—Biosensor Engineering by Random Domain Insertion (BERDI). This approach takes advantage of an unbiased in vitro transposon insertion reaction to generate all possible insertions of a DNA-binding domain into a metabolite-binding protein, followed by fluorescence activated cell sorting (FACS) to isolate functional biosensors. To develop and evaluate the BERDI method, we generated a library of candidate biosensors in which a zinc finger DNA-binding domain was inserted into maltose binding protein, which served as a model well-studied metabolite binding protein. Library diversity was characterized by several methods, a selection scheme was deployed, and ultimately several distinct and functional maltose-responsive transcriptional biosensors were identified. The BERDI method comprises a generalizable strategy that may ultimately be applied to convert a wide range of metabolite-binding proteins into novel biosensors for applications in metabolic engineering and synthetic biology.

Introduction

Metabolite-responsive biosensors have a wide variety of uses, from basic research and discovery, to diagnostics, to engineered biosynthesis (Khalil and Collins, 2010). Such biosensors include diverse sensing and output modalities, including fluorescent and FRET-based biosensors (Golynskiy et al., 2011, Strianese et al., 2012), RNA-based biosensors (Kang et al., 2014, Michener et al., 2012), and transcription factor biosensors (Brockman and Prather, 2015, Dietrich et al., 2010, Venayak et al., 2015). Transcription factor biosensors have proven to be especially powerful for bioengineering, facilitating dynamic profiling of intracellular glucaric acid (Rogers et al., 2015) and malonyl-CoA (Li et al., 2015), and enabling high-throughput screening of large genetic libraries constructed to achieve biosynthesis of 1-butantol, succinate, and adipate (Dietrich et al., 2013), benzoic acids (van Sint Fiet et al., 2006), and $_L$-Lysine (Binder et al., 2012). Moreover, transcription factor biosensors have been harnessed to implement dynamic intracellular feedback control, balancing metabolic fluxes to increase production titers and yields of lycopene (Farmer and Liao, 2000), fatty acid ethyl ester (Zhang et al., 2012), amorphadiene (Dahl et al., 2013), 1-butanol (Dietrich et al., 2013), and malonyl-CoA (Liu et al., 2015). Notably, these examples relied upon naturally-evolved transcription factor biosensors, and broader utilization of such approaches is currently restricted by the limited pool of naturally evolved (and known) metabolite-responsive biosensors. Thus, approaches for generating novel metabolite biosensors are required.

Several strategies for generating new biosensors have been explored. One approach for generating new transcription factor biosensors is fusion of the ligand-binding domain from one transcription factor to the DNA-binding domain from a different transcription factor. However, these chimeric biosensors are generally limited to fusions within families of structurally-related transcription factors, such as the LacI/GalR family, in order to preserve mechanisms of ligand-responsiveness that arise from allosteric regulation (Meinhardt et al., 2012, Shis et al., 2014). An alternative approach is to fuse a metabolite-binding protein (which multimerizes upon ligand-binding) to a natural transcription factor, such as AraC, to generate chimeras in which metabolite binding modulates transcription factor activity (Chou and Keasling, 2013). Additionally, the binding pockets of transcription factors such as LuxR (Collins et al., 2005, Collins et al., 2006), AraC (Tang and Cirino, 2011, Tang et al., 2008, Tang et al., 2013), and XylR (Mohn et al., 2006) have been mutagenized and evolved to bind new, albeit structurally similar, ligands. In a recently reported strategy for engineering novel biosensors in eukaryotes, fusion proteins were engineered to be unstable in the absence of ligand, such that the addition of the ligand stabilized the protein and enabled it to carry out its functional role (Feng et al., 2015). While these findings have generated both useful biosensors and novel insights into biosensor design, most methods include some inherent limitation on the extent to which they may be generalized to build biosensors for any metabolite of interest. Therefore, there remains an outstanding need for new methods for generating novel transcription factor biosensors.

We recently reported a new strategy for converting a ligand-binding protein into a transcription factor biosensor (Younger et al., 2016). In this proof-of-principle investigation, the *Escherichia coli* maltose binding protein (MBP) was genetically fused with a modular zinc finger DNA binding domain (ZFP) to generate a novel maltose-responsive transcription factor, in which the addition of maltose alleviated transcriptional repression of an engineered promoter. This demonstration leveraged a wealth of prior knowledge pertaining to MBP; specifically the ZFP was inserted into MBP at a position that was previously identified via random fusion between MBP and TEM1 β-lactamase (bla) to generate a maltose-regulated bla (Guntas et al., 2004). Whether other fusions between MBP and a ZFP could generate a functional biosensor, and whether a functional biosensor could be generated in the absence of such prior knowledge remained open questions.

To address these questions, here we developed an efficient method for generating combinatorial fusions between a ligand-binding protein and a ZFP, followed by isolation of functional biosensors from this diverse library, which we term Biosensor Engineering by Random Domain Insertion (BERDI). To develop and validate this method, a library of fusions between a ZFP and MBP was generated, analyzed, and screened. Notably, we successfully identified three novel maltose-responsive biosensors, which validates this overall approach. Thus, BERDI comprises a generalizable strategy that may ultimately be applied to convert a wide range of metabolite-binding proteins into novel biosensors.

Materials and Methods

Bacterial Strains and Culturing.

All experiments were conducted in DS941 Z1 *Escherichia coli* cells (AB1157, recF143, lacI$^q$ lacZ ΔM15, P$_{laciq}$-LacI, P$_{N25}$-TetR). Cells were maintained in Lysogeny Broth (LB) Lennox formulation (10 g/L tryptone, 5 g/L yeast extract, 5 g/L NaCl) supplemented with appropriate antibiotics (Ampicillin 100 µg/mL, Kanamycin 50 µg/mL, and/or Chloramphenicol 34 µg/mL). All experimental analyses were conducted in M9 minimal media (1×M9 salts, 0.2% Cas amino acids, 2 mM MgSO$_4$, 0.1 mM CaCl$_2$, 1 mM Thiamine HCl) containing glycerol (0.4%) as the primary carbon source. Variable amounts of isopropyl β-D-1-thiogalactopyranoside (IPTG) were added, as indicated, to induce biosensor expression. Maltose monohydrate was added to the media at a final concentration of 100 mM, where indicated.

The biosensor expression vector was built using standard molecular biology techniques using parts (GFPmut3b and pTrc2) gifted by Jim Collins (MIT) (Litcofsky et al., 2012). The green fluorescent protein (GFP) reporter plasmid driven by the pGo92 zinc finger-responsive promoter was previously described (Younger, Dalvie, Rottinghaus and Leonard, 2016). Custom RBS sequences for the biosensor and reporter plasmids were designed using the RBS calculator (Salis et al., 2009). The camR and sacB ORFs were transferred from pKM154, which was gifted by Kenan Murphy (University of Massachusetts) (Murphy et al., 2000) (Addgene plasmid #13036), into a storage vector containing MuA transposon recognition sequences, flanked by BglII restriction sites (pAY438). The BCR-ABL1 ZFP was subcloned into a storage vector flanked by NotI restriction sites (pAY437). Description of all plasmids used in this study can be found in in Table 1 below.

TABLE 1

Plasmids used in this study

| Plasmid name | Description | Resistance | Origin | Reference |
|---|---|---|---|---|
| pAY430 | pGo92-GFP. Zinc finger repressible promoter driving GFP. | Amp$^R$ | pA15 | Younger et al., 2016 |
| pAY447 | MBP (no promoter) | Amp$^R$ | ColE1 | This work |
| pAY438 | BglII and transposon recognition sequences flanking CmR and SacB | Kan$^R$ Cm$^R$ | ColE1 | This work |
| pAY437 | BCR-ABL1 zinc finger, without a stop codon or promoter, flanked by NotI sites | Amp$^R$ | ColE1 | This work |
| pAY431 | pTrc2 promoter and RBS followed by KpnI and SphI MCS, followed by a terminator | Kan$^R$ | ColE1 | This work |
| pAY419 | 316R reference biosensor (SP from Younger et al. 2016) | Kan$^R$ | ColE1 | Younger et al., 2016 |
| pAY470 | 277A biosensor (in pAY431) | Kan$^R$ | ColE1 | This work |
| pAY451 | 270A double ZFP biosensor (in pAY431) | Kan$^R$ | ColE1 | This work |
| pAY453 | 270A single biosensor (in pAY431) | Kan$^R$ | ColE1 | This work |
| pAY452 | 335P (3AA) biosensor (in pAY431) | Kan$^R$ | ColE1 | This work |
| pAY469 | 335P (2AA) biosensor (in pAY431) | Kan$^R$ | ColE1 | This work |
| pAY468 | 335P (1AA) biosensor (in pAY431) | Kan$^R$ | ColE1 | This work |
| pAY460 | 335P (0AA) biosensor (in pAY431) | Kan$^R$ | ColE1 | This work |

Candidate Biosensor Library Construction.

The MuA transposase inserts its transposon randomly, and in either a forward or reverse direction, into any DNA sequence (Haapa et al., 1999). Furthermore, the transposon can be inserted in any of the 3 possible codon frames in MBP. A detailed description of the transposon sequence and potential scar options can be found in FIG. 20.

First, a library representing all possible random insertions within MBP was generated. Double-stranded DNA comprising a transposon conferring chloramphenicol resistance as well as containing the sacB gene for negative selection with sucrose was digested out of a storage plasmid (pAY438) using BglII, gel extracted, and cleaned by ethanol precipitation/resuspension in 40 µL of TE buffer. In vitro transposition reactions were carried out using the Mutation Generation System kit (Thermo Scientific # F701), as per the manufacturer's protocol. Briefly, 100 ng of purified transposon was mixed with 200 ng of target plasmid encoding MBP (pAY447), and the mixture was incubated with 1 µL of 0.22 ng/µL MuA transposase for 4 h at 30° C. MuA was heat-inactivated (10 min at 75° C.), and a PCR cleanup (IBI Scientific) was conducted to recover the library. The entire library was electroporated into two tubes of electrically-competent *E. coli* cells (~250 µL final volume each). Transformed cells were selected on plates containing chloramphenicol (transposon) as well as ampicillin (plasmid backbone). Serial dilutions were made at each cloning step and extrapolated to estimate library size. The MBP gene was digested out with restriction enzymes KpnI and SphI and purified by agarose gel electrophoresis to separate the band representing MBP with transposon insertion (3923 bp) from the band representing WT MBP (1122 bp). The MBP with transposon band was purified and cloned into an expression plasmid under the control of a lac-inducible promoter pTrc2 (pAY431). Finally, restriction digestion (using the NotI site present in the transposon scar) was used to replace the transposon with the sequence encoding the ZFP (BCR-ABL1), and this ligation was transformed into competent *E. coli* cells that already contained the ZFP-responsive GFP reporter plasmid (pAY430). Cells were selected with ampicillin and kanamycin for both plasmids as well as 10% sucrose to maximize loss of the transposon, yielding the naïve (unselected) candidate biosensor library.

Microplate-Based Fluorescent Assays and Analysis.

Cultures were inoculated from single colonies into 2 mL of M9 media and grown overnight to stationary phase. Overnight cultures were diluted 1:10 and grown for 1-2 h (OD600 ~0.5). Cultures were again diluted 1:10 (OD600 ~0.05), plated in black-walled clear bottom 96-well plates in biological triplicate, and induced with 30 μM IPTG and/or 100 mM maltose. Plates with lids were incubated and shaken in a continuous double orbital pattern at 548 cpm (2 mm) inside a BioTek Synergy H1 plate reader for 10 h with GFP fluorescence and OD600 absorption measurements taken every 15 min. Monochrometer settings were 485/515 nm for GFP.

Flow Cytometry and Fluorescence Activated Cell Sorting (FACS).

Overnight cultures (2 mL) were diluted 1:10 into a fresh 2 mL aliquot of M9 media and grown for 1-2 hours (OD600~0.5). Cultures were again diluted 1:10 (OD600~0.05) in a fresh 2 mL of either M9 media, or M9 media containing 100 μM IPTG. Cultures were grown for 4 h post-induction prior to FACS sorting. Cells were then diluted down to a concentration of $10^7$ cells/mL in 4° PBS. Sorting was performed on a BD FACS Aria II instrument (BD Biosciences, San Jose, USA) using an 85 μm tip with a 488 nm excitation laser and a FITC emission filter (530/30 nm). This FITC channel was used for analysis of GFP expression. Cells were first gated based upon forward and side scatter, then the population of single cells were plotted on a GFP histogram. To set a gate for recovering cells exhibiting biosensor-mediated repression of reporter (GFP) output, a distribution of GFP fluorescence in cells was obtained from the population (100,000 events), and gating was set such that no more than 1% of this "ON" (uninduced) population would be recovered. This gate was used to recover biosensor candidates capable of reporter repression. To recover "reversible" repressors (minimize false positive repressors), the same gating definition described above was used, but this time (in the absence of IPTG), "ON" cells were recovered. For each round of sorting, 100,000 cells were recovered into 3 mL of M9 minimal media containing ampicillin and kanamycin, and this culture was subsequently inoculated into 50 mL of M9 containing ampicillin and kanamycin and grown overnight at 37° C. Subsequent sorts were performed (as indicated) the next day using the sorted and expanded population, as above. Traditional flow cytometry was performed on a LSRII flow cytometer (BD Biosciences, San Jose, USA). For all flow cytometry analyses, mean fluorescent intensity was calculated based on the GFP histograms of single cells (gated by forward and side scatter) using FlowJo Software (Tree Star).

Digest-Based Evaluation of Library Diversity.

All gel electrophoresis experiments were conducted with a 1% agarose gel and run in 1×TAE (tris acetate EDTA) at 120 volts. DNA was stained using SYBR Safe (Thermo Scientific) and imaged under blue light. Band sizes were estimated using a 1 kb ladder (New England BioLabs). Exposure time was adjusted to maximize the differences between the lows and highs in the gel. Plot profiles of resulting gel images were analyzed using Imager s "plot profile" function. Intensity profiles for each lane were generated by subtracting the "gray value" from an empty gel lane from the grey value evaluated along the length of the lane of interest.

Next-Generation Sequencing (NGS) and Analysis.

The naïve library of candidate biosensors was digested using KpnI and SphI, and this DNA fragment was gel extracted and subjected to probe sonication on ice (QSonica Q700 probe sonicator; 45 minutes of 30 seconds on, 15 seconds off at 10% maximum intensity) to shear the library into fragments less than 500 bp in length. Library preparation was done by PCR amplifying four equally sized regions of MBP, using primers incorporating common sequences derived from Fluidigm's AccessArray system (Moonsamy et al., 2013) to be used for NGS. The PCR primers were designed to bind either the MBP or ZFP sequence, and an MBP primer was always paired with a ZFP primer for library preparation, such that each amplicon would contain one MBP-ZFP boundary, and thus the ZFP insertion site could be determined. In total, eight unique PCR reactions were run on the naïve library: four evenly spaced MBP primers, each paired with either the forward or reverse ZFP primer. See FIG. 21 for a visual layout of the primers and Table 2 for a list of PCR reactions and primer sequences. Two biological replicates of the library were prepared for a total of sixteen reactions. Samples were submitted to the University of Illinois at Chicago (UIC) Sequencing Core, where Illumina adapters and custom barcodes were further appended to the amplicons via another PCR reaction. All samples were run together on an Illumina MiSeq lane using paired end DNA sequencing. In total, ~8M reads were generated from the sixteen samples.

TABLE 2

| PCR primer pairs for NGS. CS - Common sequence | | | |
|---|---|---|---|
| PCR Number | Forward primer (common sequence #) Primer 5'-3' | Reverse primer (common sequence #) Primer 5'-3' | ZFP direction |
| 1 | AYP828 (CS1) acactgacgacatggttctacacaacgatt catacatagctaaaaggtacc (SEQ ID NO: 79) | AYP829 (CS2) tacggtagcagagacttggtctctagggct agctctagccat (SEQ ID NO: 83) | Forward |
| 2 | AYP830 (CS1) acactgacgacatggttctacaggcaagc tgattgcttaccc (SEQ ID NO: 80) | AYP829 (CS2) tacggtagcagagacttggtctctagggct agctctagccat (SEQ ID NO: 83) | Forward |

TABLE 2-continued

PCR primer pairs for NGS. CS - Common sequence

| PCR Number | Forward primer (common sequence #) Primer 5'-3' | Reverse primer (common sequence #) Primer 5'-3' | ZFP direction |
|---|---|---|---|
| 3 | AYP831 (CS1) acactgacgacatggttctacaacaggcg agaagggatcc (SEQ ID NO: 81) | AYP833 (CS2) tacggtagcagagacttggtctgccagctct ttgttcggac (SEQ ID NO: 84) | Forward |
| 4 | AYP831 (CS1) acactgacgacatggttctacaacaggcg agaagggatcc (SEQ ID NO: 81) | AYP832 (CS2) tacggtagcagagacttggtctgggtgttca ataattgggcatgc (SEQ ID NO: 85) | Forward |
| 5 | AYP828 (CS1) acactgacgacatggttctacacaacgatt catacatagctaaaaggtacc (SEQ ID NO: 79) | AYP835 (CS2) tacggtagcagagacttggtctacaggcga gaagggatcc (SEQ ID NO: 86) | Reverse |
| 6 | AYP830 (CS1) acactgacgacatggttctacaggcaagc tgattgcttaccc (SEQ ID NO: 80) | AYP835 (CS2) tacggtagcagagacttggtctacaggcga gaagggatcc (SEQ ID NO: 86) | Reverse |
| 7 | AYP834 (CS1) acactgacgacatggttctacatctagggc tagctctagccat (SEQ ID NO: 82) | AYP833 (CS2) tacggtagcagagacttggtctgccagctct ttgttcggac (SEQ ID NO: 84) | Reverse |
| 8 | AYP834 (CS1) acactgacgacatggttctacatctagggc tagctctagccat (SEQ ID NO: 82) | AYP832 (CS2) tacggtagcagagacttggtctgggtgttca ataattgggcatgc (SEQ ID NO: 85) | Reverse |

Figure 22:
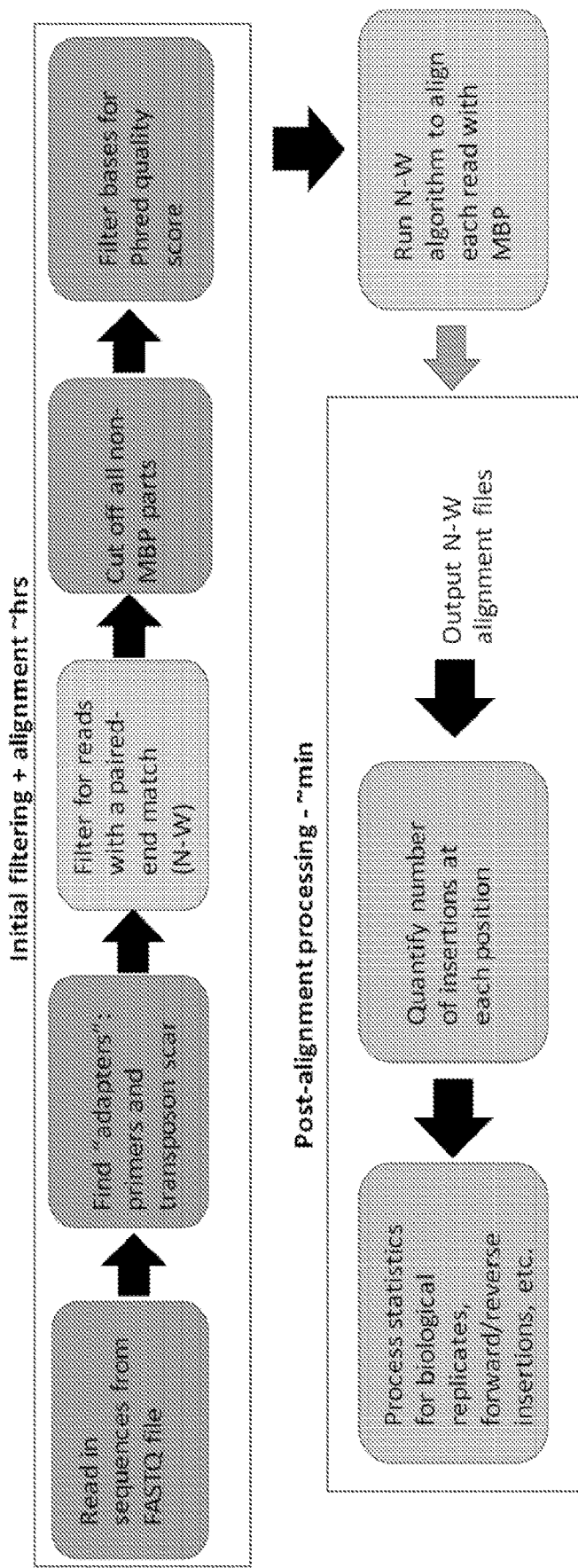
FIG. 22. Flow Chart of NGS Analysis Pipeline. This diagram summarizes the logic of the custom NGS data analysis program written for this study. Functions were created to conduct each task are outlined in the boxes. The boxes indicate steps where a Needleman-Wunsch (N-W) alignment is performed or indicate post-processing steps that only require the Needleman-Wunsch output alignment file of the insert aligned against the template. Phred quality scores are a measure of the quality of identification of a particular nucleotide during the NGS process; a score of 20 corresponds to 99% confidence in the identity of that base.

All data analysis was performed using customized software (written in Python). Briefly, reads were first filtered to retain only those reads containing the transposon scar sequence as well as the sequences of the primers used to generate the amplicon corresponding to that sample. Next, we identified viable paired end reads as those in which at least 12 contiguous bases at the end of one read perfectly matched the reverse complement of its paired read. Only such viable paired end reads were carried forward. Next, to discard low-quality reads, we filtered out reads with Phred quality scores below 20 (a score of 20 corresponds to 99% confidence in the identity of that base). Next, reads were partitioned into bins by read length, in roughly 50 bp increments, to enable subsequent normalization of scores by read length. Reads were then aligned to the MBP template sequence using the Needleman-Wunsch algorithm (using a gap opening penalty of 10.0, gap extension penalty of 0.5, and the EDNAFULL scoring matrix). The resulting alignment scores were normalized by read length (i.e., by bin), since scores generally increase with length of alignment. Alignments that generally had less than 2 gaps per 50 bases aligned were carried forward. The resulting alignments were then analyzed to identify ZFP insertion sites, which we defined as the first or last base to align to MBP, depending on the orientation of the amplicon being analyzed. Insertion sites were only classified as "identified" if the alignment comprised a block of perfect alignment with MBP between the identified insertion site and the end of the read (i.e., reads were discarded if the alignment generated gaps or mismatches within the block of sequence where the read aligned to the MBP template). A graphical representation of this pipeline is presented in FIG. 22. In all cases, the insertion site refers to the last base of MBP upstream (5') of the transposon insertion. All of the NGS analysis code and data is available at https://github.com/PeterSu92/BERDI-NGS-insertion-analysis.

Results

Generation of Random Domain Insertion Libraries Via Transposon Mutagenesis.

Figure 15:
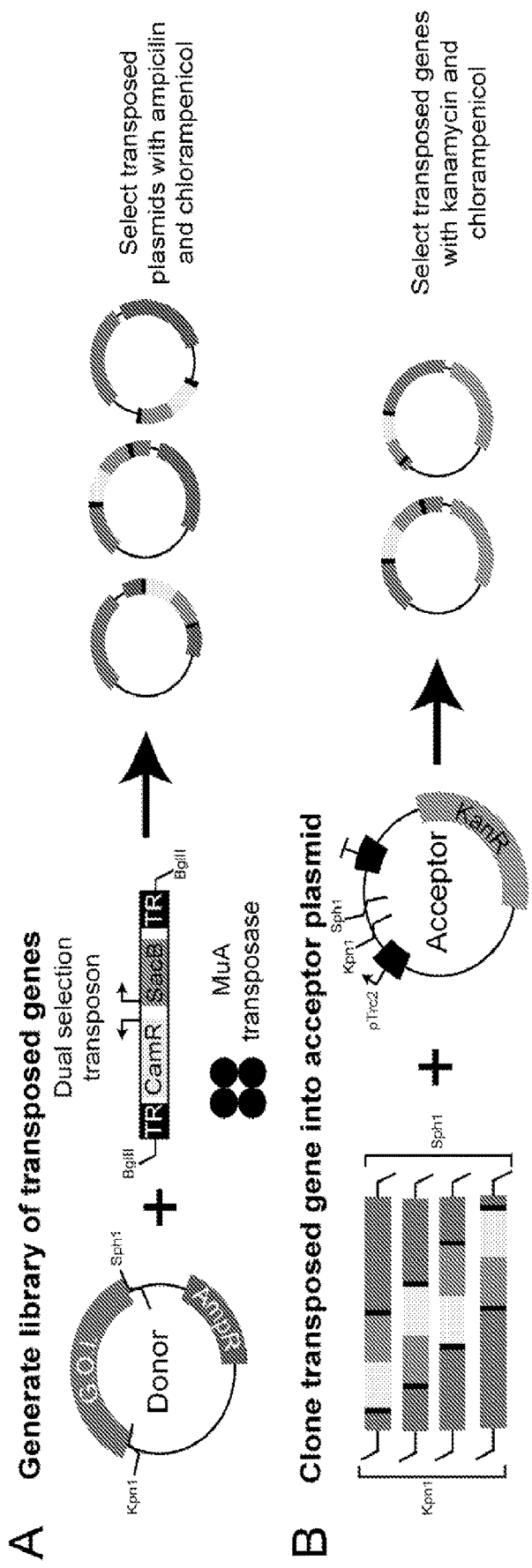
FIG. 15. Overview of the BERDI method for generating novel metabolite-responsive transcription factor biosensors. (A) Library generation—The donor plasmid containing the gene of interest, the transposon, and the transposase enzymes create a library of random insertions. (B) Cloning of the transposed gene. Gene containing the inserted transposon is isolated, and cloned into a similarly digested expression plasmid. (C) Exchanging the transposon for the ZFP. The transposon is replaced with ZFP and are transformed into cells containing the reporter GFP plasmid. (D) Cartoon of potential enrichment strategy for metabolite responsive biosensors using FACS. See materials and methods for experimental details.
Figure 15:
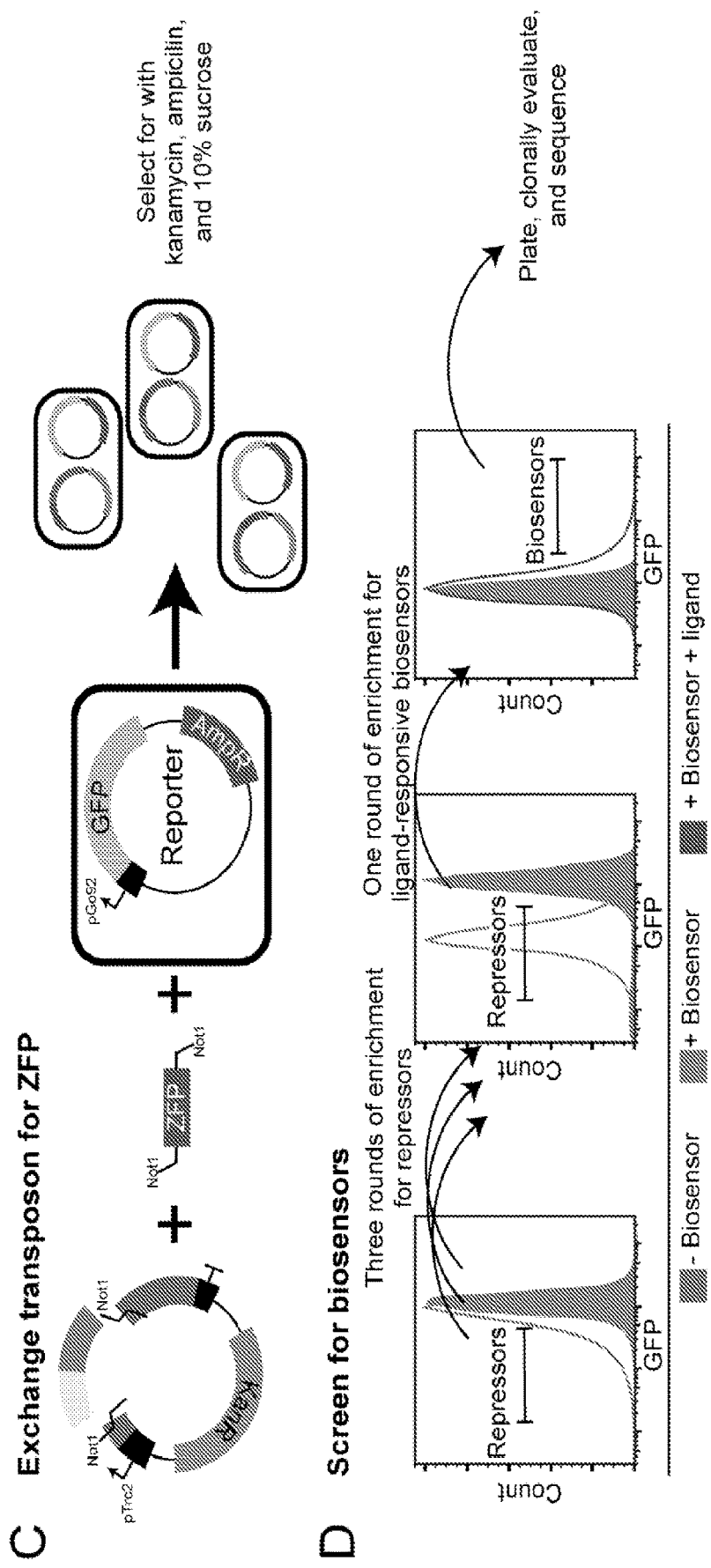

Here we sought to develop an efficient method for generating novel transcription factor biosensors, which we term Biosensor Engineering by Random Domain Insertion (BERDI). The overall BERDI strategy is summarized in FIG. 15. This method utilizes the MuA transposase to insert a transposon nonspecifically into a plasmid encoding the gene sequence for the metabolite binding protein. Transposon mutagenesis provides a simple and efficient method for generating a library of insertions due to its nonspecific and single insertion into each target DNA molecule, minimal scar sequence, and ability to generate >$10^5$ variants in a single pot in vitro reaction (Haapa et al., 1999, Mehta et al., 2012, Nadler et al. 2016). The transposon is later exchanged for a ZFP coding sequence to generate a library of candidate biosensors. Transposase insertion has been used to successfully circularly permute proteins as well as to profile proteins for permissible insertion points (Edwards et al., 2008, Mehta et al., 2012, Nadler et al., 2016, Oakes et al., 2016, Segall-Shapiro et al., 2011). Here, we investigated whether this technique can be used to generate novel biosensors by randomly inserting a ZFP into a ligand-binding protein. We reasoned that choosing MBP as a model ligand-binding domain would be the most effective strategy for evaluating the BERDI method, since (a) we know that at least one such feasible biosensor should exist, based upon our prior work (Younger et al., 2016), and (b) such an approach enabled us to utilize established reporter constructs and biosensor evaluation methods.

First, a library of candidate biosensors was generated. MuA inserts randomly into target DNA molecules (in either forward or reverse direction), such that for a plasmid of length n bases, the total number of possible insertions is 2n. Additionally, multiplying the three frames in which the transposon can insert by the two directions in which the transposon can insert (i.e., forward or reverse) yields six possible insertions for a given codon of target DNA. However, only one of these six insertions (forward and in-frame) will generate a productive insertion. The transposase also leaves a partially controllable scar (i.e., one has some choice in the design of this scar sequence). Therefore, we designed the transposon such that when the ZFP is inserted in frame with the rest of MBP, the resulting scars encode for linkers comprising three alanine residues on either side of the ZFP domain (see FIG. 20B for details).

Given that transposon insertions are random and independent of one another, we aimed to achieve a library size at least 10× greater than the maximum possible number of insertions—6,288 (the number of directions in which the transposon can insert, 2, multiplied by the size of the target plasmid, 3144 bp); this yields a target library size of 62,880 members. Our initial transposition library generated over $8 \times 10^5$ colonies, or ~125× the maximum library diversity. Next, the library was subcloned to eliminate MBP variants lacking a transposon (i.e. when the transposon inserted elsewhere in the plasmid backbone), and then the transposon was replaced with a sequence encoding the ZFP to yield a naïve candidate biosensor library. At each step, we confirmed that library diversity exceeded the target of 10× oversampling (Table 3).

TABLE 3

Targeted and experimental library sizes

| Experimental Step | Theoretical library size | Targeted library size (10x oversampling) | Experimental Results | Experimental Oversampling |
|---|---|---|---|---|
| Generate library | 3144 (bp MBP plasmid) × 2 (forward or reverse) = 6,288 | 62,880 | ~800,000 | ~125x |
| Clone transposed gene into expression plasmid | 1116 (bp of MBP) × 2 (forward or reverse) = 2,232 | 22,320 | ~30,000 | ~14x |
| Exchange transposon for ZFP | 1116 (bp of MBP) × 2 (forward or reverse) = 2,232 | 22,320 | ~30,000 | ~14x |

Analyzing Diversity of the Naïve Library.

Figure 16:
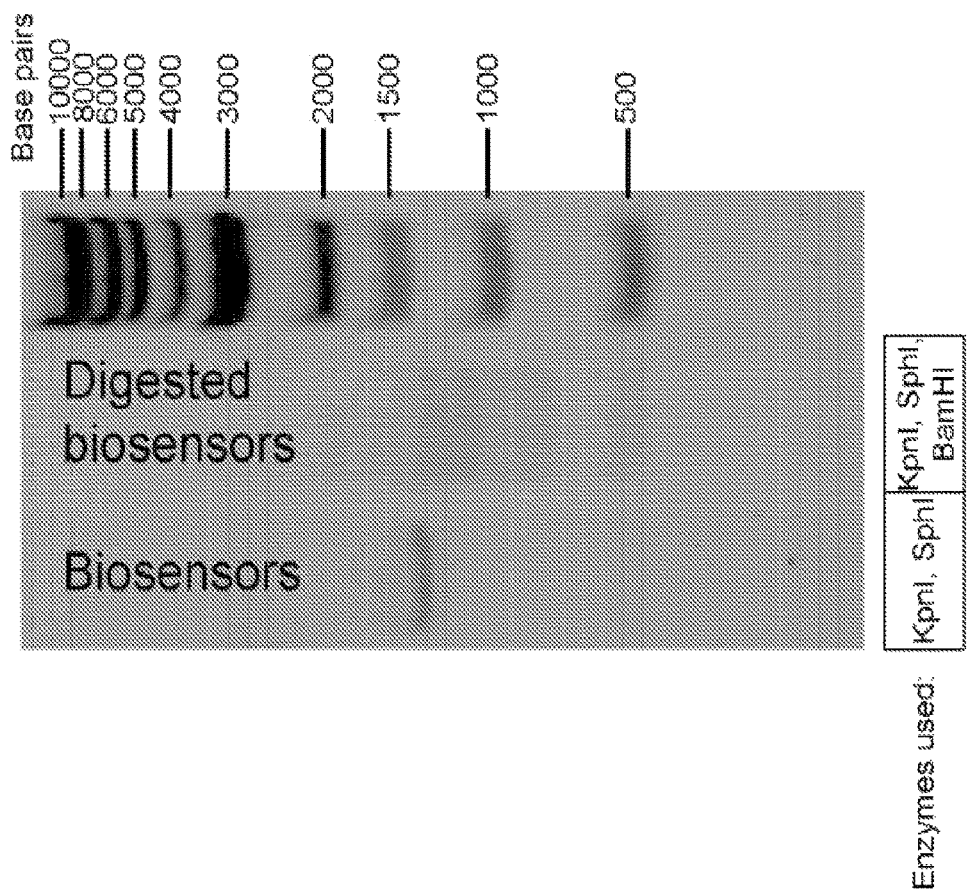
FIG. 16. Analysis of naïve library diversity. (A) Initial evaluation of distribution of biosensor diversity via gel electrophoresis comparing the naïve library of biosensors, to the same sample now treated with a restriction enzyme unique to the ZFP (BamHI). Lane 1, full length biosensors (1455 bp). Lane 2, digested biosensors. Lane 3, DNA ladder with the corresponding bp values listed. (B) Intensity trace of both lanes from panel A created in ImageJ. Position zero maps to the space in the gel below any visible DNA, taken to be the background intensity. (C) Experimentally observed ZFP insertion positions into MBP. Insertions found via NGS and/or via colony (Sanger) sequencing are displayed.
Figure 16:
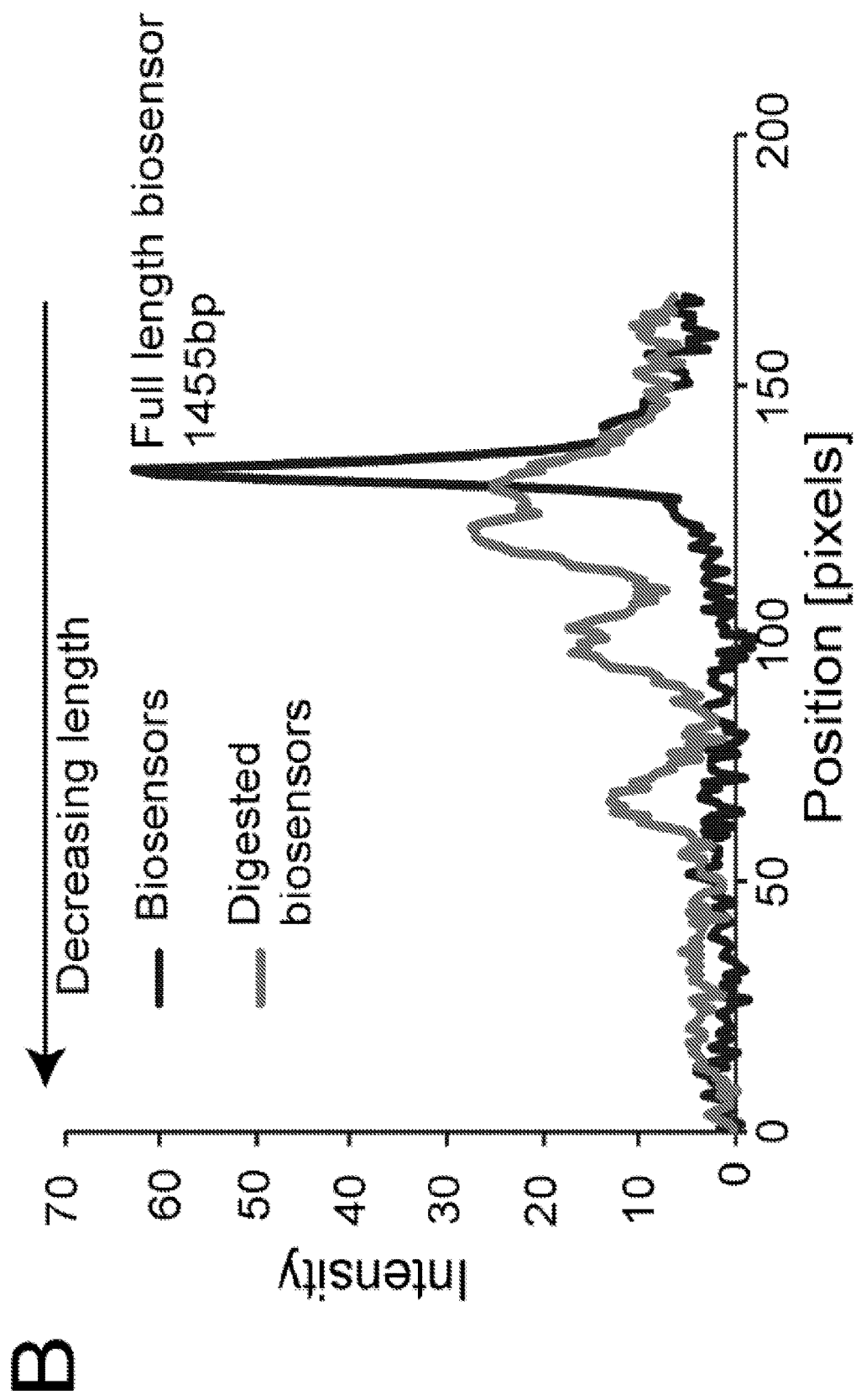
Figure 16:
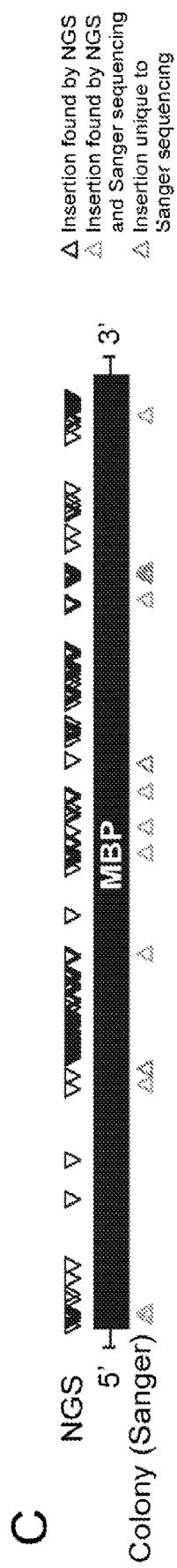
Figure 21:
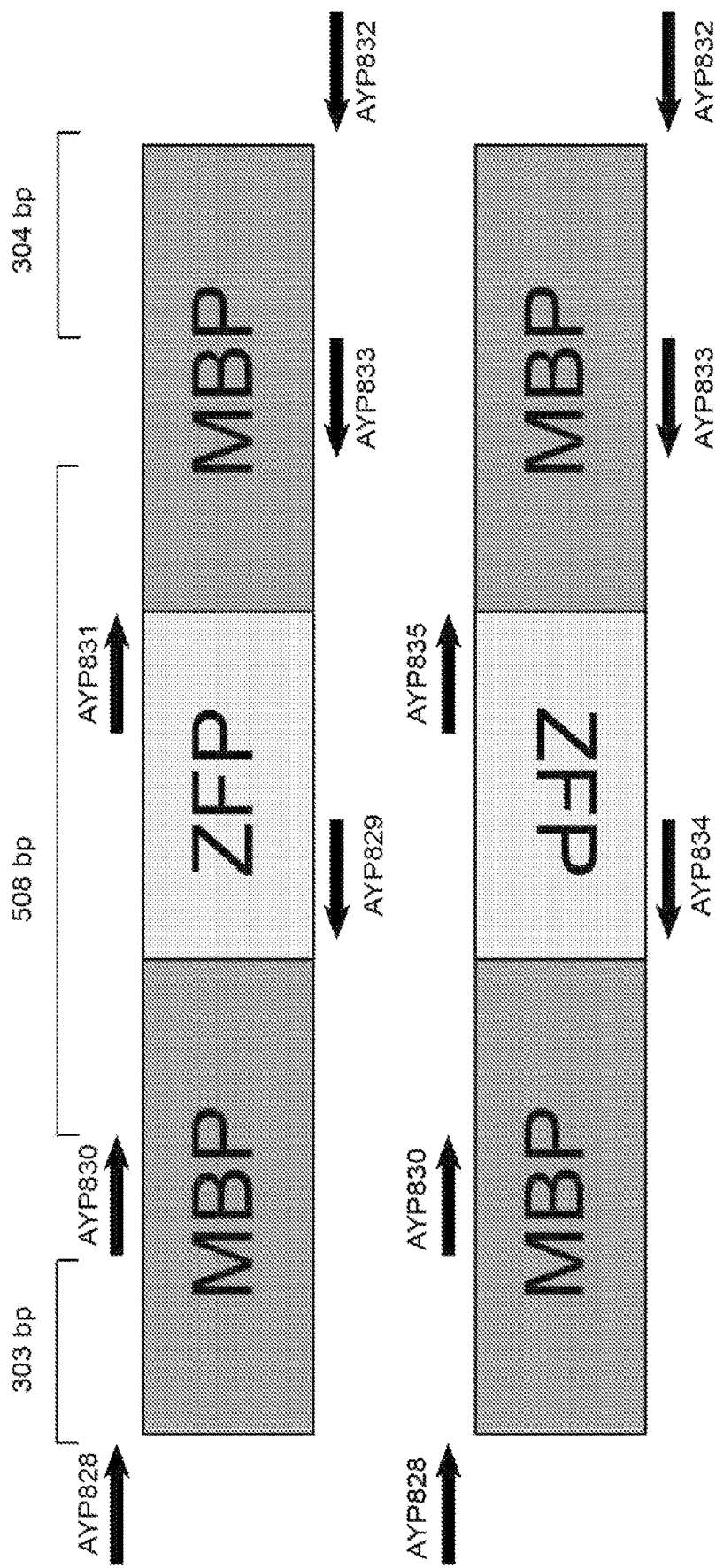
FIG. 21. Representative graphic of the primers used to prepare library for deep sequencing. The zinc finger could potentially be anywhere inside MBP and is only drawn in the middle here for ease of visualization. All primers contained a variant of the common sequences necessary for the downstream amplification conducted by the next generation sequencing core. Primers were spaced apart in order to capture insertions in windows of 300 bp, as the NGS required amplicons <500 bp in length. The top cartoon describes the primers used for the forward facing ZFP, whereas the bottom cartoon described the reactions that were done to account for possible reverse ZFP insertions due to the palindromic nature of the transposon recognition sequence. Please see Table 2 for description of the 8 PCRs.

In order to evaluate library diversity prior to sorting for functional biosensors, we analyzed the naïve library using three distinct methods. First, sequences from the naïve library were digested out of the expression vector library, and these biosensor-encoding fragments were then subsequently digested with a restriction enzyme recognizing a unique site in the sequence encoding the ZFP. These digests were evaluated by gel electrophoresis (FIG. 16A,B), which yielded a smear consistent with the presence of many diverse insertions. We next performed both Sanger sequencing on 46 individual colonies and next-generation sequencing (NGS) on the library, by PCR amplifying regions containing both the MBP and ZFP and then subjecting these amplicons to NGS (FIG. 21). Confirmed insertions were identified by sequence analysis (FIG. 16C). Colony sequencing was performed to complement NGS, since the latter is expected to be impacted by biases introduced during PCR-based library preparation. A full list of insertion counts identified by sequencing individual colonies and NGS can be found in Table 4.

TABLE 4

List of all insertions found by NGS and Sanger (colony) sequencing

| Insertion Position | Count by NGS | Count by Sanger | Insertion Position | Count by NGS | Count by Sanger | Insertion Position | Count by NGS | Count by Sanger |
|---|---|---|---|---|---|---|---|---|
| 1 | 7 | 0 | 384 | 2 | 0 | 771 | 1 | 0 |
| 2 | 35358 | 0 | 391 | 2 | 0 | 779 | 1 | 0 |
| 9 | 2 | 1 | 394 | 3 | 0 | 785 | 5 | 0 |
| 10 | 1 | 0 | 404 | 1 | 0 | 786 | 662975 | 0 |
| 12 | 1 | 0 | 405 | 1 | 0 | 787 | 666 | 0 |
| 13 | 1 | 0 | 410 | 2 | 0 | 788 | 1 | 0 |
| 14 | 13 | 0 | 412 | 2 | 0 | 789 | 1 | 0 |
| 15 | 868175 | 1 | 417 | 1 | 0 | 791 | 4 | 0 |
| 16 | 4 | 0 | 422 | 1 | 0 | 794 | 1 | 0 |
| 18 | 1 | 0 | 423 | 1 | 0 | 807 | 66 | 0 |
| 32 | 2 | 0 | 442 | 1 | 0 | 808 | 2 | 0 |
| 40 | 1 | 0 | 443 | 66 | 1 | 809 | 262424 | 0 |
| 59 | 4 | 0 | 444 | 318427 | 0 | 810 | 192 | 0 |
| 60 | 24625 | 0 | 445 | 1 | 0 | 812 | 6 | 0 |
| 74 | 2 | 0 | 448 | 1 | 0 | 814 | 2 | 0 |
| 152 | 15 | 0 | 494 | 1 | 0 | 867 | 2 | 4 |
| 201 | 42 | 0 | 550 | 1 | 0 | 870 | 21 | 0 |
| 285 | 1 | 0 | 561 | 1 | 0 | 896 | 0 | 1 |
| 286 | 2708 | 4 | 563 | 1 | 0 | 897 | 0 | 1 |
| 287 | 2 | 0 | 564 | 7093 | 4 | 898 | 0 | 1 |
| 300 | 3366 | 0 | 565 | 130462 | 0 | 899 | 2840 | 0 |
| 306 | 0 | 1 | 566 | 4 | 0 | 900 | 7824 | 2 |
| 325 | 12 | 0 | 570 | 1 | 0 | 901 | 41428 | 15 |
| 326 | 4 | 0 | 580 | 2299 | 0 | 902 | 1 | 0 |
| 329 | 1 | 0 | 581 | 8766 | 0 | 903 | 44428 | 5 |
| 330 | 10 | 0 | 594 | 27159 | 2 | 904 | 3 | 0 |
| 331 | 4 | 0 | 595 | 68187 | 0 | 907 | 1 | 0 |
| 332 | 3 | 0 | 614 | 2642 | 0 | 938 | 2 | 0 |

TABLE 4-continued

List of all insertions found by NGS and Sanger (colony) sequencing

| Insertion Position | Count by NGS | Count by Sanger | Insertion Position | Count by NGS | Count by Sanger | Insertion Position | Count by NGS | Count by Sanger |
|---|---|---|---|---|---|---|---|---|
| 333 | 3 | 0 | 615 | 2269 | 0 | 953 | 1 | 0 |
| 334 | 1 | 0 | 616 | 1 | 0 | 976 | 4 | 0 |
| 336 | 3 | 0 | 623 | 8349 | 0 | 978 | 32589 | 0 |
| 337 | 2 | 0 | 637 | 39957 | 1 | 979 | 14 | 0 |
| 340 | 8 | 0 | 638 | 5345 | 0 | 987 | 3932 | 0 |
| 341 | 1 | 0 | 639 | 1 | 0 | 993 | 1 | 0 |
| 346 | 1 | 0 | 680 | 8378 | 0 | 1004 | 3219 | 0 |
| 348 | 1 | 0 | 681 | 118 | 0 | 1068 | 595 | 0 |
| 349 | 5 | 0 | 670 | 0 | 1 | 1080 | 1 | 0 |
| 350 | 7 | 0 | 706 | 1 | 0 | 1086 | 72 | 0 |
| 351 | 2 | 0 | 711 | 201312 | 0 | 1087 | 183665 | 1 |
| 354 | 4 | 0 | 712 | 1659 | 0 | 1088 | 3 | 0 |
| 360 | 1 | 0 | 713 | 8 | 0 | 1090 | 2 | 0 |
| 361 | 2 | 0 | 715 | 1 | 0 | 1099 | 1 | 0 |
| 363 | 3 | 0 | 716 | 1 | 0 | 1102 | 1 | 0 |
| 364 | 1 | 0 | 717 | 1 | 0 | 1103 | 1 | 0 |
| 365 | 2 | 0 | 719 | 1 | 0 | 1104 | 1 | 0 |
| 366 | 14 | 0 | 723 | 1 | 0 | 1105 | 1 | 0 |
| 367 | 3 | 0 | 748 | 1 | 0 | 1110 | 1 | 0 |
| 371 | 1 | 0 | 757 | 1 | 0 | 1111 | 4 | 0 |
| 373 | 16 | 0 | 758 | 181930 | 0 | 1112 | 236842 | 0 |
| 382 | 8 | 0 | 759 | 884 | 0 | 1113 | 113 | 0 |
| 383 | 3 | 0 | 762 | 5 | 0 | 1115 | 1 | 0 |

When using conservative NGS analysis parameters (e.g., utilizing only alignments wherein the read perfectly matched the template, without gaps) to identify insertions, we observed at least 148 insertions across MBP, representing 13.2% of all possible insertions. Out of these, 47 (31%) were in frame, and the percentage of insertions containing a forward-facing ZFP was 48%, which is consistent with the expectation that MuA-mediated insertion is random (Table 5). We identified 37 productive insertions (forward-facing and in-frame) from these analyses.

TABLE 5

Frequency of insertion types observed in the naïve candidate biosensor library

| Type of insertion | Expected if unbiased | Observed by NGS (n = 148 insertions) | Observed by colony (Sanger) sequencing (n = 17 insertions) |
|---|---|---|---|
| In frame | 33% | 30% | 12% |
| Out of frame | 66% | 70% | 88% |
| Forward ZFP | 50% | 49% | 48% |
| Reverse ZFP | 50% | 51% | 52% |

To evaluate the bias that occurred during the PCR amplification performed in preparation for NGS, we analyzed several parameters. In our NGS data analysis, we observed insertion counts ranging from very abundant ($10^6$ counts) to very rare (1 count), and the top five most abundant insertions encompassed 64.8% of all insertion counts. 12 insertions out of the 46 found by Sanger sequencing individual colonies (counting both productive and non-productive insertions) were also identified in the NGS analysis, yet only one insertion site identified by colony sequencing matched any of the top five most frequent insertions identified by NGS analysis. Also, five of the insertion sites identified by sequencing colonies represented insertions not found by NGS. We therefore concluded that amplification bias significantly affected our NGS results, which suggests that our naïve library diversity was broader than the limited set of insertions confirmed by our conservative NGS analysis. Moreover, since the transposon insertion ratios (forward/reverse, in-frame vs. out of frame) demonstrated that the transposase functioned as expected (Table 5), and since our library size exceeded 10× oversampling, we concluded that the library likely contained sufficient diversity and we proceeded to investigate whether the library contained any functional bio sensors.

Identification of Functional Biosensors.

Figure 17:
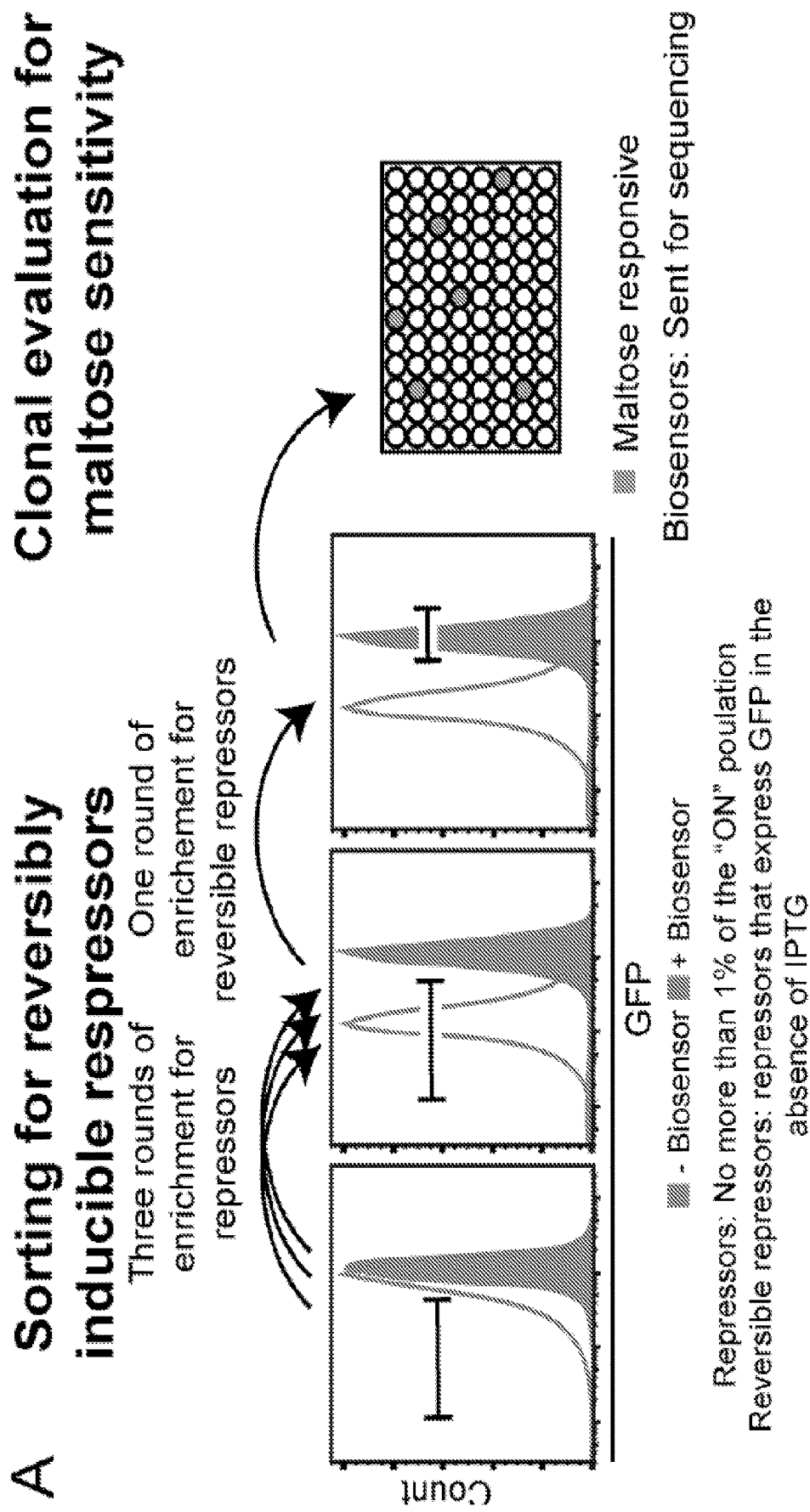
FIG. 17. Isolation of functional biosensors by screening. (A) Cartoon depicting the overall biosensor enrichment strategy applied. Briefly, three rounds of FACS were performed, each time sorting the induced population using a gate encompassing no more than 1% of the "ON" (uninduced) population. One subsequent round of sorting was done to isolate only repressors that were reversible. Cells were then plated, and clonally evaluated for maltose responsiveness. Successful biosensors were sequenced to determine the insertions position. (B) Crystal structure of MBP is shown (PDB #1ANF)(Quiocho et al., 1997), with the insertional positions (in amino acid number) of each biosensor labeled. A cluster of spheres represents the ligand, maltose (space-filling model). (C) Flow cytometry of the reference biosensor compared to the three new biosensors. Biosensor production was induced with 30 µM IPTG and maltose was added at 100 mM. The insertional position (in amino acid number), and whether the ZFP is a single, or double insertion, is listed in the top left corner of each plot. Plots represent a minimum of 10,000 cells in each condition and are representative of multiple independent experiments.
Figure 17:
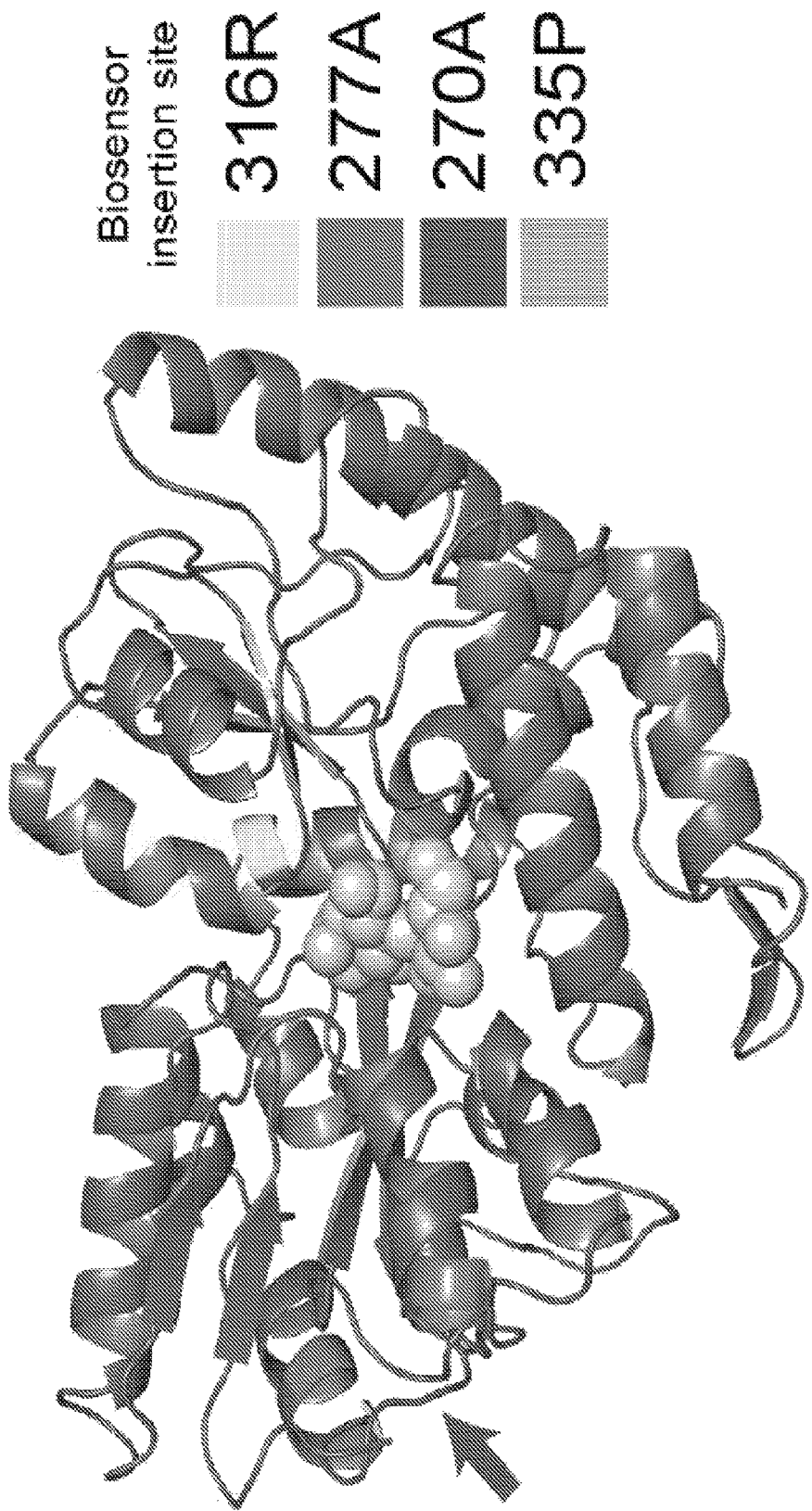
Figure 17:
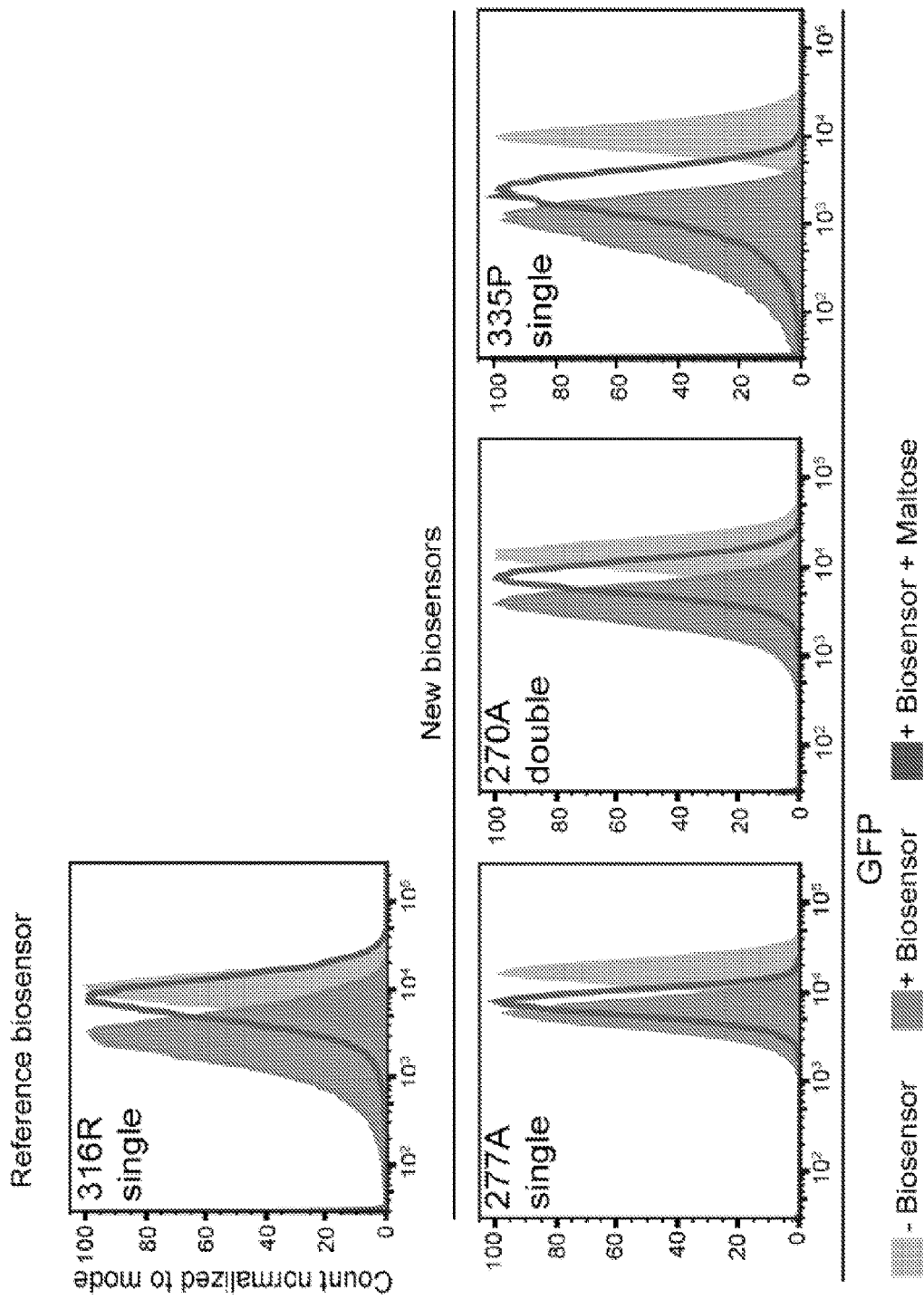

Our overall strategy was to first enrich for candidate biosensors capable of repressing the reporter in the absence of maltose, then to reselect to eliminate false positives, and then to identify maltose-responsive biosensors from within that pool (FIG. 17A). The naïve library was first screened by FACS to enrich for candidate biosensor clones which, when expressed at a high level (100 µM IPTG induction), repressed the GFP reporter output. The selected pool was recovered and regrown, and this process was iterated on three consecutive days to enrich for candidate biosensors that were at least capable of repressing reporter output. Next, this population of candidate biosensors was re-screened by FACS in the absence of IPTG, to recover "reversible" repressors (clones which express GFP in the absence of IPTG) in order to minimize false positives. Following these four rounds of screening, the recovered cells were plated and clonally assayed for maltose-responsiveness. Candidate biosensors were initially evaluated under conditions of 30 µM IPTG to induce the expression of the biosensor and 100 mM maltose, which are conditions under which we previously observed maximal maltose-responsiveness of the reference biosensor (Younger et al., 2016). At this point, library members exhibiting both (a) at least a 2-fold repression of reporter output in the absence of maltose and (b) any significant maltose responsive were defined as "functional biosensors" and were sequenced. Of the 672 colonies analyzed, 340 demonstrated the ability to repress the reporter, but only 159 of those met both criteria for potential biosensors. These 159 colonies represented three unique biosensors (270A, 277A, and 335P). The other 181 repressors represented out-of-frame insertions at six positions (5E, 31G, 188G, 194T, 213I, and 262V). Moreover, none of the three novel biosensors identified were detected in the original naïve library, via either colony (Sanger) sequencing or NGS. Together, these observations indicate that our strategy substantially enriched for functional biosensor constructs, even if they were rather rare in the original naïve library.

Figure 23:
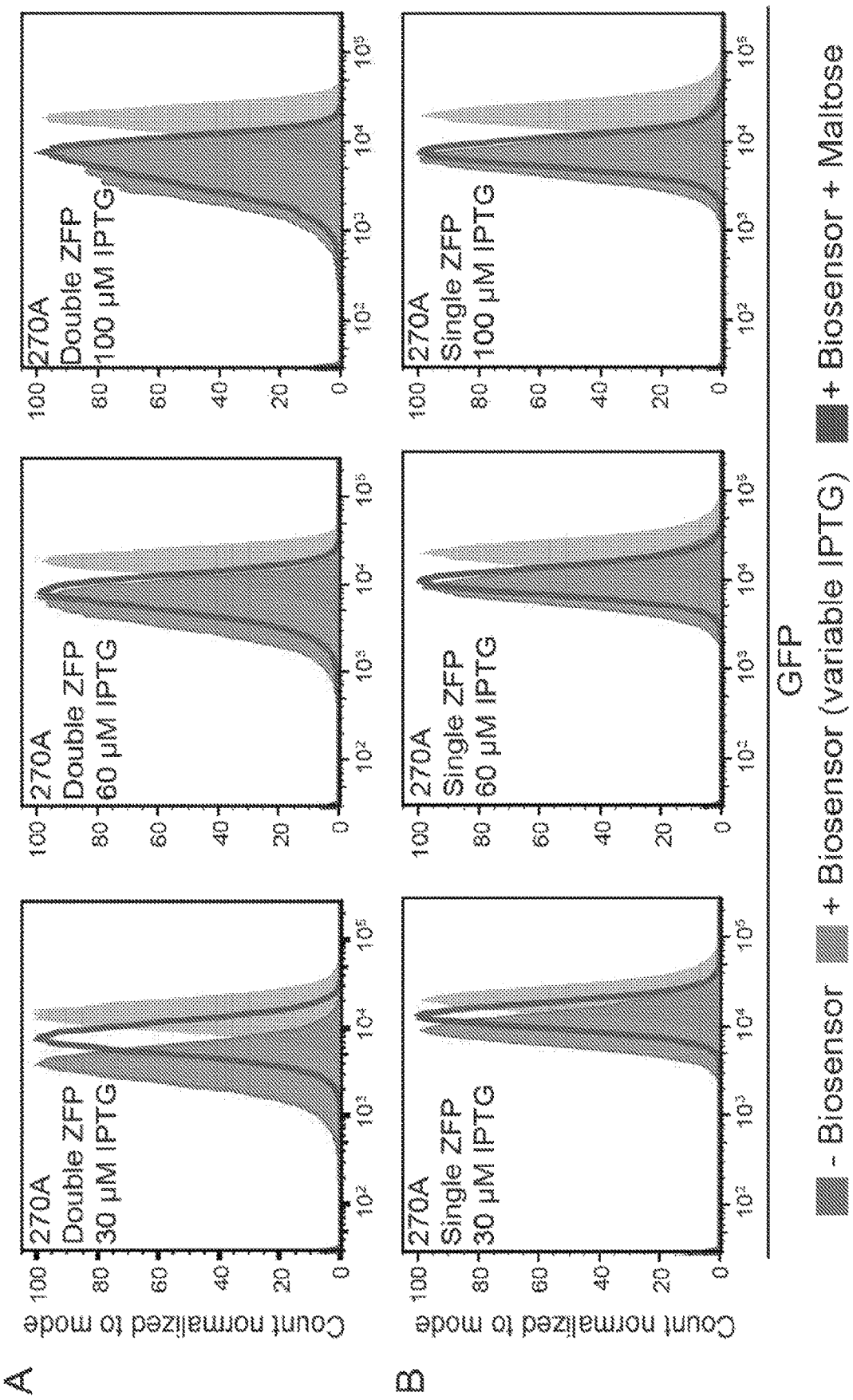
FIG. 23. 270A double ZFP versus 270A single ZFP. The effects the number of zinc finger inserts into MBP at position 270A on biosensor performance were evaluated using flow cytometry for this construct. IPTG was used to induce biosensor repression, and the maltose addition relieved repression. The plots shown use varying concentrations of IPTG and are grouped by the number of zinc fingers present with (A) two zinc finger insertions, (B) one zinc finger insertion.

The three functional biosensors, representing a ZFP insertion at 277A, an insertion of two ZFPs at 270A, and a single ZFP insertion at 335P, were next examined in greater detail. These insertions are depicted graphically in FIG. 17B, along with the position at which the ZFP was previously inserted by design in the reference biosensor, at position 316R (Younger et al., 2016). Interestingly, these four insertion points are distributed in three distinct regions of MBP. All four are on the outside of the protein and are either in a loop (270A) or at the end of an α-helix, near a loop (316R, 277A, and 335P). Given the sample size, and the lack of crystal structures of the new biosensors, it is not yet possible to predict whether they share other features that lend themselves to maltose-responsive transcriptional regulation. Performance of the new biosensors was next compared to that achieved by the reference biosensor (FIG. 17C). Both the 277A and 270A biosensors exhibited similar repression to that conferred by the reference biosensor (~3 to 4-fold), however, neither 277A nor 270A exhibited as much maltose-responsiveness as did the reference biosensor. Notably, the 335P biosensor exhibited much better repression (~10-fold) compared to the other three constructs, while also exhibiting substantial responsiveness to maltose. We next investigated why our BERDI method recovered a 270A double ZFP insertion but not a 270A single ZFP insertion. Such a double ZFP insertion is indeed a potential product that could be generated when cloning the ZFP cassette in place of the transposon cassette (both ends of the ZFP cassette use the same NotI restriction site), but given the ligation ratios used, we expected such a double insertion to be substantially less frequent than a single insertion. Therefore, we next generated the 270A single ZFP insertion biosensor to evaluate its performance. First, the 270A single ZFP construct exhibited milder repression compared to the 270A double ZFP variant (FIG. 23), which would explain why the single insertion variant was not (or was less) enriched during the initial three rounds of FACS screening. Furthermore, the single ZFP insertion at 270A exhibited less responsiveness to maltose than did the double insertion biosensor variant. Taken together, these clonal observations support the conclusion that the BERDI method generated and selected for functional biosensors, based upon their performance, as intended.

Biosensor Performance Characteristics: Dose and Linker Analysis.

Figure 18:
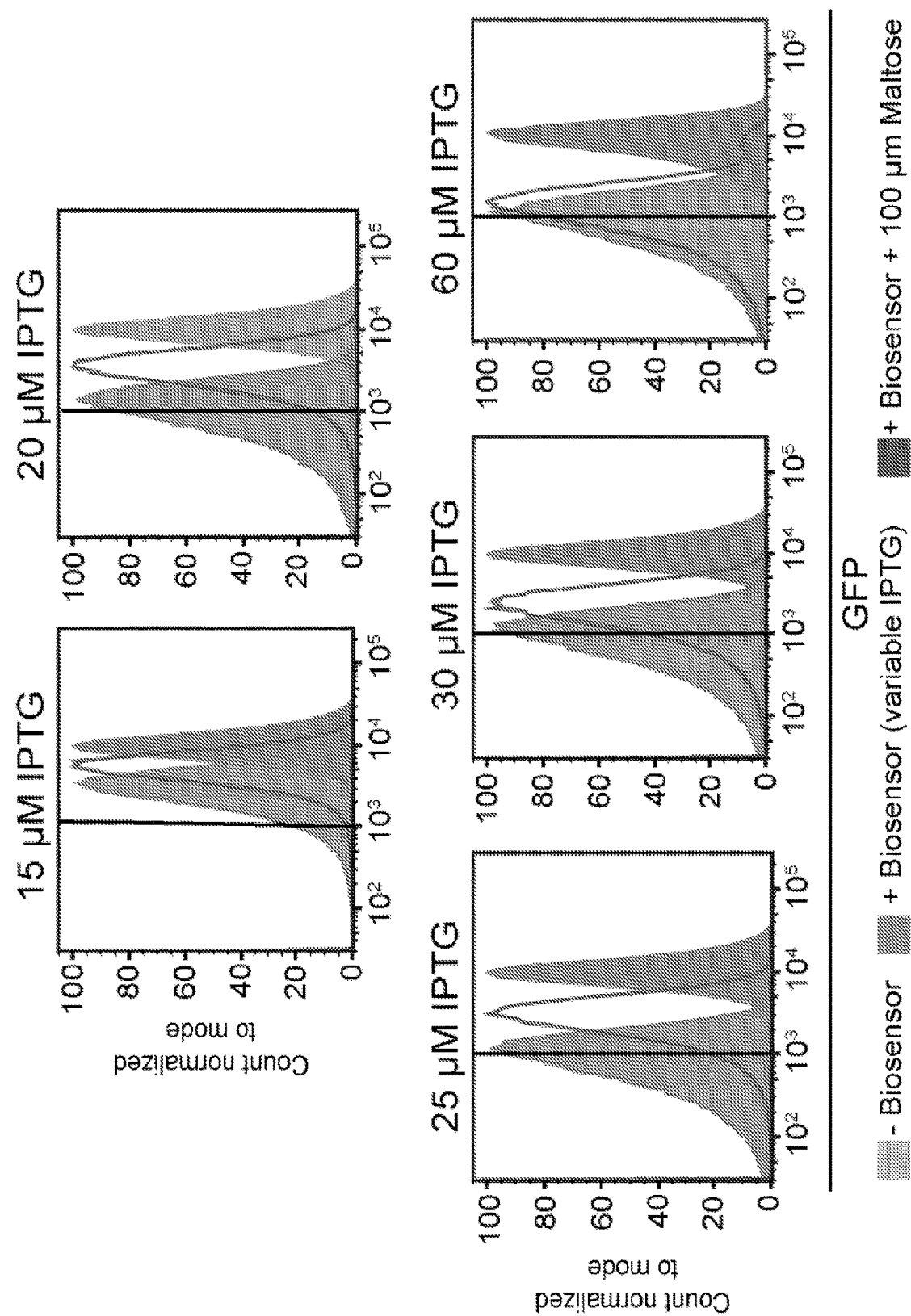
FIG. 18. Impact of biosensor expression level on performance. Response of reporter output to the addition of IPTG and IPTG along with maltose measured by flow cytometry. The maltose concentration used here was 100 mM. The vertical line at $10^3$ GFP fluorescence units is a visual aid to facilitate comparison across the conditions. Plots represent multiple independent experiments.

Having identified several novel functional biosensors, we next evaluated their performance characteristics. First, to investigate the impact of biosensor dose on reporter output repression and maltose sensitivity, the strongest repressor, 335P, was induced at a range of IPTG concentrations (FIG. 18). At the highest IPTG concentration evaluated here (60 µM), the repression was not significantly greater than that observed at 25 or 30 µM IPTG, indicating that at these lower concentrations, saturating levels of the biosensor already achieve maximal repression. However, at 60 µM IPTG, the system was not sensitive to maltose, indicating that the biosensor was in excess relative to intracellular maltose levels (which would be lower than extracellular maltose levels). As the level of IPTG (and thus biosensor expression) decreased, the sensitivity of the 335P biosensor to maltose increased, but once the IPTG level dropped below 20 µM IPTG, the overall repression of the reporter decreases, as expected given the decrease in biosensor protein. Thus, there exists an optimal window of biosensor expression that confers maximal maltose sensitivity while maintaining sufficient promoter repression (in the absence of maltose), corresponding to around 25 µM IPTG (different from the 100 µM IPTG used during selection). Each of these phenomena is consistent with observations previously characterized with the reference biosensor (Younger et al., 2016), suggesting that at least at this functional level, the reference biosensor and this novel BERDI-generated biosensor exhibit qualitatively similar performance characteristics.

Figure 19:
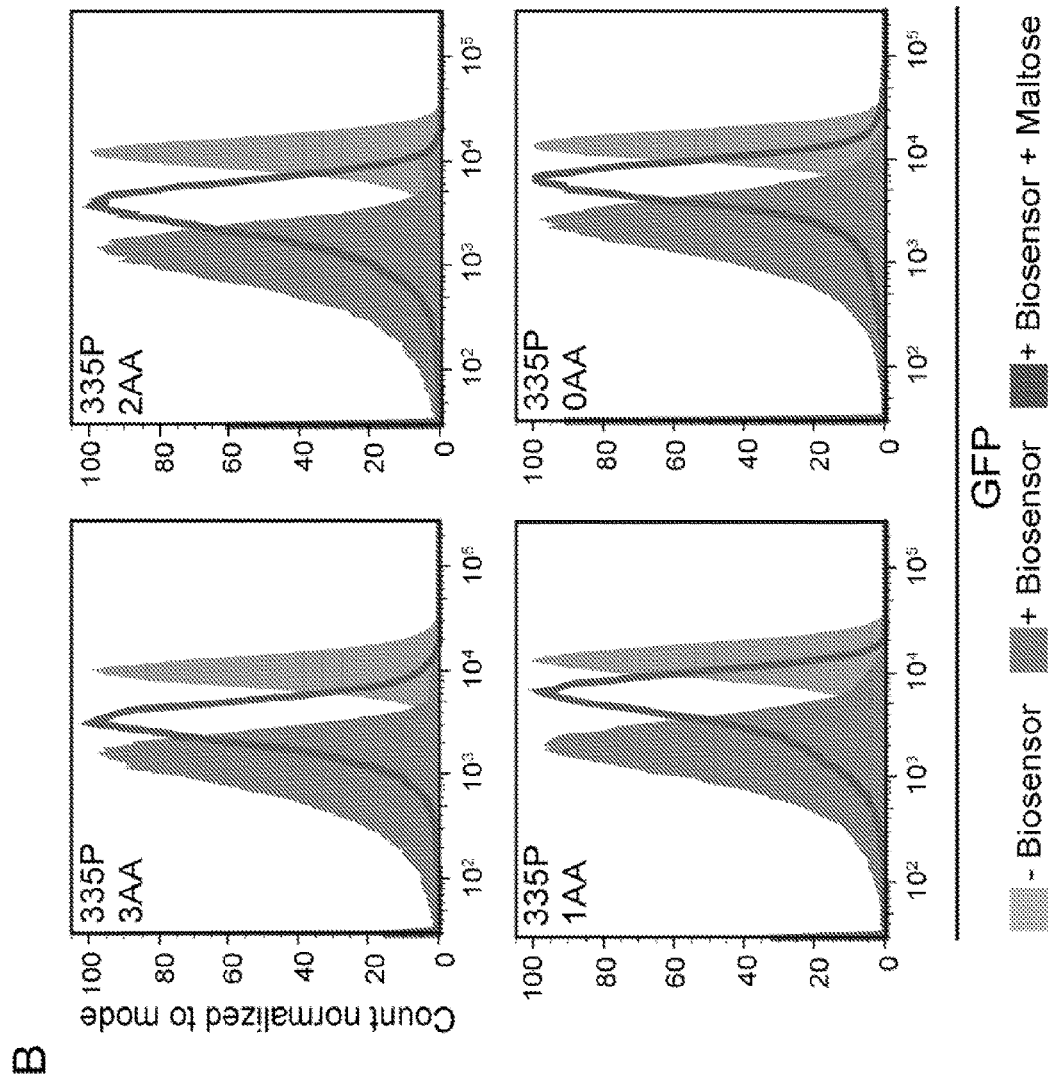
FIG. 19. Impact of linker tuning on biosensor performance. (A) Comparison of the effect of amino acid linkers between reference biosensor and its transposon-created counterpart on repressibility and alleviation with maltose. (B) Impact of varying linker lengths for the 335P biosensor. Biosensors were induced with 30 µM IPTG and maltose was added at 100 mM final concentration. (C) Mean fluorescence intensity of the four linker variants of the 335P biosensor measured via flow cytometry. Biosensors were induced with 30 µM IPTG and maltose was added at 100 mM final concentration. Samples were run in biological triplicate, and error bars represent one standard deviation. (*p≤0.001 from a two-tailed students t-test). All data are representative of multiple independent experiments.
Figure 19:
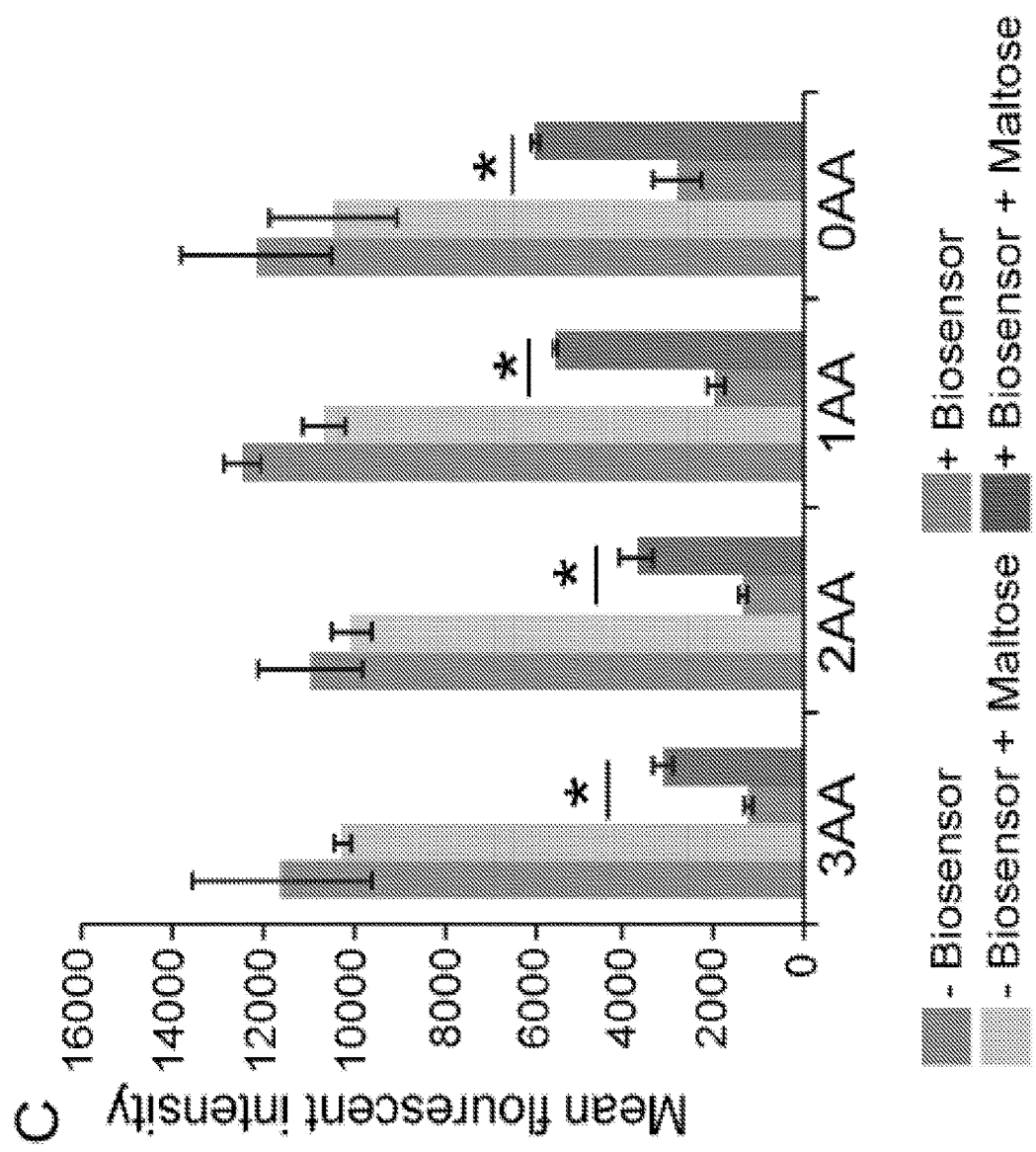
Figure 20:
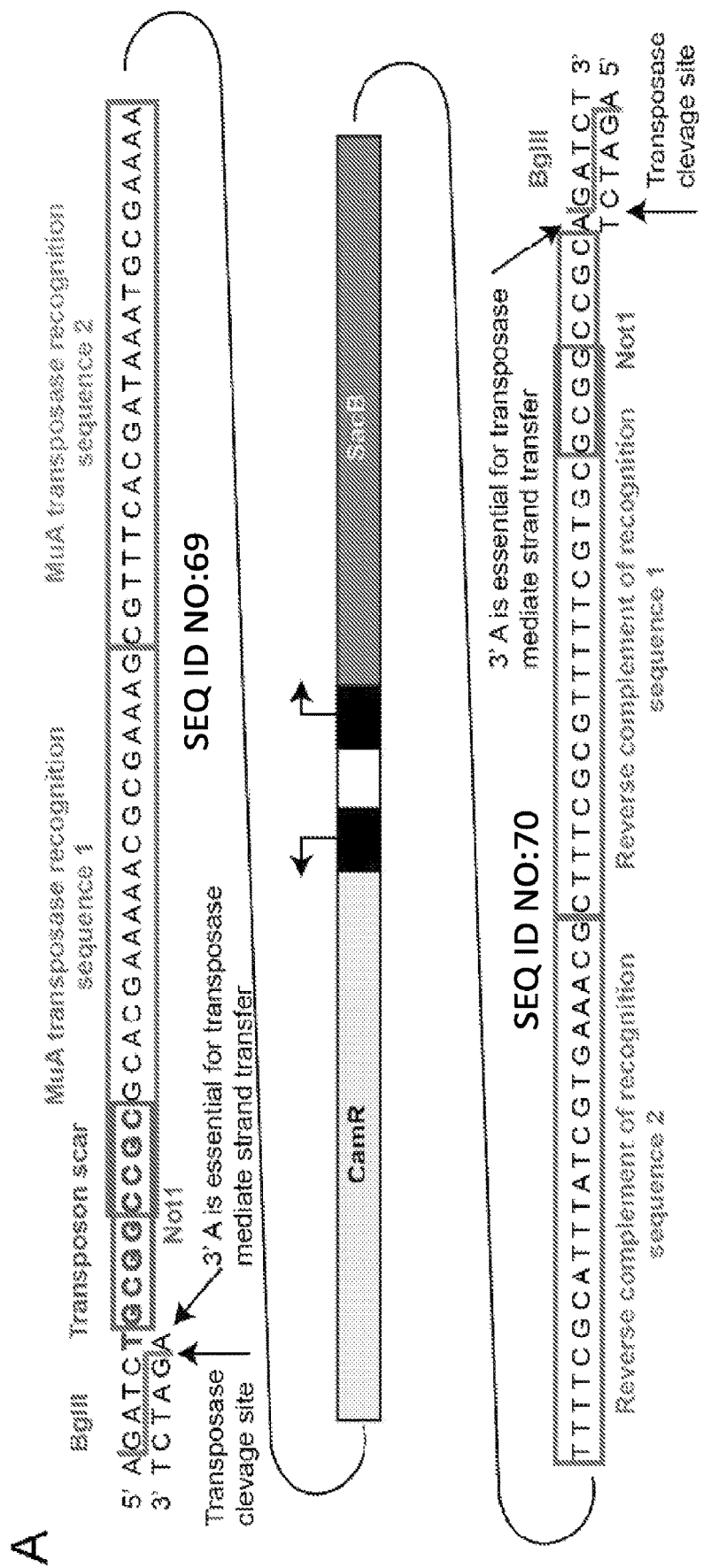
FIG. 20. Transposon key features and scar options. (A) Cartoon representation of the transposon. The transposon is digested out of its storage vector pAY438 using the BglII restriction enzymes. This leaves the minimal 3' "A" that is essential for MuA mediated strand transfer during the transposition reaction. All bases outside of this "A" get cleaved from the transposon following transposition. Highlighted bases will remain in the gene of interest after the transposon has been excised out. The NotI site is embedded in the MuA recognition site. The MuA recognition sites are show in boxes. The CamR and SacB ORFs with their own constitutive promoters are contained within the MuA recognition sequences. (B) The transposon will insert irrespective of frame: therefore, for each of the three frames, we describe the potential bases that need to be added to the ZFP to ensure that both regions of MBP are in frame with the ZFP insertion. By adding a single base to the front of the ZFP for frame 2, all the linkers will be alanines, except for the codon interrupted by transposon, and this cannot become a STOP codon. Frames 1 and 3 yielded poor linker options after the frame of the ZFP and MBP was preserved. Codons containing a "*" are controllable by varying the "X" base identity.
Figure 20:
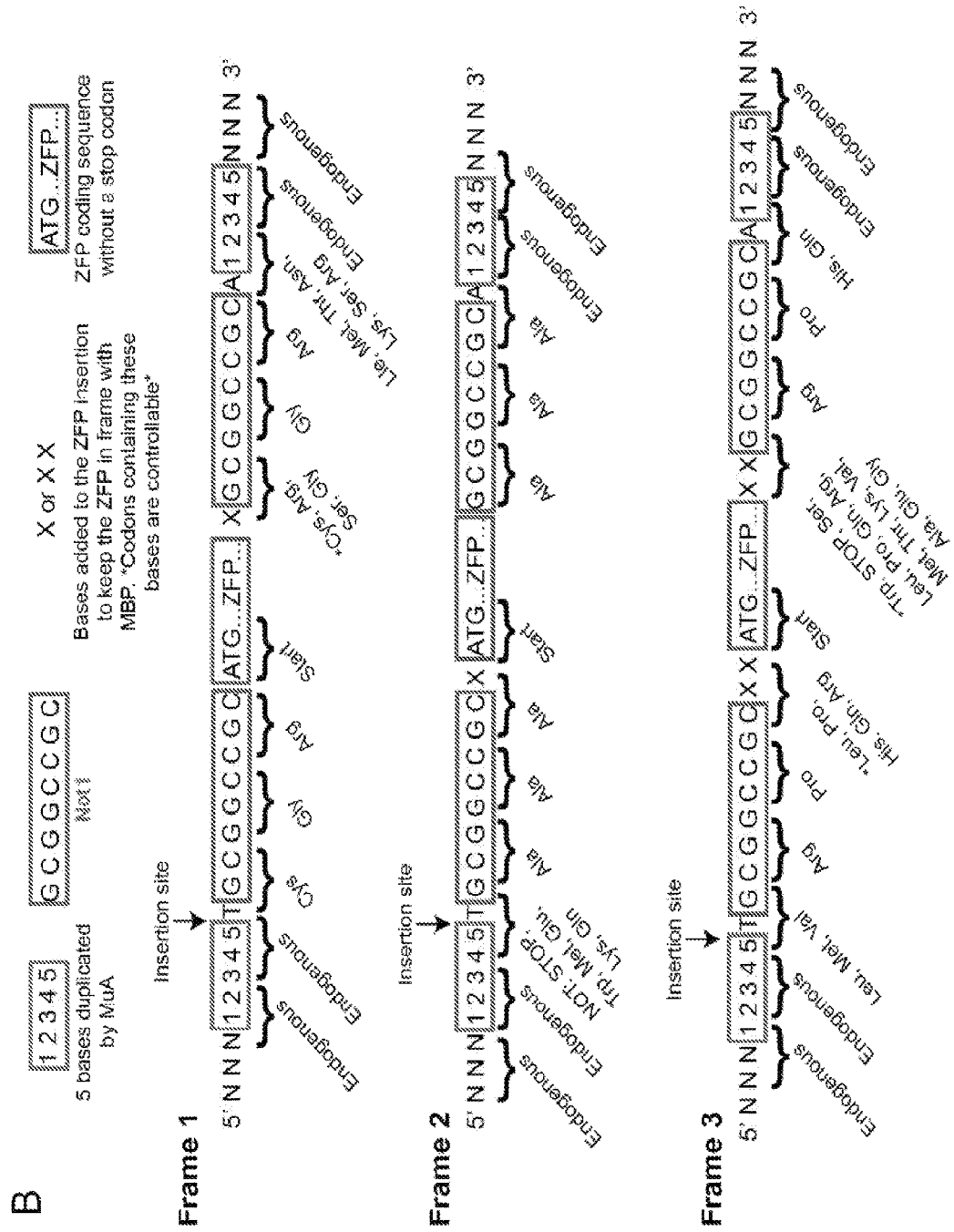

Intriguingly, however, a biosensor matching the original reference biosensor (e.g., a ZFP insertion 316R) was not recovered by the BERDI method, and we next investigated why this may be. One possible explanation is that the linkers introduced via the BERDI method differ from those included in the reference biosensor. The reference biosensor has two amino linkers on either side of the ZFP—lysine and leucine on the 5' end of the ZFP insertion and an asparagine and valine on the 3' end—whereas the BERDI method introduces three alanines on either side of the ZFP (FIG. 20). To investigate the impact of this difference in linkers, a biosensor was generated in which the ZFP was inserted at 316R, with three alanines on each side of the ZFP, and this construct was compared to the original reference biosensor (FIG. 19A). Surprisingly, the 316R biosensor with 3 Ala-linkers (mimicking the transposon scar) completely lost its ability to repress the GFP reporter. This observation could explain why the BERDI method did not recover a single ZFP insertion at 316R, and moreover, it demonstrates the importance of linker length (and potentially composition) on impacting overall biosensor performance. To further investigate how linker length may affect biosensor performance, three variants of the 335P biosensor (with 3AA linkers) were generated, with reduced linker lengths (0-2 AA on each side of the ZFP). As the linker length shortened, the repression of the biosensor decreased (FIGS. 17B-C). Interestingly, the maltose-responsiveness also varied with linker length, such that the 1AA 335P biosensor exhibited the best combination of promoter repression and maltose responsiveness. Altogether, these observations both validate the BERDI method for generating novel functional biosensors and indicate that this modular biosensor design is amenable to further refinement of biosensor performance.

Discussion

In this study, we developed and implemented the BERDI method for the generation of maltose-responsive MBP-ZFP fusion proteins in a rapid and efficient manner to find three new biosensors. The fact that multiple insertions produced a bi-functional protein is not surprising given that a previous study found twelve functional insertions for a circular permuted GFP into MBP using a similar method (Nadler, Morgan, Flamholz, Kortright and Savage, 2016). Additionally, another transposon insertion study demonstrated multiple bi-functional insertions of a cytochrome into β-lactamase (Edwards, Busse, Allemann and Jones, 2008), demonstrating that if multiple possible insertions exist, this method is capable of identifying them. A possible explanation for the tolerance of the proteins studied both here and in previous research is that many circularly permuted proteins are able to retain their function, demonstrated in a study that found 15 unique functional circular permutations of an adenylate kinase using transposon mutagenesis (Mehta, Liu and Silberg, 2012). A second explanation may be that these are monomeric proteins, as homodimers would require the protein complex to tolerate two changes simultaneously. These findings emphasize the need for library based approaches, like the one described here, given the propensity for a given protein to have multiple positions where functional fusions can be created.

Despite some indication that our library did not sample the entire insertion space due to limitations such as amplification bias, we found three novel functional biosensors in our library, and six variants that were out-of-frame, but that still exhibited mild (less than 2-fold) inducible repression (5E, 31G, 188G, 194T, 213I, and 262V). The three biosensors that were enriched in the screening process were not detected by either colony (Sanger) sequencing or NGS, indicating that our screening method can isolate infrequent mutants from the initial library. As for the out-of-frame "repressors", we hypothesize that this is due to non-specific translation, since the start codon of the ZFP remained in the final constructs. Therefore, it is possible that ribosomes still translated the full ZFP along with the downstream portion of MBP (out of frame), leading to a functional repressor. Thus, in future implementations of the BERDI method, it may be desirable to remove the start codon from the ZFP prior to library construction to minimize this issue and further enrich for productive biosensors over these false positives. In any event, this phenomenon did not preclude our identification of functional biosensors, but rather it necessitated clonal analysis of more candidate biosensors in the final step of the selection. Should the problem of false positive repressors prove intractable, an alternative solution would be to add a FACS-based screen to enrich for ligand-responsive biosensors prior to clonal analysis.

One of our newly discovered biosensors (270A) had a double ZFP insertion, which outperformed a similar biosensor comprising a single ZFP insertion at this position. It is possible that the presence of two ZFP domains, if correctly folded, increased repression due to the higher potential conformational shift. While this phenomenon is neither problematic or advantageous, it is inherently tied to our use of a unique restriction site within the transposon recognition sequences during library generation, such that it seems reasonable to accept this rare occurrence as a possible event that may occur during library creation. If this phenomenon were to prove problematic, library generation could be performed with a greater ratio of backbone plasmid to ZFP cassette during the applicable ligation step. Alternatively, mutagenesis of the transposon recognition sequences might reveal an alternative method that removes this possibility, although such a study is outside the scope of this investigation, and our results suggest that such a modification of the library generation method is not necessary.

Biosensor dose is critical when evaluating biosensor performance. Increasing biosensor expression increases the repression of the reporter, however it also limits the sensitivity to maltose. It is possible that the binding of maltose does not ever completely ablate the ability of the biosensor to bind DNA, therefore, regardless of intracellular maltose concentrations, the reporter may never be completely unbound by biosensors. This performance characteristic is likely to be unique for every biosensor created, which can be characterized by a dose response analysis of both biosensor and ligand to tune desired biosensor properties.

Because protein structure and functional are so often intertwined, linker composition is vital to biosensor performance. The reference biosensor was not found in the transposon based screen due to the differences in the linkers. However, three novel biosensors were found. This implies that not only does linker composition matter, but that if we had chosen different linkers in the transposon design, we likely still would have found biosensors, albeit potentially at entirely different sites. We hypothesized that using too long of a linker would reduce the degree to which ligand binding induces conformational changes that are translated through the protein (e.g., via an allosteric mechanism) to impair DNA binding. Conversely, using no linker may prevent the ZFP from folding in a conformation conferring DNA binding in the absence of ligand. Therefore, we hypothesized that designing our library to include three alanine linkers on each side of the ZFP would potentially provide an inert and flexible linker that balances these effects. Indeed, the performance of the linker variants of the 335P biosensor largely supported this understanding of biosensor function; shortening linkers reduced biosensor-mediated repression and changed the maltose responsiveness, potentially indicating that the ZFP bound DNA to a lesser extent. Furthermore, the reference biosensor bound DNA when it included lysine and leucine residues flanking the N-terminus of the ZFP and asparagine and valine flanking the C-terminus of the ZFP, but when these linkers were each replaced with three alanines, promoter repression was ablated, implying that both length and composition of the linkers are important for performance. As is the case with biosensor expression levels, the specific linkers are likely to impact every biosensor differently. Importantly, this phenomenon may also provide an additional handle for tuning biosensor performance. Although we did not investigate this possibility in this study, systematically varying linker sequence and length, as a perturbation to a candidate biosensor, may indeed confer improved performance for some biosensors.

The 335P biosensor has the performance characteristics that make it capable of distinguishing between a high and low state of maltose that could be utilized for high-throughput screening or feedback control mechanisms. However, the biosensors found by the BERDI method may not always have the performance characteristic desired for a particular application. Therefore, using the BERDI method as a starting point to generate functional biosensors, it may be possible to improve any biosensor by saturation mutagenesis on the three alanine linkers, or even the whole protein, followed by additional rounds of sorting to enrich for different performance characteristics.

The three novel biosensors described here were all found by sorting for inducible repressors, then clonal examination for maltose responsiveness. However, if ligand-responsive biosensors prove to be exceptionally rare, it could be useful to use FACS to enrich for ligand-responsive biosensors, prior to clonal analysis, as noted above. Additionally, instead of using GFP and FACS as the screening system for ligand responsive biosensor, GFP could be replaced with a gene conferring a survival selection. For example, if the reporter drove expression of the tetA gene, encoding the tetracycline/H+ antiporter, since the ZFP represses transcription, cells that could not alleviate this repression in the presence of the ligand would be selected against when challenged with tetracycline. Therefore, growth on tetracycline could be used as another way to enrich for rare, ligand-responsive, biosensor variants.

Here we demonstrate that the BERDI method is capable of generating novel metabolite-responsive biosensors from a metabolite-binding protein. Furthermore, we found that insertion of the ZFP into several positions of this model metabolite-binding protein resulted in functional biosensors. Importantly, the BERDI method can potentially be generalized to convert any metabolite binding protein, since care was taken to ensure that no part of the method was specific to maltose binding protein by design. Finally, the BERDI method enables the development of novel biosensors without relying upon prior knowledge about permissive sites within the ligand-binding protein, potentially enabling this method to be applied to less studied proteins. Ultimately, this approach could potentially be extended to generate novel biosensors from virtually any candidate metabolite binding protein for a range of applications in microbiology and synthetic biology.

Abbreviations

MBP, Maltose binding protein; ZFP, Zinc finger protein; IPTG, Isopropyl β-D-1-thiogalactopyranoside; LB, Lysogeny broth; OD, Optical density at 600 nm; NGS, Next generation sequencing; GFP, Green fluorescent protein; TAE, tris acetate EDTA; EDTA, ethylenediaminetetraacetic acid; bla, TEM1 β-lactamase.

REFERENCES

Binder S., Schendzielorz G., Stabler N., Krumbach K., Hoffmann K., Bott M. and Eggeling L. (2012) A high-throughput approach to identify genomic variants of bacterial metabolite producers at the single-cell level. Genome biology, 13, R40. First published on, doi: 10.1186/gb-2012-13-5-r40.

Brockman I. M. and Prather K. L. (2015) Dynamic metabolic engineering: New strategies for developing responsive cell factories. Biotechnol J. First published on, doi: 10.1002/biot.201400422.

Chou H. H. and Keasling J. D. (2013) Programming adaptive control to evolve increased metabolite production. Nat Commun, 4, 2595. First published on, doi: 10.1038/ncomms3595.

Collins C. H., Arnold F. H. and Leadbetter J. R. (2005) Directed evolution of *Vibrio fischeri* LuxR for increased sensitivity to a broad spectrum of acyl-homoserine lactones. Mol Microbiol, 55, 712-723. First published on, doi: 10.1111/j.1365-2958.2004.04437.x.

Collins C. H., Leadbetter J. R. and Arnold F. H. (2006) Dual selection enhances the signaling specificity of a variant of the quorum-sensing transcriptional activator LuxR. Nat Biotechnol, 24, 708-712. First published on, doi: 10.1038/nbt1209.

Dahl R. H., Zhang F., Alonso-Gutierrez J., Baidoo E., Batth T. S., Redding-Johanson A. M., Petzold C. J., Mukhopadhyay A., Lee T. S., Adams P. D. et al. (2013) Engineering dynamic pathway regulation using stress-response promoters. Nat Biotechnol, 31, 1039-1046. First published on, doi: 10.1038/nbt.2689.

Dietrich J. A., McKee A. E. and Keasling J. D. (2010) High-throughput metabolic engineering: advances in small-molecule screening and selection. Annu Rev Biochem, 79, 563-590. First published on, doi: 10.1146/annurev-biochem-062608-095938.

Dietrich J. A., Shis D. L., Alikhani A. and Keasling J. D. (2013) Transcription factor-based screens and synthetic selections for microbial small-molecule biosynthesis. ACS Synth Biol, 2, 47-58. First published on, doi: 10.1021/sb300091d.

Edwards W. R., Busse K., Allemann R. K. and Jones D. D. (2008) Linking the functions of unrelated proteins using a novel directed evolution domain insertion method. Nucleic Acids Res, 36, e78. First published on, doi: 10.1093/nar/gkn363.

Farmer W. R. and Liao J. C. (2000) Improving lycopene production in *Escherichia coli* by engineering metabolic control. Nat Biotechnol, 18, 533-537. First published on, doi: 10.1038/75398.

Feng J., Jester B. W., Tinberg C. E., Mandell D. J., Antunes M. S., Chari R., Morey K. J., Rios X., Medford J. I., Church G. M. et al. (2015) A general strategy to construct small molecule biosensors in eukaryotes. Elife, 4. First published on, doi: 10.7554/eLife.10606.

Golynskiy M. V., Koay M. S., Vinkenborg J. L. and Merkx M. (2011) Engineering protein switches: sensors, regulators, and spare parts for biology and biotechnology. Chembiochem, 12, 353-361. First published on, doi: 10.1002/cbic.201000642.

Guntas G., Mitchell S. F. and Ostermeier M. (2004) A molecular switch created by in vitro recombination of nonhomologous genes. Chem Biol, 11, 1483-1487. First published on, doi: 10.1016/j.chembiol.2004.08.020.

Haapa S., Suomalainen S., Eerikainen S., Airaksinen M., Paulin L. and Savilahti H. (1999) An efficient DNA sequencing strategy based on the bacteriophage mu in vitro DNA transposition reaction. Genome Res, 9, 308-315. First published on.

Kang Z., Zhang C., Zhang J., Jin P., Zhang J., Du G. and Chen J. (2014) Small RNA regulators in bacteria: powerful tools for metabolic engineering and synthetic biology. Applied microbiology and biotechnology, 98, 3413-3424. First published on, doi: 10.1007/s00253-014-5569-y.

Khalil A. S. and Collins J. J. (2010) Synthetic biology: applications come of age. Nat Rev Genet, 11, 367-379. First published on, doi: 10.1038/nrg2775.

Li S., Si T., Wang M. and Zhao H. (2015) Development of a Synthetic Malonyl-CoA Sensor in *Saccharomyces cerevisiae* for Intracellular Metabolite Monitoring and Genetic Screening. ACS Synth Biol. First published on, doi: 10.1021/acssynbio.5b00069.

Litcofsky K. D., Afeyan R. B., Krom R. J., Khalil A. S. and Collins J. J. (2012) Iterative plug-and-play methodology for constructing and modifying synthetic gene networks. Nat Methods, 9, 1077-1080. First published on, doi: 10.1038/nmeth.2205.

Liu D., Xiao Y., Evans B. S. and Zhang F. (2015) Negative feedback regulation of fatty acid production based on a malonyl-CoA sensor-actuator. ACS Synth Biol, 4, 132-140. First published on, doi: 10.1021/sb400158w.

Mehta M. M., Liu S. and Silberg J. J. (2012) A transposase strategy for creating libraries of circularly permuted proteins. Nucleic Acids Res, 40, e71. First published on, doi: 10.1093/nar/gks060.

Meinhardt S., Manley M. W., Jr., Becker N. A., Hessman J. A., Maher L. J., 3rd and Swint-Kruse L. (2012) Novel insights from hybrid LacI/GalR proteins: family-wide functional attributes and biologically significant variation in transcription repression. Nucleic Acids Res, 40, 11139-11154. First published on, doi: 10.1093/nar/gks806.

Michener J. K., Thodey K., Liang J. C. and Smolke C. D. (2012) Applications of genetically-encoded biosensors for the construction and control of biosynthetic pathways. Metab Eng, 14, 212-222. First published on, doi: 10.1016/j.ymben.2011.09.004.

Mohn W. W., Garmendia J., Galvao T. C. and de Lorenzo V. (2006) Surveying biotransformations with a la carte genetic traps: translating dehydrochlorination of lindane (gamma-hexachlorocyclohexane) into lacZ-based phenotypes. Environ Microbiol, 8, 546-555. First published on, doi: 10.1111/j.1462-2920.2006.00983.x.

Moonsamy P. V., Williams T., Bonella P., Holcomb C. L., Hoglund B. N., Hillman G., Goodridge D., Turenchalk G. S., Blake L. A., Daigle D. A. et al. (2013) High throughput HLA genotyping using 454 sequencing and the Fluidigm Access Array System for simplified amplicon library preparation. Tissue Antigens, 81, 141-149. First published on, doi: 10.1111/tan.12071.

Murphy K. C., Campellone K. G. and Poteete A. R. (2000) PCR-mediated gene replacement in *Escherichia coli*. Gene, 246, 321-330.

Nadler D. C., Morgan S. A., Flamholz A., Kortright K. E. and Savage D. F. (2016) Rapid construction of metabolite biosensors using domain-insertion profiling. Nat Commun, 7, 12266. First published on, doi: 10.1038/ncomms12266.

Oakes B. L., Nadler D. C., Flamholz A., Fellmann C., Staahl B. T., Doudna J. A. and Savage D. F. (2016) Profiling of engineering hotspots identifies an allosteric CRISPR-Cas9 switch. Nat Biotechnol, 34, 646-651. First published on, doi: 10.1038/nbt.3528.

Quiocho F. A., Spurlino J. C. and Rodseth L. E. (1997) Extensive features of tight oligosaccharide binding revealed in high-resolution structures of the maltodextrin transport/chemosensory receptor. Structure, 5, 997-1015. First published on.

Rogers J. K., Guzman C. D., Taylor N. D., Raman S., Anderson K. and Church G. M. (2015) Synthetic biosensors for precise gene control and real-time monitoring of metabolites. Nucleic Acids Res. First published on, doi: 10.1093/nar/gkv616.

Salis H. M., Mirsky E. A. and Voigt C. A. (2009) Automated design of synthetic ribosome binding sites to control protein expression. Nat Biotechnol, 27, 946-950. First published on, doi: 10.1038/nbt.1568.

Segall-Shapiro T. H., Nguyen P. Q., Dos Santos E. D., Subedi S., Judd J., Suh J. and Silberg J. J. (2011) Mesophilic and hyperthermophilic adenylate kinases differ in their tolerance to random fragmentation. J Mol Biol, 406, 135-148. First published on, doi: 10.1016/j.jmb.2010.11.057.

Shis D. L., Hussain F., Meinhardt S., Swint-Kruse L. and Bennett M. R. (2014) Modular, multi-input transcriptional logic gating with orthogonal LacI/GalR family chimeras. ACS Synth Biol, 3, 645-651. First published on, doi: 10.1021/sb500262f.

Strianese M., Staiano M., Ruggiero G., Labella T., Pellecchia C. and D'Auria S. (2012) Fluorescence-based biosensors. Methods Mol Biol, 875, 193-216. First published on, doi: 10.1007/978-1-61779-806-1_9.

Tang S. Y. and Cirino P. C. (2011) Design and application of a mevalonate-responsive regulatory protein. Angew Chem Int Ed Engl, 50, 1084-1086. First published on, doi: 10.1002/anie.201006083.

Tang S. Y., Fazelinia H. and Cirino P. C. (2008) AraC regulatory protein mutants with altered effector specificity. J Am Chem Soc, 130, 5267-5271. First published on, doi: 10.1021/ja7109053.

Tang S. Y., Qian S., Akinterinwa O., Frei C. S., Gredell J. A. and Cirino P. C. (2013) Screening for enhanced triacetic acid lactone production by recombinant *Escherichia coli* expressing a designed triacetic acid lactone reporter. J Am Chem Soc, 135, 10099-10103. First published on, doi: 10.1021/ja402654z.

van Sint Fiet S., van Beilen J. B. and Witholt B. (2006) Selection of biocatalysts for chemical synthesis. Proc Natl Acad Sci USA, 103, 1693-1698. First published on, doi: 10.1073/pnas.0504733102.

Venayak N., Anesiadis N., Cluett W. R. and Mahadevan R. (2015) Engineering metabolism through dynamic control. Curr Opin Biotechnol, 34, 142-152. First published on, doi: 10.1016/j.copbio.2014.12.022.

Younger A. K., Dalvie N. C., Rottinghaus A. G. and Leonard J. N. (2016) Engineering Modular Biosensors to Confer Metabolite-Responsive Regulation of Transcription. ACS Synth Biol. First published on, doi: 10.1021/acssynbio.6b00184.

Zhang F., Carothers J. M. and Keasling J. D. (2012) Design of a dynamic sensor-regulator system for production of chemicals and fuels derived from fatty acids. Nat Biotechnol, 30, 354-359. First published on, doi: 10.1038/nbt.2149.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A system comprising:
   (a) a fusion protein that functions as a biosensor, the fusion protein comprising a ligand-binding protein (LBP) and a DNA-binding protein (DBP), the fusion protein comprising an amino acid sequence represented as:
   (N-terminal portion of the LBP)-(DBP)-(C-terminal portion of the LBP); and
   (b) a promoter which can be operably linked to a reporter gene,
   wherein the promoter comprises at least one heterologous binding site that is specific for the DBP and the fusion protein binds to the ligand and modulates expression from the promoter.

2. The system of claim 1, wherein the fusion protein has a first binding affinity ($K_{d1}$) for the promoter in the absence of the ligand, and the fusion protein has a second binding affinity ($K_{d2}$) for the promoter in the presence of the ligand, such that $K_{d1} < K_{d2}$ and transcription of the reporter gene is de-repressed or activated in the presence of the ligand.

3. The system of claim 2, wherein de-repression or activation is proportional to concentration of the ligand in the system.

4. The system of claim 2, wherein $K_{d1}$ is <about 1 nM, 0.5 nM, 0.2 nM, 0.1 nM, 0.05 nM, 0.02 nM, 0.01 nM or lower.

5. The system of claim 2, wherein $K_{d2}$ is >about 0.02 nM, 0.05 nM, 0.1 nM, 0.2 nM, 0.5 nM, 1 nM, 2 nM or higher.

6. The system of claim 2, wherein the ratio $K_{d2}:K_{d1}$ is at least about 5, 10, 20, 50, 100, 500, 1000 or more.

7. The system of claim 1, wherein the fusion protein has a first binding affinity ($K_{d1}$) for the promoter in the absence of the ligand, and the fusion protein has a second binding affinity ($K_{d2}$) for the promoter in the presence of the ligand, such that $K_{d1} > K_{d2}$ and transcription of the reporter gene is repressed or de-activated in the presence of the ligand.

8. The system of claim 7, wherein repression or de-activation is proportional to concentration of the ligand in the system.

9. The system of claim 7, wherein $K_{d2}$ is <about 1 nM, 0.5 nM, 0.2 nM, 0.1 nM, 0.05 nM, 0.02 nM, 0.01 nM or lower.

10. The system of claim 7, wherein $K_{d1}$ is >about 0.02 nM, 0.05 nM, 0.1 nM, 0.2 nM, 0.5 nM, 1 nM, 2 nM or higher.

11. The system of claim 7, wherein the ratio $K_{d1}:K_{d2}$ is at least about 5, 10, 20, 50, 100, 500, 1000 or more.

12. The system of claim 1, wherein the N-terminal portion of the LBP within the fusion protein comprises an amino acid sequence of at least about 10, 20, 30, 40, 50, 60, 70, 80, 90, or 100 contiguous amino acids from the N-terminus of the LBP.

13. The system of claim 1, wherein the C-terminal portion of the LBP within the fusion protein comprises an amino acid sequence of at least about 10, 20, 30, 40, 50, 60, 70, 80, 90, or 100 contiguous amino acids from the C-terminus of the LBP.

14. The system of claim 1, wherein the ligand is a cellular metabolite.

15. The system of claim 1, wherein the LBP is maltose binding protein.

16. The system of claim 1, wherein the DBP comprises one or more DNA-binding domains selected from the group consisting of a zinc-finger protein (ZFP) DNA-binding domain, a transcription activator-like effector (TALE) DNA-binding domain, and a clustered regularly interspaced short palindromic repeat (CRISPR) DNA-binding domain.

17. The system of claim 16, wherein the ZFP is BCR-ABL1.

18. The system of claim 1, wherein the promoter is a prokaryotic promoter.

19. The system of claim 18, wherein the promoter comprises two or more binding sites for the DBP.

20. The system of claim 19, wherein the binding sites are located at one or more positions selected from:
   (i) between the −10 box (TATA box) and the −35 box (GC-rich region);
   (ii) adjacent to the −10 box (TATA box) or within 5 nucleotides of the −10 box (TATA box); and
   (iii) adjacent to the −35 box (GC-rich region) or within 5 nucleotide of the −35 box (GC-rich region).

21. A method for preparing a fusion protein for use as a biosensor, the fusion protein comprising a ligand-binding protein (LBP) and a DNA-binding protein (DBP) or portions or fragments thereof, where the fusion protein comprises an amino acid sequence represented as (N-terminal portion of the LBP)-(DBP)-(C-terminal portion of the LBP), the method comprising preparing a library of fusion proteins by inserting the DBP randomly into the amino acid sequence of the LBP via performing a recombinant DNA method, and selecting a fusion protein from the library of fusion proteins as a biosensor.

22. The method of claim 21, wherein the recombinant DNA method is transposon-mediated DNA recombination.

23. The method of claim 21, wherein the fusion protein is selected as a biosensor via testing whether the fusion protein modulates transcription from a promoter comprising a binding site for the DBP of the fusion protein in the presence or absence of the ligand for the LBP of the fusion protein.

* * * * *